(12) United States Patent
Manoharan et al.

(10) Patent No.: US 7,851,615 B2
(45) Date of Patent: *Dec. 14, 2010

(54) LIPOPHILIC CONJUGATED IRNA AGENTS

(75) Inventors: Muthiah Manoharan, Weston, MA (US); Kallanthottahil G. Rajeev, Wayland, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 483 days.

This patent is subject to a terminal disclaimer.

(21) Appl. No.: 11/833,934

(22) Filed: Aug. 3, 2007

(65) Prior Publication Data

US 2008/0108801 A1 May 8, 2008

(51) Int. Cl.
*C07H 21/04* (2006.01)
*A61K 31/70* (2006.01)
(52) U.S. Cl. .................. 536/24.5; 536/23.1; 514/44
(58) Field of Classification Search .................. None
See application file for complete search history.

(56) References Cited

U.S. PATENT DOCUMENTS

| | | | |
|---|---|---|---|
| 4,572,912 | A | 2/1986 | Yoshioka et al. |
| 5,328,470 | A | 7/1994 | Nabel et al. |
| 5,519,134 | A * | 5/1996 | Acevedo et al. ............. 544/243 |
| 5,646,126 | A | 7/1997 | Cheng et al. |
| 6,147,204 | A * | 11/2000 | Gold et al. ................. 536/24.5 |
| 6,239,107 | B1 * | 5/2001 | Gozes et al. ................. 514/14 |
| 6,509,323 | B1 | 1/2003 | Davis et al. |
| 2002/0016285 | A1 | 2/2002 | Bhatt et al. |
| 2002/0086356 | A1 | 7/2002 | Tuschl et al. |
| 2003/0008818 | A1 | 1/2003 | Pun et al. |
| 2003/0170891 | A1 * | 9/2003 | McSwiggen ................ 435/366 |
| 2005/0107325 | A1 | 5/2005 | Manoharan et al. |
| 2005/0119214 | A1 | 6/2005 | Manoharan et al. |
| 2005/0164235 | A1 | 7/2005 | Manoharan et al. |
| 2006/0058266 | A1 | 3/2006 | Manoharan et al. |

FOREIGN PATENT DOCUMENTS

| | | |
|---|---|---|
| EP | 0023725 | 2/1981 |
| WO | WO 9203464 A1 * | 3/1992 |
| WO | WO 00/44895 A1 | 8/2000 |
| WO | WO 00/44914 A1 | 8/2000 |
| WO | WO 01/36646 A1 | 5/2001 |
| WO | WO 01/75164 A2 | 10/2001 |
| WO | WO 01/98273 | 12/2001 |
| WO | WO 02/44321 A2 | 6/2002 |
| WO | WO 03/051839 | 6/2003 |
| WO | WO 2004/065601 A2 | 8/2004 |
| WO | WO 2005/061499 | 7/2005 |

OTHER PUBLICATIONS

Levin et al. "Rapid, One-Pot Conversion of Aryl Fluorides into Phenols with 2-Butyn-1-Ol and Potassium t-Butoxide in Dmso". Synthetic Communications 32(9):1401-1406, 2002.

Rogers et al. "Mild conversion of electron deficient aryl fluorides to phenols using 2-(methylsulfonyl)ethanol". Tetrahedron Letters 43:3585-3587, 2002.

Wirz et al. "Facile chemoenzymatic preparation of enantiomerically pure 2-methylglycerol derivatives as versatile trifunctional C4-synthons". J. Org. Chem. 58:3980-3984, 1993.

Sajiki et al. "Highly chemoselective drdrogenation with retention of the epoxide function using a heterogeneous Pd/C—Ethylenediamine catalyst and THF". Chem. Eur. J. 6(12):2200-2204, 2000.

Amosova el al., "Effect of the 1-(2'-deoxy-beta-D-ribofuranosyl)-3-nitropyrrole residue on the stability of DNA duplexes and triplexes" *Nucleic Acids Res.* 25:1930-1934_(1997.

An et al., "Synthesis of Novel 3 '-C-Methylene Thymidinc and 5-Methyluridine/Cytidine H-Phosphonates and Phosphonamidites for New Backbone Modification of Oligonucleotides" *J. Org. Chem.* 66:2789-2801 (2001).

Ausin et al., "Synthesis of Amino- and Guanidino-G-Clamp PNA Monomers" *Organic Letters* 4:4073-4075 (2002).

Aoki et al., "Potential tumor-targeting peptide vector of histidylated oligolysine conjugated to a tumor-homing RGD MOTIF" *Cancer Gene Therpy* 8:783-787 (2001).

Basbaum et al, "Focalized proteolysis: spatial and temporal regulation of extra cellular matrix degradation at the cell surface" *Curr. Opin. Cell Biol.* 8:731-738 (1996).

Benezra et al., "The Id proteins and angiogenesis" *Oncogene* 20(58):8334-41 (2001).

Berger et al., "Universal bases for hybridization, replication and chain termination" *Nucleic Acids Res.* 28:2911-2914 (2000).

Bergstrom et al., "Synthesis, Structure, and Deoxyribonucleic Acid Sequencing with a Universal Nucleoside: 1-(2'-Deoxy-β-D-ribofuranosyl)-3-nitropyrrole" *Am. Chem. Soc.* 117:1201-1209 (1995).

Bernstein et al., "Role for a bidentate ribonuclease in the initiation step of RNA interference" *Nature* 409:363-366 (2001).

Birkedal-Hansen et al., "Matrix Metalloproteinases: A Review" *Crit. Rev. Oral Biol. Med.* 4:197-250 (1993).

Boyd, "Invasion and metastasis" *Cancer Metastasis Rev.* 15(1):77-89 (1996).

Brinckerhoff et al., "Matrix metalloproteinases: a tail of a frog that became a prince" *Nature Reviews* 3:207-214 (2002).

Brotschi et al., "A Stable DNA Duplex Containing a Non-Hydrogen-Bonding and Non-Shape-Complementary Base Couple: Interstrand Stacking as the Stability Determining Factor" *Agnew Chem. Int. Ed.* 40:3012-3014 (2001).

(Continued)

*Primary Examiner*—Tracy Vivlemore
(74) *Attorney, Agent, or Firm*—Nixon Peabody LLP; Jeffrey N. Townes

(57) ABSTRACT

The invention relates to iRNA agents, which preferably include a monomer in which the ribose moiety has been replaced by a moiety other than ribose. The inclusion of such a monomer can allow for modulation of a property of the iRNA agent into which it is incorporated, e.g., by using the non-ribose moiety as a point to which a ligand or other entity, e.g., a lipophilic moiety is directly, or indirectly, tethered. The invention also relates to methods of making and using such modified iRNA agents.

25 Claims, 12 Drawing Sheets

OTHER PUBLICATIONS

Chaloin et al., "Design of Carrier Peptide-Oligonucleotide Conjugates with Rapid Membrane Translocation and Nuclear Localization Properties" *Biochem. Biophys. Res. Commun.* 243:601 608 (1998).

Chao et al., "BCL-2 Family: Regulators of Cell Death" *Annu. Rev. Immunol.* 16:395-419 (1998).

Chen et al., "Gene therapy for brain tumors: regression of experimental gliomas by adenovirus-mediated gene transfer in vivo" *Proc. Natl. Acad. Sci. USA* 91:3054-3057 (1994).

Childs et al., "The MDR Superfamily of Genes and Its Biological Implications" *Imp. Adv. Oncol.* 21-36 (1994).

Chothia et al, "The Molecular Structure of Cell Adhesion Molecules" *Annu. Rev. Biochem.* 66:823-862 (1997).

Colledge et al., "Disruption of c-mos causes parthenogenetic development of unfertilized mouse eggs" *Nature* 370: 65-68 (1994.

Corey et al., "Protection of Hydroxyl Groups as *tert*-Butyldimethylsilyl Derivatives" *J. Am. Chem. Soc.* 94:6190-6191 (1972).

Cormier et al., "Synthesis of hexanucleotide analogues containing diisopropylsilyl internucleotide linkages" *Nucleic Acids Res.* 16:4583-4594 (1988).

Cosstick et al, "Solid Phase Synthesis of Oligonucleotides Containing 3'-Thiothymidine" *Tetrahedron Lett.* 30(35):4693-4039 (1989).

D'Ari, "Cycle-regulated genes and cell cycle regulation" *Bioassays* 23(7):563-565 (2001).

De et al, "Structure-Activity Relationships for Antiplasmodial Activity among 7-Substituted 4-Aminoquinolines" *J. Med. Chem.* 41:4198-4926 (1998).

Deller et al., "Cell surface receptors" *Curr. Opin. Struct. Biol.* 10(2):213-219 (2000).

Derossi et al., "The Third Helix of the Antennapedia Homeodomain Translocates through Biological Membranes" *J. Biol. Chem.* 269(14):10444-10450 (1994).

Eckstein, "Oligonucleotides and Analogues, A practical approach" Table of Contents *IRL Press* (1991).

Edge, et al., "Synthetic Analogues of Polynucleotides. Part VIII. Analogues of Oligonucleotides containing Carboxymethylthymidine" *J. Chem. Soc. Perkin Trans.* 1:1991-1996 (1972).

Elbashir et al., "RNA interference is mediated by 21- and 22-nucleotide RNAs" *Genes and Dev.* 15:188-200 (2001).

Elmquist et al., "VE-Cadherin-Derived Cell-Penetrating Peptide, pVEC, with Carrier Functions" *Exp. Cell Res.* 269:237-244 (2001).

Fang et al., "Fluoride-cleavable biotinylation phosphoramidite for 5'-end-labeling and affinity purification of synthetic oligonucleotides" *Nucleic Acids Res.* 31(2):708-715 (2003).

Fire et al., "Potent specific genetic interference by double-stranded RNA in *Caenorhabditis elegans*" *Nature* 391:806-811 (1998).

Fischer et al., "Cellular delivery of impermeable effector molecules in the form of conjugates with peptides capable of mediating membrane translocation" *Bioconjugate Chem.* 12:825-841 (2001).

Flanagan et al., "A cytosine analog that confers enhanced potency to antisense oligonucleotides" *Proc. Natl. Acad. Sci. USA* 96:3513-3518 (1999).

Fotedar et al., "Apoptosis and the cell cycle" *Prog. Cell Cycle Res.* 2:147-163 (1996).

Gante, "Azapeptides" *Synthesis* 405-413 (1989).

Gould et al., "Angiogenesis: An Expanding Universe" *Hum. Pathol.* 33(11):1061-1063 (2002).

Guckian et al., "Structure and Base Pairing Properties of a Replicable Nonpolar Isostere for Deoxyadenosine" *J. Org. Chem.* 63:9652-9656 (1998).

Hammond, "Argonaute2, a link between genetic and biochemical analyses of RNAi" *Science* 293:1146-1150 (2001).

Hashimoto et al., "Parthenogenetic activation of oocytes in c-mos-deficient mice" *Nature* 370:68-71 (1994).

Hanahan et al., "The Hallmarks of Cancer" *Cell* 100:57-70 (2000).

Haubner et al., "Glycosylated RGD-Containing Peptides: Tracer for Tumor Targeting and Angiogenesis Imaging with Improved Biokinetics" *J. Nucl. Med.* 42(2):326-336 (2001).

Holmes et al., "Steric inhibition of human immunodeficiency virus type-1 Tat-dependent trans-activation in vitro and in cells by oligonucleotides containing 2'-0-methyl G-clamp ribonucleoside analogues" *Nucleic Acids Res.* 31:2759-2768 (2003).

Holmes et al., "The Synthesis of 2'-0-Methyl G-Clamp Containing Oligonucleotides and Their Inhibition of the HIV-1 Tat-TAR Interaction," *Nucleosides, Nucleotides & Nucleic Acids* 22:1259 1262 (2003).

Hyrup et al., "Peptide Nucleic Acids (PNA): Synthesis, Properties and Potential Applications" *Bioorganic & Medicinal Chemistry* 4:5-23 (1996).

Iyer et al., "3*H*-1,2-Benzodithiole-3-one 1,1-Dioxide as an Improved Sulfurizing Reagent in the Solid-Phase Synthesis of Oligodeoxyribonucleoside Phosphorothioates" *J. Am. Chem. Soc.*, 112:1253-1254(1990).

Katajisto et al., "Solid-Phase Synthesis of Multiantennary Oligonucleotide Glycoconjugates Utilizing On-Support Oximation" *Bioconjugate Chem.* 15:890-896 (2004).

Kawasaki et al., "Uniformly Modified 2'-Deoxy-2'-fluoro Phosphorothioate Oligonucleotides as Nuclease-Resistant Antisense Compounds with High Affinity and Specificity for RNA Targets" *J. Med Chem.* 36:831-841 (1993).

Ketting et al., "Dicer functions in RNA interference and in synthesis of small RNA involved in developmental timing in *C. elegans*" *Genes Dev.* 15(20):2654-2659 (2001).

Krepela, "Cysteine proteinases in tumor cell growth and apoptosis" *Neoplasma* 48(5):332-349 (2001).

Kumar et al., "Express Protocol for Functionalization of Polymer Supports for Oligonucleotide Synthesis" *Nucleosides & Nucleotides* 15(4):879-888 (1996).

Lam et al., "A new type of synthetic peptide library for identifying ligand-binding activity" *Nature* 354:82-84 (1991).

Lan et al., "Minor Groove Hydration is Critical to the Stability of DNA Duplexes" *J. Am. Chem. Soc.* 122:6512-6513 (2000).

Larock, "Table of Contents from *Comprehensive Organic Transformation*" VCH Publishers, Inc. (1989).

Limbach et al. "Summary: the modified nucleosides of RNA" *Nucleic Acids Res.* 22:2183-2196 (1994).

Lindgren et at, "Cell-penetrating peptides" *Tips* 21:99-103 (2000).

Liu et al., "Bi-stranded, multisite replication of a base pair between difluorotoluene and adenine: confirmation by 'inverse' sequencing" *Chem. Biol.* 4:919-926 (1997).

Loakes, "The applications of universal DNA base analogues" *NAR* 29:2437-2447 (2001).

Loakes, "Survey and Summary: The Applications of Universal DNA base analogues " *Nucleic Acid Res.* 29:2437-2447 (2001).

Maier et al., "Nuclease resistance of oligonucleotides containing the tricyclic cytosine analogues phenoxazine and 9-(2-aminoethoxy)-phenoxazine ("G-clamp") and origins of their nuclease resistance properties" *Biochem.* 41:1323-1327 (2002).

Manoharan, "Oligonucleotide Conjugates as Potential Antisense Drugs with Improved Uptake, Biodistribution, Targeted Delivery, and Mechanism of Action" *Antisense Nucleic Acid Drug Devel.* 12:103-128 (2002).

Martin, "Stereoselektive Synthese von 2'-0-(2-Methoxyethyl)ribonucleosiden: Nachbargruppenbeteiligung der methyoxyethosy-Gruppe bei der Ribosylierung von Heterocyclen" *Hely. Chim. Acta* 79:1930-1938 (1996) (English abstract only).

Matray et al., "Selective and Stable DNA Base Pairing without Hydrogen Bonds" *J. Am. Chem. Soc.* 120:6191-6192 (1998).

Matrisian, "Cancer biology: Extracellular proteinases in malignancy" *Curr. Biol.* 9(20):R776-778 (1999).

McMinn et al., "Efforts toward Expansion of the Genetic Alphabet; DNA Polymerase Recognition of a Highly Stable, Self-Pairing Hydrophobic Base" *J. Am. Chem. Soc.* 121:11585-11586 (1999).

Mendelsohn et al.,. "The EGF receptor family as target for cancer therapy" *Oncogene*, 19(56):6550-6565 (2000).

Mi et al, "Characterization of a Class of Cationic Peptides Able to Facilitate Efficient Protein Tranduction in Vitro and in Vivo" *Mol. Ther.* 2(4):339-347 (2000).

Mignatti et al., "Biology and Biochemistry of proteinases in Tumor invasion" *Physiol. Rev.* 73:161-195 (1993).

Mitchell et al., "Polyarginine enters cells more efficiently than other polycationic homopolymers" *J. Pept. Res.* 56:318-325 (2000).

Morales et al., "Importance of Terminal Base Pair Hydrogen-Bonding in 3'-End Proofreading by the Klenow Fragment of DNA Polymerase I" *Biochem.* 39:2626-2632 (2000).
Moran et al., "Difluorotoluene, a Nonpolar Isostere for Thymine, Codes Specifically and Efficiently for Adenine in DNA Replication" *J. Am. Chem. Soc.* 119:2056-2057 (1997).
Müllauer et al., "Mutations in apoptosis genes: a pathogenetic factor for human disease" *Mutat. Res.* 488(3):211-231 (2001).
Nakata et al., "A Formal Total Synthesis of Erythromycin A. 2. A Convergent Synthesis of Woodward's Caramate Intermediate" *Tetrahedron Lett.* 29(18):2223-2226 (1988).
Noguchi et al., "Total Synthesis of Analogs of Topostin B, a DNA Topoisomerase I Inhibitor Part 1. Synthesis of Fragments of Topostin B-1 Analogs" *Tetrahedron* 51:10531-10544 (1995).
Nakatani et al., "Recognition of a Single Guanine Bulge by 2-Acylamino-1, 8-naphthyridine" *J. Am. Chem. Soc.* 122:2172-2177 (2000).
Nakatani et al., "Specific binding of 2-amino-1,8-naphthyridine into a single guanine bulge as evidenced by photooxidation of GG doublet" *Bioorg. Med. Chem. Lett.* 11:335-337 (2001).
Normanno et al., "The role of EGF-Related Peptides in Tumor Growth" *Front. Biosci.* 6:D685-707 (2001).
Nykänen et al., "ATP requirements and small interfering RNA structure in the RNA interference pathway." *Cell* 107:309-321 (2001).
Norton, "ID helix-loop-helix proteins in cell growth, differentiation and tumorigenesis" *J. Cell Sci.* 113(22):3897-3905 (2000).
Ogawa et al., "Efforts toward the Expansion of the Genetic Alphabet Information Storage and Replication with Unnatural Hydrophobic Base Pairs" *J. Am. Chem. Soc.* 122:3274-3287 (2000).
Ogawa et al., "Rational Design of an Unnatural Base Pair with Increased Kinetic Selectivity" *J. Am. Chem. Soc.* 122:8803-8804 (2000).
Oliver et al., "Effect of the universal base 3-nitropyrrole on the selectivity of neighboring natural bases" *Organic Lett.* 3:1977-1980 (2001).
Opalinska et al., Nature Reviews Drug Discovery, 2002, vol. 1, p. 503-514.
Parise et al., "New aspects of integrin signaling in cancer" *Semin. Cancer Biol.* 10(6):407-414 (2000).
Patri et al., "Dendritic polymer macromolecular carriers for drug delivery" *Curr. Opin. Chem. Biol.* 6:466-471 (2002).
Pooga et al., "Cell penetration by transportation" *FASEB J.* 12:67-77 (2000).
Pirrung et al., "A universal, photocleavable DNA base: nitropiperonyl 2'-deoxyriboside" *J. Org. Chem.* 66:2067-2071 (2001).
Prakash et al., "Synthesis of 2'-O'[2-[(N,N-Dimethylamino)oxy]ethyl]Modified Nucleosides and Oligonucleotides" *J. Org. Chem.* 67:357-369 (2002).
Prusiner et al., "Prion Protein Biology" *Cell* 93(3):337-348 (1998).
Quintana et al., "Design and Function of a Dendrimer-Based Therapeutic Nanodevice Targeted to Tumor Cells Through the Folate Receptor" *Pharma Res.* 19(9):1310-1316 (2002).
Rajeev et al., "High-Affinity Peptide Nucleic Acid Oligomers Containing Tricyclic Cytosine Analogues" *Organic Letters_* 4:4395-4398 (2002).
Rajeev et al., "2'-Modified-2-thiothymidine Oligonucleotides" *Org. Lett.* 5(17):3005-3008 (2003).
Reed, "Mechanisms of Apoptosis" *Am. J. Pathol.* 157(5):1415-1430 (2000).
Rubinstein et al., "Recent Advances in Cytokines, Cytokine Receptors and Signal Transduction" *Cytokine Growth Factor Rev.* 9(2):175-181 (1998).
Safar et al., "Molecular studies of prion diseases" *Prog. Brain Res.* 117:421-434 (1998).
Simeoni et al., "Insight into the mechanism of the peptide-based gene delivery system MPG: implications for delivery of siRNA into mammalian cells" *Nucl. Acids Res.* 31(11):2717-2724 (2003).

Sproat et al., "Synthesis of Modified Building Blocks Containing Amino or Thiol Moieties: Application of Modified oligodeoxyribonucleotides" *Nucleosides Nucleotides* 7:651-653 (1988).
Stetler-Stevenson et al., "Tumor Cell Interactions with the Extracellular Matrix During Invasion and Metastasis" *Annu. Rev. Cell Biol.* 9:541-573 (1993).
Stirchak, "Uncharged stereoregular nucleic acid analogs: 2. Morpholino nucleoside oligomers with carbamate internucleoside linkages" *Nucleic Acids Res.* 17:6129-6141 (1989).
Strasser et al., "Apoptosis Signaling" *Annu. Rev. Biochem.* 69:217-245 (2000).
Tae et al., "Efforts toward expansion of the genetic alphabet: replication of DNA with three base pairs" *J. Am. Chem. Soc.* 123:7439-7440 (2001).
Takeda et al.,"Convenient Methods for Syntheses of Active Carbamates, Ureas and Nitrosoureas Using N,N'-disuccinimido Carbonate (DSC)" *Tetrahedron Lett.* 24(42):4569-4572 (1983).
Tittensor, "The Preparation of Nucleoside Carbonates" *J. Chem. Soc.* (*C*), 2656-2662 (1971).
Truffert et al., "Synthesis, Purification and Characterization of Two Peptide-Oligonucleotide Conjugates as Potential Artificial Nucleases" *Tetrahedron* 52(8):3005-3016 (1996).
Valentijn et al., "Solid-phase Synthesis of Lysine-based Cluster Galactosides with High Affinity for the Asialoglycoprotein Receptor" *Tetrahedron* 53:759-770 (1997).
Verma et al., "Modified Oligonucleotides: Synthesis and Strategy for Users" *Annu. Rev. Biochem.* 67:99-134 (1998).
Vives et al., "A Truncated HIV-1 Tat Protein Basic Domain Rapidly Translocates through the Plasma Membrane and Accumulates in the Cell Nucleus" *J. Biol. Chem.* 272(25):16010-16017 (1997).
Weizman et al., "2,2'-Bipyridine ligandoside: a novel building block for modifying DNA with intra-duplex metal complexes" *J. Am. Chem. Soc.* 123:3375-3376 (2001).
Wender et al., "Oligocarbamate Molecular Transporters: Design, Synthesis, and Biological Evaluation of a New Class of Transporters for Drug Delivery" *J. Am. Chem. Soc.* 124:13382-13383 (2002).
Wengel, "Synthesis of 3'- C- and 4' C-Branched Oligodeoxynucleotides and the Development of Locked Nucleic Acid (LNA)" *Acc. Chant. Res.* 32:301-310 (1999).
Wijsman at al., "Solid-support synthesis of di- and tetramannosylated tetrathymidylic acid" *Recl. Trav. Chim. Pays-Bas.* 115:397-401 (1996).
Wilds at al., "Structural basis for recognition of guanosine by a synthetic tricyclic cytosine analogue: Guanidinium G-clamp" *Helvetica Chimica Acta* 86:966-978 (2003).
Wincott at al., "Synthesis, deprotection, analysis and purification of RNA and ribozymes" *Nucleic Acids Res.* 23(14):2677-2684 (1995).
Witzeman et al., "Transacetoacetylation with tert-Butyl Acetoacetate: Synthetic Applications" *J. Org. Chem.* 56:1713-1718 (1991).
Wu at al., "Efforts toward Expansion of the Genetic Alphabet: Optimization of Interbase Hydrophobic Interactions" *J Am. Chem. Soc.* 122:7621-7632 (2000).
Yokota, "Tumor progression and metastasis" *Carcinogenesis* 21:497-503 (2000).
Zhou at al., "Lipophilic polylysines mediate efficient DNA transfection in mammalian cells" *J. of Controlled Release* 19:269-274 (1992).
Zimmerman et al., "Model Studies Directed toward a General Triplex DNA Recognition Scheme: A Novel DNA Base That Binds a CG Base-Pair in an Organic Solvent" *J. Am. Chem. Soc.* 117:10769 10770 (1995).
Zitzmann et al., "Arginine-Glycine-Aspartic Acid (RGD)-Peptide Binds to Both Tumor and Tumor-Endothelial Cells in Vivo" *Cancer Res.* 62:5139-5143 (2002).

\* cited by examiner

LIPOPHILIC CONJUGATED IRNA AGENTS

TECHNICAL FIELD

The invention relates to iRNA agents, which preferably include a monomer in which the ribose moiety has been replaced by a moiety other than ribose. The inclusion of such a monomer can allow for modulation of a property of the iRNA agent into which it is incorporated, e.g., by using the non-ribose moiety as a point to which a ligand or other entity, e.g., a lipophilic moiety. e.g., cholesterol, a bile acid, or a fatty acid conjugate is directly, or indirectly, tethered. The invention also relates to methods of making and using such modified iRNA agents.

BACKGROUND

RNA interference or "RNAi" is a term initially coined by Fire and co-workers to describe the observation that double-stranded RNA (dsRNA) can block gene expression when it is introduced into worms (Fire et al. (1998) *Nature* 391, 806-811). Short dsRNA directs gene-specific, post-transcriptional silencing in many organisms, including vertebrates, and has provided a new tool for studying gene function. RNAi may involve mRNA degradation.

SUMMARY

The inventor has discovered, inter alia, that the ribose sugar of one or more ribonucleotide subunits of an iRNA agent can be replaced with another moiety, e.g., a non-carbohydrate (preferably cyclic) carrier. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The carriers further include (i) at least one "backbone attachment point" (e.g., one or two backbone attachment points) and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" in some embodiments refers to a constituent ring atom of the cyclic carrier, e.g., a carbon atom or a heteroatom (distinct from an atom which provides a backbone attachment point), that connects a selected moiety. The moiety can be, e.g., a ligand, e.g., a targeting or delivery moiety, or a moiety which alters a physical property. One of the most preferred moieties is a moiety which promotes entry into a cell, e.g., a lipophilic moiety, e.g., cholesterol or a fatty acid conjugate. While not wishing to be bound by theory it is believed the attachment of a lipohilic agent increases the lipophilicity of an iRNA agent. Optionally, the selected moiety is connected by an intervening tether to the cyclic carrier. Thus, it will often include a functional group, e.g., an amino group, or generally, provide a bond, that is suitable for incorporation or tethering of another chemical entity, e.g., a ligand to the constituent ring.

Incorporation of one or more RRMSs described herein into an RNA agent, e.g., an iRNA agent, particularly when tethered to an appropriate entity, can confer one or more new properties to the RNA agent and/or alter, enhance or modulate one or more existing properties in the RNA molecule. E.g., it can alter one or more of lipophilicity or nuclease resistance. Incorporation of one or more RRMSs described herein into an iRNA agent can, particularly when the RRMS is tethered to an appropriate entity, modulate, e.g., increase, binding affinity of an iRNA agent to a target mRNA, change the geometry of the duplex form of the iRNA agent, alter distribution or target the iRNA agent to a particular part of the body, or modify the interaction with nucleic acid binding proteins (e.g., during RISC formation and strand separation).

Accordingly, in one aspect, the invention features, an iRNA agent preferably comprising a first strand and a second strand, wherein at least one subunit having a formula (I) is incorporated into at least one of said strands:

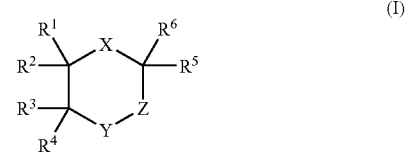

wherein:

X is $N(CO)R^7$, $NR^7$ or $CH_2$;

Y is $NR^8$, O, S, $CR^9R^{10}$, or absent;

Z is $CR^{11}R^{12}$ or absent;

Each of $R^1$, $R^2$, $R^3$, $R^4$, $R^9$, and $R^{10}$ is, independently, H, OH, $OR^a$, $OR^b$, $(CH_2)_nOR^a$, $(CH_2)_nOR^b$, or $(CH_2)_nOH$ provided that at least one of $R^1$, $R^2$, $R^3$, $R^4$, $R^9$, and $R^{10}$ is $OR^a$, $OR^b$, or OH and that at least one of $R^1$, $R^2$, $R^3$, $R^4$, $R^9$, and $R^{10}$ is $(CH_2)_nOR^a$, $(CH_2)_nOR^b$, or $(CH_2)_nOH$ (when the RRMS is terminal, one of $R^1$, $R^2$, $R^3$, $R^4$, $R^9$, and $R^{10}$ will include OH or $OR^a$ and one will include $OR^b$; when the RRMSS is internal, two of $R^1$, $R^2$, $R^3$, $R^4$, $R^9$, and $R^{10}$ will each include an $OR^b$); further provided that preferably OH or $OR^a$ may only be present with $(CH_2)_nOR^b$ and $(CH_2)_nOH$ or $(CH_2)_nOR^a$ may only be present with $OR^b$;

Each of $R^5$, $R^6$, $R^{11}$, and $R^{12}$ is, independently, H, $C_1$-$C_6$ alkyl optionally substituted with 1-3 $R^{13}$, or $C(O)NHR^7$; or $R^5$ and $R^{11}$ together are $C_3$-$C_8$ cycloalkyl optionally substituted with $R^{14}$;

$R^7$ can be a ligand, e.g., $R^7$ can be $R^d$, or $R^7$ can be a ligand tethered indirectly to the carrier, e.g., through a tethering moiety, e.g., $C_1$-$C_{20}$ alkyl substituted with $NR^cR^d$; or $C_1$-$C_{20}$ alkyl substituted with $NHC(O)R^d$;

$R^8$ is $C_1$-$C_6$ alkyl;

$R^{13}$ is hydroxy, $C_1$-$C_4$ alkoxy, or halo;

$R^{14}$ is $NR^cR^7$;

$R^a$ is:

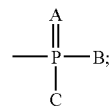

$R^b$ is:

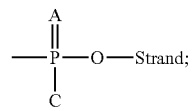

Each of A and C is, independently, O or S;

B is OH, O⁻, or

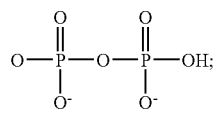

$R^c$ is H or $C_1$-$C_6$ alkyl;
$R^d$ is H or a ligand, e.g., a lipophilic ligand, e.g., cholesterol, a bile acid, a fatty acid or PEG; and
n is 1-4.

Embodiments can include one or more of the following features.

The iRNA agent can be 21 nucleotides in length and there can be a duplex region of about 19 pairs.

The iRNA agent can include a duplex region between 17 and 23 pairs in length.

$R^1$ can be $(CH_2)_nOR^a$ and $R^3$ can be $OR^b$; or $R^1$ can be $(CH_2)_nOR^a$ and $R^9$ can be $OR^b$; or $R^1$ can be $(CH_2)_nOR^a$ and $R^5$ can be $OR^b$; or $R^1$ can be $(CH_2)_nOR^a$ and $R^2$ can be $OR^b$.

$R^1$ can be $(CH_2)_nOH$ and $R^3$ can be $OR^b$; or $R^1$ can be $(CH_2)_nOH$ and $R^9$ can be $OR^b$; or $R^1$ can be $CH_2OH$ and $R^5$ can be $OR^b$; or $R^1$ can be $(CH_2)_nOH$ and $R^2$ can be $OR^b$.

$R^1$ can be $(CH_2)_nOR^b$ and $R^3$ can be $OR^b$; or $R^1$ can be $(CH_2)_nOR^b$ and $R^9$ can be $OR^b$; or $R^1$ can be $(CH_2)_nOR^b$ and $R^5$ can be $OR^b$; or $R^1$ can be $(CH_2)_nOR^b$ and $R^2$ can be $OR^b$; or $R^1$ can be $(CH_2)_nOR^b$ and $R^3$ can be $OR^a$; or $R^1$ can be $(CH_2)_nOR^b$ and $R^9$ can be $OR^a$; or $R^1$ can be $(CH_2)_nOR^b$ and $R^5$ can be $OR^a$; or $R^1$ can be $(CH_2)_nOR$ and $R^2$ can be $OR^a$; or $R^1$ can be $(CH_2)_nOR^b$ and $R^3$ can be OH; or $R^1$ can be $(CH_2)_nOR^b$ and $R^9$ can be OH; or $R^1$ can be $(CH_2)_nOR^b$ and $R^5$ can be OH; or $R^1$ can be $(CH_2)_nOR^b$ and $R^2$ can be OH.

$R^1$ can be $OR^a$ and $R^3$ can be $(CH_2)_nOR^b$; or $R^1$ can be $OR^a$ and $R^9$ can be $(CH_2)_nOR^b$; or $R^1$ can be $OR^a$ and $R^5$ can be $(CH_2)_nOR^b$.

$R^1$ can be OH and $R^3$ can be $(CH_2)_nOR^b$; or $R^1$ can be OH and $R^9$ can be $(CH_2)_nOR^b$; or $R^1$ can be OH and $R^5$ can be $(CH_2)_nOR^b$.

$R^1$ can be $OR^b$ and $R^3$ can be $(CH_2)_nOR^b$; or $R^1$ can be $OR^b$ and $R^9$ can be $(CH_2)_nOR^b$; or $R^1$ can be $OR^b$ and $R^5$ can be $(CH_2)_nOR^b$; or $R^1$ can be $OR^b$ and $R^3$ can be $(CH_2)_nOR^a$; or $R^1$ can be $OR^b$ and $R^9$ can be $(CH_2)_nOR^a$; or $R^1$ can be $OR^b$ and $R^5$ can be $(CH_2)_nOR^a$; or $R^1$ can be $OR^b$ and $R^3$ can be $(CH_2)_nOH$; or $R^1$ can be $OR^b$ and $R^9$ can be $(CH_2)_nOH$; or $R^1$ can be $OR^b$ and $R^5$ can be $(CH_2)_nOH$.

$R^3$ can be $(CH_2)OR^a$ and $R^9$ can be $OR^b$; or $R^3$ can be $(CH_2)_nOR^a$ and $R^9$ can be $OR^b$.

$R^3$ can be $(CH_2)_nOH$ and $R^9$ can be $OR^b$; or $R^3$ can be $(CH_2)_nOH$ and $R^9$ can be $OR^b$.

$R^3$ can be $(CH_2)_nOR^b$ and $R^9$ can be $OR^b$; or can be $(CH_2)_nOR^b$ and $R^9$ can be $OR^b$; or $R^3$ can be $(CH_2)_nOR^b$ and $R^9$ can be $OR^a$; or $R^3$ can be $(CH_2)_nOR^b$ and $R^4$ can be $OR^a$; or $R^3$ can be $(CH_2)_nOR^b$ and $R^9$ can be OH; or $R^3$ can be $(CH_2)_nOR^b$ and $R^4$ can be OH.

$R^3$ can be $OR^b$ and $R^9$ can be $(CH_2)_nOR^b$; or $R^3$ can be $OR^b$ and $R^9$ can be $(CH_2)_nOR^a$; or $R^3$ can be $OR^b$ and $R^9$ can be $(CH_2)_nOR^b$; or $R^3$ can be $OR^b$ and $R^4$ can be $(CH_2)_nOR^b$; or $R^3$ can be $OR^b$ and $R^9$ can be $(CH_2)_nOH$; or $R^3$ can be $OR^b$ and $R^4$ can be $(CH_2)_nOH$.

$R^3$ can be $OR^a$ and $R^9$ can be $(CH_2)_nOR^b$; or $R^3$ can be $OR^a$ and $R^9$ can be $(CH_2)_nOR^b$.

$R^3$ can be OH and $R^9$ can be $(CH_2)_nOR^b$; or $R^3$ can be OH and $R^9$ can be $(CH_2)_nOR^b$.

$R^9$ can be $(CH_2)_nOR^a$ and $R^{10}$ can be $OR^b$.
$R^9$ can be $(CH_2)_nOH$ and $R^{10}$ can be $OR^b$.

$R^9$ can be $(CH_2)_nOR^b$ and $R^{10}$ can be $OR^b$; or $R^9$ can be $(CH_2)_nOR^b$ and $R^{10}$ can be $OR^a$; or $R^9$ can be $(CH_2)_nOR^b$ and $R^{10}$ can be OH.

In some embodiments, at least one of $R^3$, $R^5$ or $R^9$ is OH.

In a preferred embodiment the ribose is replaced with a 4-hydroxyproline-derived scaffold, as shown in formula II.

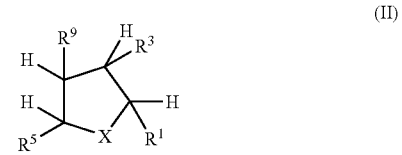

X is $N(CO)R^7$ or $NR^7$, Y is $CR^9R^{10}$, and Z is absent.
n can be 1.
A can be O or S.

$R^1$ can be $CH_2OR^b$ and $R^3$ can be $OR^b$; or $R^1$ can be $CH_2OR^a$ and $R^3$ can be $OR^b$; or $R^1$ can be $CH_2OR^b$ and $R^3$ can be OH; or $R^1$ can be $CH_2OH$ and $R^3$ can be $OR^b$; or $R^1$ can be $CH_2OR^b$ and $R^3$ can be $OR^a$.

$R^1$ and $R^3$ can be cis or $R^1$ and $R^3$ can be trans.

$R^1$ can be $CH_2OR^b$ and $R^9$ can be $OR^a$; or $R^1$ can be $CH_2OR^b$ and $R^9$ can be OH; or $R^1$ can be $CH_2OR^b$ and $R^9$ can be $OR^b$; or $R^1$ can be $CH_2OR^a$ and $R^9$ can be $OR^b$; or $R^1$ can be $CH_2OH$ and $R^9$ can be $OR^b$.

$R^1$ and $R^9$ can be cis or $R^1$ and $R^9$ can be trans.

$R^1$ can be $CH_2OR^b$ and $R^5$ can be $OR^a$; or $R^1$ can be $CH_2OR^b$ and $R^5$ can be OH; or $R^1$ can be $CH_2OR^b$ and $R^5$ can be $OR^b$; or $R^1$ can be $CH_2OR^a$ and $R^5$ can be $OR^b$; or $R^1$ can be $CH_2OH$ and $R^5$ can be $OR^b$.

$R^1$ and $R^5$ can be cis or $R^1$ and $R^5$ can be trans.

$R^7$ can be $(CH_2)_5NHR^d$ or $(CH_2)_5NHR^d$. $R^d$ can be chosen from a folic acid radical; a cholesterol radical; a bile acid radical; a fatty acid radical (e.g., lithocholic-oleyl, lauroyl, docosnyl, stearoyl, palmitoyl, myristoyl, oleoyl, linoleoyl); a carbohydrate radical; a vitamin A radical; a vitamin E radical; a vitamin K radical; polyethylene glycol PEG). Preferably, $R^d$ is a cholesterol radical. In some preferred embodiments, $R^d$ is stearoyl, docosanyl, or lithocholic-oleyl. In some other preferred embodiments, $R^d$ is PEG, e.g. PEG-5K, PEG-20K.

In a further aspect, this invention features an iRNA agent having a first strand and a second strand, wherein at least one subunit having a formula (I) or formula (II) is incorporated into at least one of said strands.

In one aspect, this invention features an iRNA agent having a first strand and a second strand, wherein at least two subunits having a formula (I) or formula (II) are incorporated into at least one of said strands.

In another aspect, this invention provides a method of making an iRNA agent described herein having a first strand and a second strand in which at least one subunit of formula (I) or formula (II) is incorporated in the strands. The method includes contacting the first strand with the second strand.

In a further aspect, this invention provides a method of modulating expression of a target gene, the method includes administering an iRNA agent described herein having a first strand and a second strand in which at least one subunit of formula (I) or formula (II) is incorporated in the strands to a subject.

RRMSs described herein may be incorporated into any single-stranded or double-stranded RNA-like molecule described herein, e.g., an iRNA agent. An iRNA agent may include a duplex comprising a hybridized sense and antisense strand, in which the antisense strand and/or the sense strand may include one or more of the RRMSs described herein. The tethered ligand on different RRMS can be the same or different. An RRMS can be introduced at one or more points in one or both strands of a double-stranded iRNA agent. An RRMS can be placed at or near (within 1, 2, or 3 positions of) the 3' or 5' end of the sense strand or at near (within 1, 2 or 3 positions of) the 3' or 5' end of the antisense strand. In some embodiments it is preferred to not have an RRMS at or near (within 1, 2, or 3 positions of) the 5' end of the antisense strand. An RRMS can be internal, and will preferably be positioned in regions not critical for antisense binding to the target.

In some embodiments, an iRNA agent has an RRMS at 3' end of sense strand and 3' end of antisense strand. In some embodiments, an iRNA agent has an RRMS at 5' end of sense strand and 3' end of antisense strand. In some embodiments, an iRNA agent has an RRMS at 3' end of sense strand and 5' end of antisense strand. In some embodiments, an iRNA agent has an RRMS at 3' end of sense strand and at an internal position in the antisense strand. In some embodiments, an iRNA agent has an RRMS at 5' end of sense strand and at an internal position in the antisense strand. In some embodiments, an iRNA agent has an RRMS at an internal position of sense strand and at 3' end of antisense strand. In some embodiments, an iRNA agent has an RRMS at an internal position of sense strand and at 5' end of antisense strand.

In an embodiment, an iRNA agent may have an RRMS at (or within 1, 2, or 3 positions of) the 3' end of the antisense strand. In an embodiment, an iRNA agent may have an RRMS at (or within 1, 2, or 3 positions of) the 3' end of the antisense strand and at (or within 1, 2, or 3 positions of) the 3' end of the sense strand. In an embodiment, an iRNA agent may have an RRMS at (or within 1, 2, or 3 positions of) the 3' end of the antisense strand and an RRMS at the 5' end of the sense strand, in which both ligands are located at the same end of the iRNA agent.

In certain embodiments, two ligands are tethered, preferably, one on each strand and are hydrophobic moieties. While not wishing to be bound by theory, it is believed that pairing of the hydrophobic ligands can stabilize the iRNA agent via intermolecular van der Waals interactions.

In an embodiment, an iRNA agent may have an RRMS at (or within 1, 2, or 3 positions of) the 3' end of the antisense strand and an RRMS at the 5' end of the sense strand, in which both RRMSs may share the same ligand (e.g., cholic acid) via connection of their individual tethers to separate positions on the ligand. A ligand shared between two proximal RRMSs is referred to herein as a "hairpin ligand."

In other embodiments, an iRNA agent may have an RRMS at one or both of the 3' end and/or 5' end of the sense strand and an RRMS at an internal position of the sense strand. In other embodiments, an iRNA agent may have an RRMS at one or both of the 3' end and/or 5' end of the antisense strand and an RRMS at an internal position of the sense strand. An iRNA agent may have an RRMS at an internal position of the sense strand; or may have an RRMS at an internal position of the antisense strand; or may have an RRMS at an internal position of the sense strand and an RRMS at an internal position of the antisense strand.

In preferred embodiments the iRNA agent includes a first and second sequences, which are preferably two separate molecules as opposed to two sequences located on the same strand, have sufficient complementarity to each other to hybridize (and thereby form a duplex region), e.g., under physiological conditions, e.g., under physiological conditions but not in contact with a helicase or other unwinding enzyme.

It is preferred that the first and second sequences be chosen such that the ds iRNA agent includes a single strand or unpaired region at one or both ends of the molecule. Thus, a ds iRNA agent contains first and second sequences, preferable paired to contain an overhang, e.g., one or two 5' or 3' overhangs but preferably a 3' overhang of 2-3 nucleotides. Most embodiments will have a 3' overhang. Preferred sRNA agents will have single-stranded overhangs, preferably 3' overhangs, of 1 or preferably 2 or 3 nucleotides in length at each end. The overhangs can be the result of one strand being longer than the other, or the result of two strands of the same length being staggered. 5' ends are preferably phosphorylated.

Other modifications to sugars, bases, or backbones described herein can be incorporated into the iRNA agents.

The iRNA agents can take an architecture or structure described herein. The iRNA agents can be palindromic, or double targeting, as described herein.

The iRNA agents can have a sequence such that a non-cannonical or other than cannonical Watson-Crick structure is formed between two monomers of the iRNA agent or between a strand of the iRNA agent and another sequence, e.g., a target or off-target sequence, as is described herein.

The iRNA agent can be selected to target any of a broad spectrum of genes, including any of the genes described herein.

In a preferred embodiment the iRNA agent has an architecture (architecture refers to one or more of overall length, length of a duplex region, the presence, number, location, or length of overhangs, single strand versus double strand form) described herein. E.g., the iRNA agent can be less than 30 nucleotides in length, e.g., 21-23 nucleotides. Preferably, the iRNA is 21 nucleotides in length and there is a duplex region of about 19 pairs. In one embodiment, the iRNA is 21 nucleotides in length, and the duplex region of the iRNA is 19 nucleotides. In another embodiment, the iRNA is greater than 30 nucleotides in length.

In some embodiment the duplex region of the iRNA agent will have, mismatches. Preferably it will have no more than 1, 2, 3, 4, or 5 bases, which do not form canonical Watson-Crick pairs or which do not hybridize. Overhangs are discussed in detail elsewhere herein but are preferably about 2 nucleotides in length. The overhangs can be complementary to the gene sequences being targeted or can be other sequence. TT is a preferred overhang sequence. The first and second iRNA agent sequences can also be joined, e.g., by additional bases to form a hairpin, or by other non-base linkers.

In addition to the RRMS-containing bases the iRNA agents described herein can include nuclease resistant monomers (NRMs).

In another aspect, the invention features an iRNA agent to which is conjugated a lipophilic moiety, e.g., cholesterol, a bile acid, or a fatty acid; (e.g., lithocholic-oleyl, lauroyl, docosnyl, stearoyl, palmitoyl, myristoyl, oleoyl, linoleoyl, dodecanoyl, lithocholyl, 5β-cholanyl, N,N-distearyl-lithocholamide, 1,2-di-O-stearoylglyceride); e.g., by conjugation to an RRMS of an iRNA agent. In a preferred embodiment, the lipophilic moiety enhances entry of the iRNA agent into a cell. In a preferred embodiment, the cell is part of an organism, tissue, or cell line, e.g., a primary cell line, immortalized cell line, or any type of cell line disclosed herein. Thus, the conjugated iRNA agent can be used to silence a target gene in an organism, e.g., a mammal, e.g., a human, or to silence a target gene in a cell line or in cells which are outside an organism.

The lipophilic moiety can be chosen, for example, from the group consisting of a lipid, cholesterol, oleyl, retinyl, cholesteryl residues, cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid (i.e., palmitoyl), myristic acid (i.e., myristoyl), O3-(oleoyl)lithocholic acid, O3-(oleoyl)cholenic acid, lauroyl, docosnyl, stearoyl, oleoyl, linoleoyl, dimethoxytrityl, or phenoxazine. A preferred lipophilic moiety is cholesterol. In some embodiments, a preferred lipophilic moiety is stearoyl, docosanyl, or lithocholic-oleyl. The lipophilic moieties described herein are conjugated to the RRMS, for example, via a tether. When used herein, terms to describe the lipophilic moiety such as a free acid (such as a free fatty acid, e.g., palmitic acid) are used interchangeably with the radical term (e.g., palmitoyl) for the conjugated form of the lipophilic moiety.

The iRNA agent can have a first strand and a second strand, wherein at least one subunit having formula (I) or formula (II) is incorporated into at least one of the strands. The iRNA agent can have one or more of any of the features described herein. For example, when the subunit is of formula (I), $R^d$ can be cholesterol; X can be $N(CO)R^7$ or $NR^7$, Y can be $CR^9R^{10}$, and Z can be absent, and $R^1$ can be $(CH_2)_nOR^b$ and $R^3$ can be $OR^a$ or OH; X can be $N(CO)R^7$ or $NR^7$, Y can be $CR^9R^{10}$, and Z can be $CR^{11}R^{12}$, and $R^9$ can be $(CH_2)\%OR^b$ and $R^{10}$ can be $OR^a$ or OH; X can be $N(CO)R^7$ or $NR^7$, Y can be $NR^8$, and Z can be $CRR^{11}R^{12}$, and $R^1$ can be $(CH_2)_nOR^b$ and $R^3$ can be $OR^a$ or OH; X can be $CH_2$; Y can be $CR^9R^{10}$; and Z can be $CR^{11}R^{12}$, in which $R^6$ can be $C(O)NHR^7$; or X can be $CH_2$; Y can be $CR^9R^{10}$; and Z can be $CR^{11}R^{12}$ in which $R^{11}$ or $R^{12}$ can be $C(O)NHR^7$ or $R^5$ and $R^{11}$ together can be $C_5$ or $C_6$ cycloalkyl substituted with $N(CH_3)R^7$.

In a preferred embodiment, the invention provides methods of silencing a target gene by providing an iRNA agent to which a lipophilic moiety is conjugated, e.g., a lipophilic conjugated iRNA agent described herein, to a cell. In a preferred embodiment the conjugated iRNA agent an be used to silence a target gene in an organism, e.g., a mammal, e.g., a human, or to silence a target gene in a cell line or in cells which are outside an organism.

In another aspect, the invention provides compositions of iRNA agents described herein, and in particular compositions of an iRNA agent to which a lipophilic moiety is conjugated, e.g., a lipophilic conjugated iRNA agent described herein. In a preferred embodiment the composition is a pharmaceutically acceptable composition.

The methods and compositions of the invention, e.g., the RRSM-containing iRNA agents described herein, can be used with any of the iRNA agents described herein. In addition, the methods and compositions of the invention can be used for the treatment of any disease or disorder described herein, and for the treatment of any subject, e.g., any animal, any mammal, such as any human.

The non-ribose scaffolds, as well as monomers and dimers of the RRMSs described herein are within the invention An "RNA agent" as used herein, is an unmodified RNA, modified RNA, or nucleoside surrogate, all of which are defined herein, see the section herein entitled RNA Agents. While numerous modified RNAs and nucleoside surrogates are described herein, preferred examples include those which include one or more RRMS. Preferred examples are those which also a 2' sugar modification, a modification in a single strand overhang, preferably a 3' single strand overhang, or, particularly if single stranded, a 5' modification which includes one or more phosphate groups or one or more analogs of a phosphate group.

An "iRNA agent" as used herein, is an RNA agent which can, or which can be cleaved into an RNA agent which can, down regulate the expression of a target gene, preferably an endogenous or pathogen target RNA. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can include a single strand or can include more than one strands, e.g., it can be a double stranded iRNA agent. If the iRNA agent is a single strand it is particularly preferred that it include a 5' modification which includes one or more phosphate groups or one or more analogs of a phosphate group.

The details of one or more embodiments of the invention are set forth in the accompanying drawings and the description below. Other features and advantages of the invention will be apparent from the description and drawings, and from the claims. This application incorporates all cited references, patents, and patent applications by references in their entirety for all purposes.

DETAILED DESCRIPTION

Double-stranded (dsRNA) directs the sequence-specific silencing of mRNA through a process known as RNA interference (RNAi). The process occurs in a wide variety of organisms, including mammals and other vertebrates.

It has been demonstrated that 21-23 nt fragments of dsRNA are sequence-specific mediators of RNA silencing, e.g., by causing RNA degradation. While not wishing to be bound by theory, it may be that a molecular signal, which may be merely the specific length of the fragments, present in these 21-23 nt fragments recruits cellular factors that mediate RNAi. Described herein are methods for preparing and administering these 21-23 nt fragments, and other iRNAs agents, and their use for specifically inactivating gene function. The use of iRNAs agents (or recombinantly produced or chemically synthesized oligonucleotides of the same or similar nature) enables the targeting of specific mRNAs for silencing in mammalian cells. In addition, longer dsRNA agent fragments can also be used.

Ligand-Conjugated Monomer Subunits and Monomers for Oligonucleotide Synthesis

Definitions

The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The terms "adeninyl, cytosinyl, guaninyl, thyminyl, and uracilyl" and the like refer to radicals of adenine, cytosine, guanine, thymine, and uracil.

A "protected" moiety refers to a reactive functional group, e.g., a hydroxyl group or an amino group, or a class of molecules, e.g., sugars, having one or more functional groups, in which the reactivity of the functional group is temporarily blocked by the presence of an attached protecting group. Protecting groups useful for the monomers and methods described herein can be found, e.g., in Greene, T. W., *Protective Groups in Organic Synthesis* (John Wiley and Sons: New York), 1981, which is hereby incorporated by reference.

General

Figure 1:
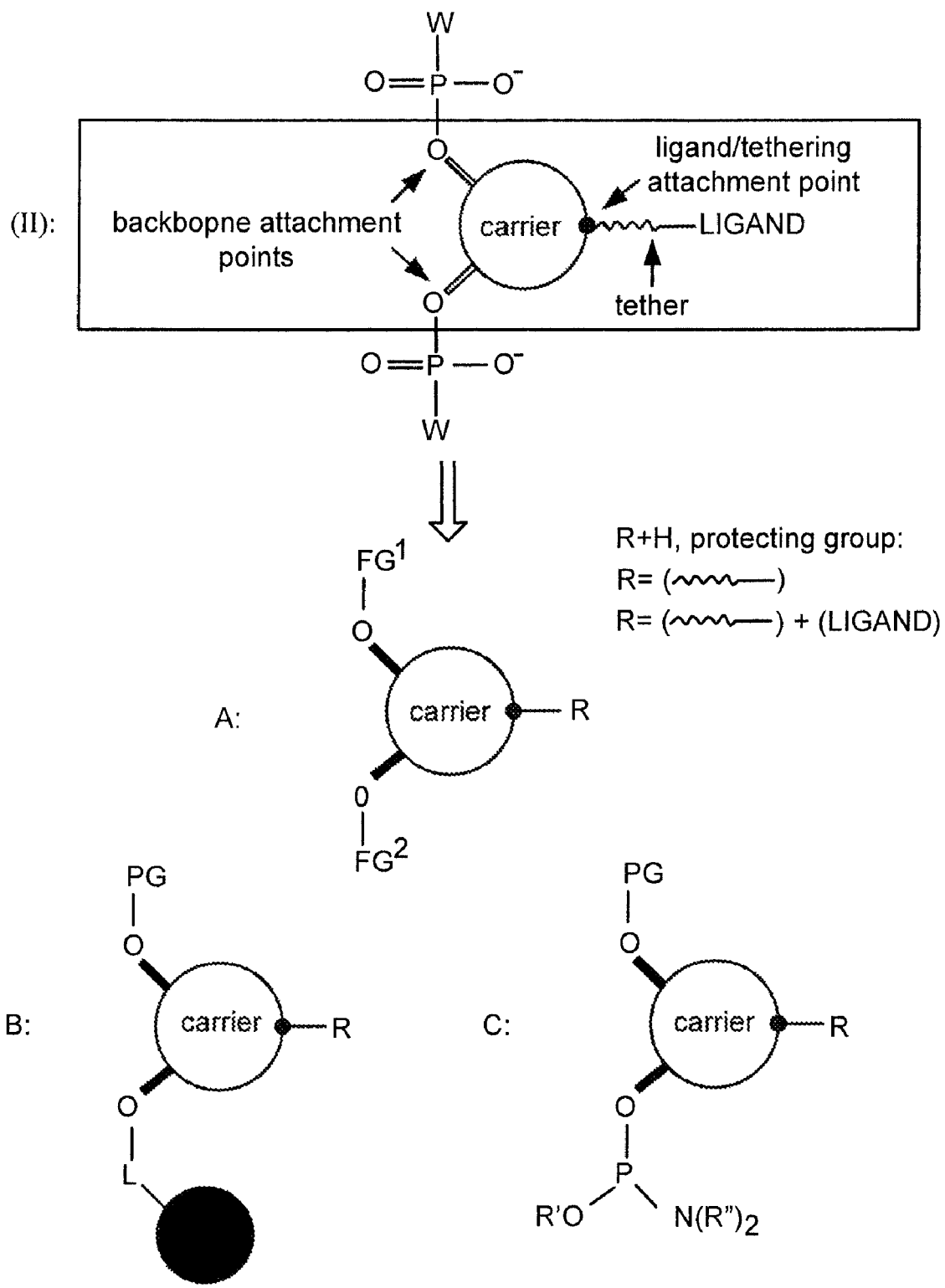
FIG. 1 a general synthetic scheme for incorporation of RRMS monomers into an oligonucleotide.

An RNA agent, e.g., an iRNA agent containing a preferred, but nonlimiting ligand-conjugated monomer subunit, is presented as formula (II) below and in the scheme in FIG. 1. The carrier (also referred to in some embodiments as a "linker") can be a cyclic or acyclic moiety and include one or two "backbone attachment points" (e.g., hydroxyl groups) and a ligand. The ligand can be directly attached (e.g., conjugated) to the carrier or indirectly attached (e.g., conjugated) to the carrier by an intervening tether (e.g., an acyclic chain of one or more atoms; or a nucleobase, e.g., a naturally occurring nucleobase optionally having one or more chemical modifications, e.g., an unusual base; or a universal base). The carrier therefore also includes a "ligand or tethering

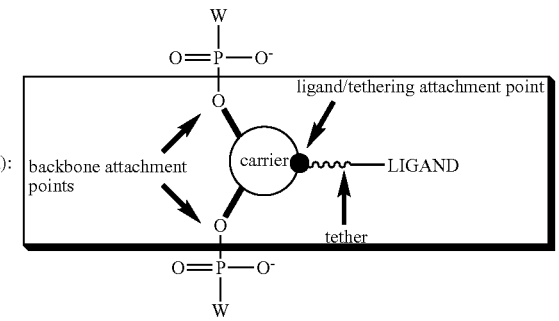

attachment point" for the ligand and tether/tethered ligand, respectively.

The ligand-conjugated monomer subunit may be the 5' or 3' terminal subunit of the RNA molecule, i.e., one of the two —P(O)(O⁻)W groups may be a hydroxyl group, and the "W" of the other —P(O)(O⁻)W group may be a chain of two or more unmodified or modified ribonucleotides. Alternatively, the ligand-conjugated monomer subunit may occupy an internal position, and both "W" groups may be one or more unmodified or modified ribonucleotides. More than one ligand-conjugated monomer subunit may be present in a RNA molecule, e.g., an iRNA agent. Preferred positions for inclusion of a tethered ligand-conjugated monomer subunits, e.g., one in which a lipophilic moiety, e.g., cholesterol, a bile acid radical, or a fatty acid conjugate radical (e.g., lithocholic-oleyl, lauroyl, docosnyl, stearoyl, palmitoyl, myristoyl oleoyl, linoleoyl) is tethered to the carrier are at the 3' terminus, the 5' terminus, or an internal position of the sense strand.

The modified RNA molecule of formulas (II) can be obtained using oligonucleotide synthetic methods known in the art. In a preferred embodiment, the modified RNA molecule of formula (II) can be prepared by incorporating one or more of the corresponding monomer compounds (see, e.g., A, B, and C below and in the scheme in FIG. 1) into a growing sense or antisense strand, utilizing, e.g., phosphoramidite or H-phosphonate coupling strategies.

The monomers, e.g., a ligand-conjugated monomer, generally include two differently functionalized hydroxyl groups ($OFG^1$ and $OFG^2$), which are linked to the carrier molecule (see A below and in FIG. 1), and a ligand/tethering attachment point. As used herein, the term "functionalized hydroxyl group" means that the hydroxyl proton has optionally been replaced by another substituent. In some embodiments, the functionalized hydroxyl group (OFG) is simply an OH, for example a deprotected OH group. As shown in representative structures B and C below and in FIG. 1, one hydroxyl group ($OFG^1$) on the carrier is functionalized with a protecting group (PG). The other hydroxyl group ($OFG^2$) can be functionalized with either (1) a liquid or solid phase synthesis support reagent (solid circle) directly or indirectly through a linker, L, as in B, or (2) a phosphorus-containing moiety, e.g., a phosphoramidite as in C. The tethering attachment point may be connected to a hydrogen atom, a suitable protecting group, a tether, or a tethered ligand at the time that the monomer is incorporated into the growing sense or antisense strand (see variable "R" in A below). Thus, the tethered ligand can be, but need not be attached to the monomer at the time that the monomer is incorporated into the growing strand. In certain embodiments, the tether, the ligand or the tethered ligand may be linked to a "precursor" ligand-conjugated monomer subunit after a "precursor" ligand-conjugated monomer subunit has been incorporated into the strand. The wavy line used below (and elsewhere herein) refers to a connection, and can represent a direct bond between the moiety and the attachment point or a tethering molecule which is interposed between the moiety and the attachment point. Directly tethered means the moiety is bound directly to the attachment point. Indirectly tethered means that there is a tether molecule interposed between the attachment point and the moiety.

The OFG protecting group may be selected as desired, e.g., from T. W. Greene and P. G. M. Wuts, *Protective Groups in Organic Synthesis*, 2d. Ed., John Wiley and Sons (1991). The protecting group is preferably stable under amidite synthesis conditions, storage conditions, and oligonucleotide synthesis conditions.

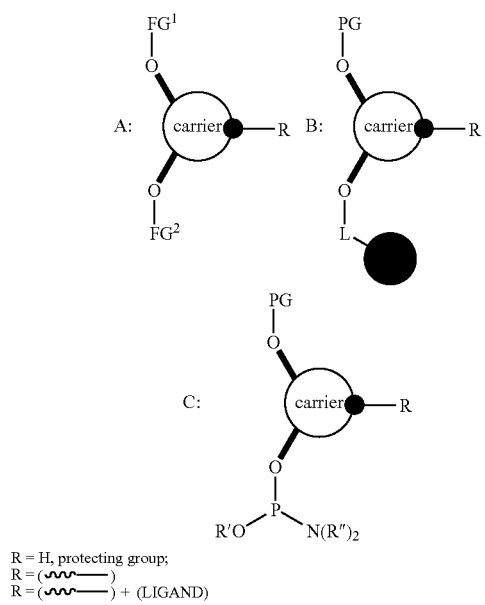

R = H, protecting group;
R = (∿∿——)
R = (∿∿——) + (LIGAND)

Tethered Ligands

A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Preferred moieties are ligands, which are coupled, preferably covalently, either directly or indirectly via an intervening tether, to the carrier. In preferred embodiments, the ligand is attached to the carrier via an intervening tether. As discussed above, the ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., carrier-$(CH_2)_n NH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an iRNA agent into which it is incorporated. In preferred embodiments a ligand provides an enhanced affinity for a selected target, e.g, molecule, cell or cell type, compartment, e.g., a cellular or organ compartment, tissue, organ or region of the body, as, e.g., compared to a species absent such a ligand.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids (e.g., cholesterol, a bile acid, or a fatty acid (e.g., lithocholic-oleyl, lauroyl, docosnyl, stearoyl, palmitoyl, myristoyl oleoyl, linoleoyl), steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics.

The ligand may also be a recombinant or synthetic molecule, such as a synthetic polymer, e.g., polyethylene glycol (PEG), PEG-40K, PEG-20K and PEG-5K.

Other examples of ligands include lipophilic molecules, e.g, cholesterol, cholic acid, adamantane acetic acid, 1-pyrene butyric acid, dihydrotestosterone, glycerol (e.g., esters and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., lauroyl, docosnyl, stearoyl, oleoyl, linoleoyl 1,3-bis-O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dodecanoyl, lithocholyl, 5β-cholanyl, N,N-distearyl-lithocholamide, 1,2-di-O-stearoylglyceride, dimethoxytrityl, or phenoxazine) and PEG (e.g., PEG-5K, PEG-20K, PEG-40K).

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

The iRNA agents of the invention are particularly useful when targeted to the liver. An iRNA agent can be targeted to the liver by incorporation of a monomore derivitzed with a ligand which targets to the liver. For example, a liver-targeting agent can be a lipophilic moiety. Preferred lipophilic moieties include lipid, cholesterols, oleyl, retinyl, or cholesteryl residues. Other lipophilic moieties that can function as liver-targeting agents include cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, oleoylic acid, linoleoylic acid, O3-(oleoyl)lithocholic acid, O3-(oleoyl)cholenic acid, dimethoxytrityl, lauroylic acid, docosynylic acid, stearoylic acid, or phenoxazine. In some embodiments, a preferred lipophilic moiety is stearoyl, docosanyl, or lithocholic-oleyl.

An iRNA agent can also be targeted to the liver by association with a lipoprotein such as HDL or LDL, e.g., lactosylated LDL. Polymeric carriers complexed with sugar residues can also function to target iRNA agents to the liver.

Exemplary Ligand Conjugated Monomers line-based RRMS which is at the 3' terminus, the 5'terminus, or internal, in the sense strand. The attachment can be direct or through a tethering molecule. Tethers, spacers or linkers discussed herein can be used to attach the moiety to the RRMS.

1.

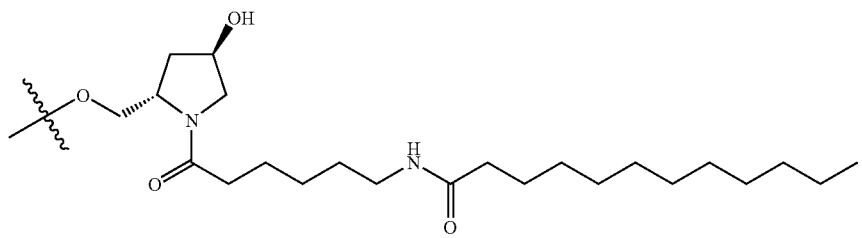

2.

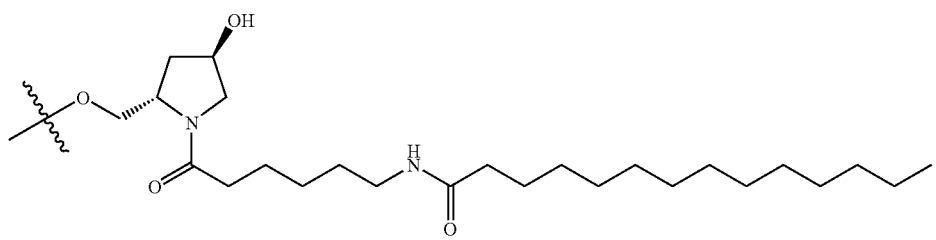

3.

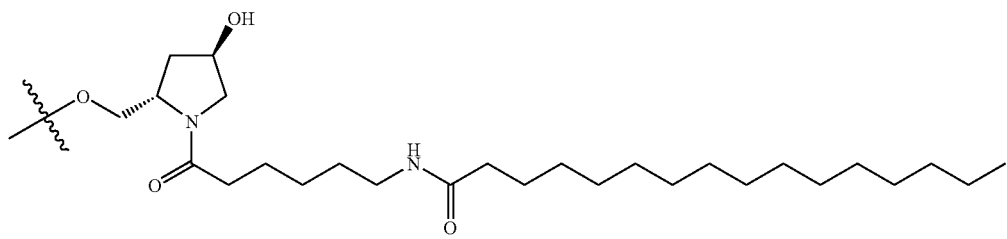

4.

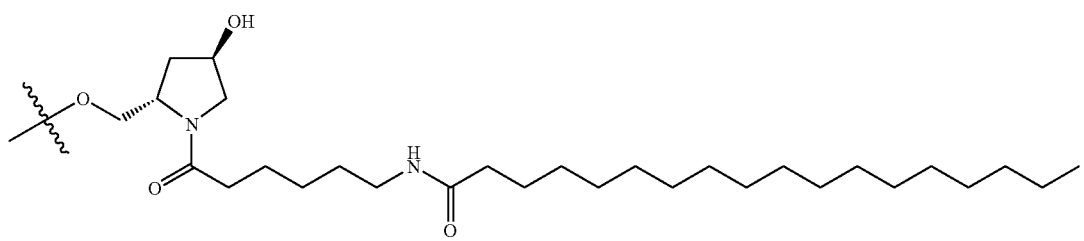

5.

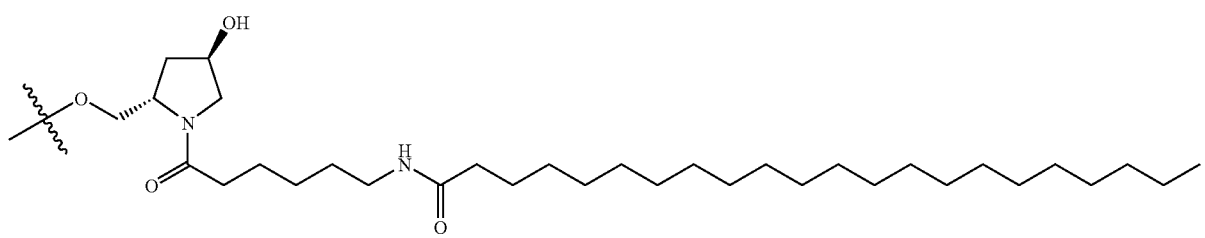

Figure 2:
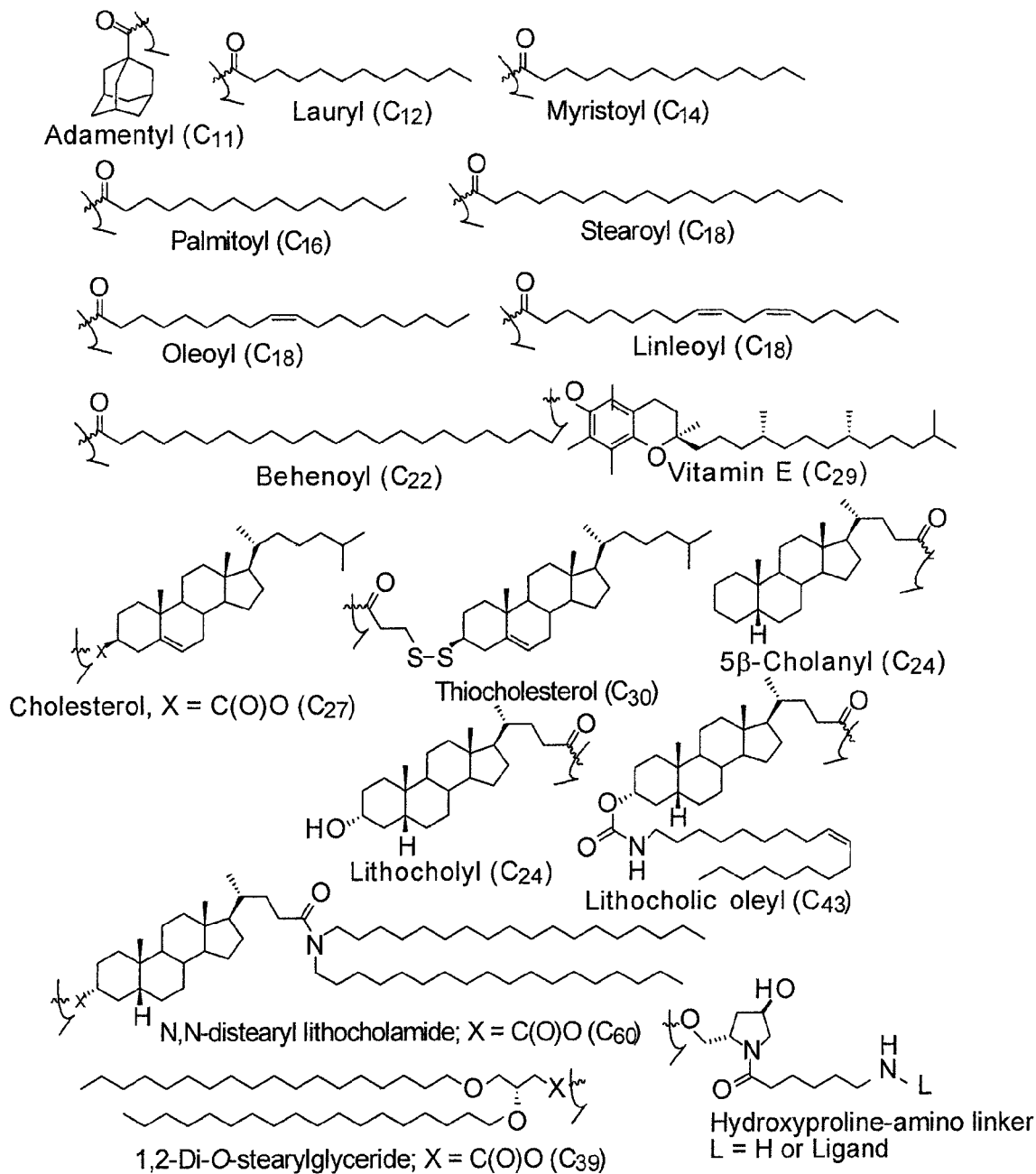
FIG. 2 is a representation of structures of lipophilic ligands and a hydroxyproline-amino linker conjugated to siRNA.

Exemplary structures of lipophilic ligand and Hydroxyproline-amino linker conjugated to siRNA are provided in FIG. 2.

The lipophilic moiety can be attached at the 3' terminus, the 5'terminus, or internally, preferably on the sense strand. The lipohilic moiety can be attached to an RRMS, e.g., a pyrroiRNA Agent Structure The monomers described herein can be used to make oligonucleotides which are useful as iRNA agents, e.g., RNA molecules, (double-stranded; single-stranded) that mediate RNAi, e.g., with respect to an endogenous gene of a subject or to a gene of a pathogen. In most cases the iRNA agent will incorporate monomers described herein together with naturally occurring nucleosides or nucleotides or with other modified nucleosides or nucleotides. The modified monomers can be present at any position in the iRNA agent, e.g., at the termini or in the middle region of an iRNA agent or in a duplex region or in an unpaired region. In a preferred embodiment iRNA agent can have any architecture, e.g., architecture described herein. E.g., it can be incorporated into an iRNA agent having an overhang structure, a hairpin or other single strand structure or a two-strand structure, as described herein.

The RRMS-containing iRNA agent should include a region of sufficient homology to the target gene, and be of sufficient length in terms of nucleotides, such that the iRNA agent, or a fragment thereof, can mediate down regulation of the target gene. (For ease of exposition the term nucleotide or ribonucleotide is sometimes used herein in reference to one or more monomeric subunits of an RNA agent. It will be understood herein that the usage of the term "ribonucleotide" or "nucleotide", herein can, in the case of a modified RNA or nucleotide surrogate, also refer to a modified nucleotide, or surrogate replacement moiety at one or more positions.) Thus, the iRNA agent is or includes a region which is at least partially, and in some embodiments fully, complementary to the target RNA. It is not necessary that there be perfect complementarity between the iRNA agent and the target, but the correspondence must be sufficient to enable the iRNA agent, or a cleavage product thereof, to direct sequence specific silencing, e.g., by RNAi cleavage of the target RNA, e.g., mRNA.

In addition to homology to target RNA and the ability to down regulate a target gene, an iRNA agent will preferably have one or more of the following properties:

(1) if single stranded it will have a 5' modification which includes one or more phosphate groups or one or more analogs of a phosphate group;

(2) it will, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA;

(3) it will, despite modifications, even to a very large number, or all of the nucleosides, still have "RNA-like" properties, i.e., it will possess the overall structural, chemical and physical properties of an RNA molecule, even though not exclusively, or even partly, of ribonucleotide-based content. For example, an iRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_{3'}$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. (Generally, it is preferred that a modified moiety at the 2' sugar position will be able to enter into H-bonding which is more characteristic of the OH moiety of a ribonucleotide than the H moiety of a deoxyribonucleotide. A preferred iRNA agent will: exhibit a $C_{3'}$-endo pucker in all, or at least 50, 75, 80, 85, 90, or 95% of its sugars; exhibit a $C_{3'}$-endo pucker in a sufficient amount of its sugars that it can give rise to a the RNA-characteristic A-family-type helix; will have no more than 20, 10, 5, 4, 3, 2, or 1 sugar which is not a $C_{3'}$-endo pucker structure. These limitations are particularly preferably in the antisense strand;

(4) regardless of the nature of the modification, and even though the RNA agent can contain deoxynucleotides or modified deoxynucleotides, particularly in overhang or other single strand regions, it is preferred that DNA molecules, or any molecule in which more than 50, 60, or 70% of the nucleotides in the molecule, or more than 50, 60, or 70% of the nucleotides in a duplexed region are deoxyribonucleotides, or modified deoxyribonucleotides which are deoxy at the 2' position, are excluded from the definition of RNA agent.

A "double stranded (ds) iRNA agent" as used herein, is an iRNA agent which includes more than one, and preferably two, strands in which interchain hybridization can form a region of duplex structure.

The antisense strand of a double stranded iRNA agent should be equal to or at least, 14, 15, 16, 17, 18, 19, 25, 29, 40, or 60 nucleotides in length. It should be equal to or less than 200, 100, or 50, nucleotides in length. Preferred ranges are 17 to 25, 19 to 23, and 19 to 21 nucleotides in length.

The sense strand of a double stranded iRNA agent should be equal to or at least 14, 15, 16, 17, 18, 19, 25, 29, 40, or 60 nucleotides in length. It should be equal to or less than 200, 100, or 50, nucleotides in length. Preferred ranges are 17 to 25, 19 to 23, and 19 to 21 nucleotides in length.

The double strand portion of a double stranded iRNA agent should be equal to or at least, 14, 15, 16, 17, 18, 19, 20, 21, 22, 23, 24, 25, 29, 40, or 60 nucleotide pairs in length. It should be equal to or less than 200, 100, or 50, nucleotides pairs in length. Preferred ranges are 15-30, 17 to 23, 19 to 23, and 19 to 21 nucleotides pairs in length.

In many embodiments, the ds iRNA agent is sufficiently large that it can be cleaved by an endogenous molecule, e.g., by Dicer, to produce smaller ds iRNA agents, e.g., sRNAs agents It may be desirable to modify one or both of the antisense and sense strands of a double strand iRNA agent. In some cases they will have the same modification or the same class of modification but in other cases the sense and antisense strand will have different modifications, e.g., in some cases it is desirable to modify only the sense strand. It may be desirable to modify only the sense strand, e.g., to inactivate it, e.g., the sense strand can be modified in order to inactivate the sense strand and prevent formation of an active sRNA/protein or RISC.

It is preferred that the sense and antisense strands be chosen such that the ds iRNA agent includes a single strand or unpaired region at one or both ends of the molecule. Thus, a ds iRNA agent contains sense and antisense strands, preferable paired to contain an overhang, e.g., one or two 5' or 3' overhangs but preferably a 3' overhang of 2-3 nucleotides. Most embodiments will have a 3' overhang. Preferred sRNA agents will have single-stranded overhangs, preferably 3' overhangs, of 1 or preferably 2 or 3 nucleotides in length at each end. The overhangs can be the result of one strand being longer than the other, or the result of two strands of the same length being staggered. 5' ends are preferably phosphorylated. Preferred lengths for the duplexed region is between 15 and 30, most preferably 18, 19, 20, 21, 22, and 23 nucleotides in length.

The isolated iRNA agents described herein, including ds iRNA agents and sRNA agents can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the term "oligonucleotide" refers to a nucleic acid molecule (RNA or DNA) preferably of length less than 100, 200, 300, or 400 nucleotides.

RNA agents discussed herein include otherwise unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) Summary: the modified nucleosides of RNA, Nucleic Acids Res. 22: 2183-2196. Such rare or unusual RNAs, often termed modified RNAs (apparently because the are typically the result of a post transcriptionally modification) are within the term unmodified RNA, as used herein. Modified RNA as used herein refers to a molecule in which one or more of the components of the nucleic acid, namely sugars, bases, and phosphate moieties, are different from that which occur in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone.

Much of the discussion below refers to single strand molecules. In many embodiments of the invention a double stranded iRNA agent, e.g., a partially double stranded iRNA agent, is required or preferred. Thus, it is understood that that double stranded structures (e.g. where two separate molecules are contacted to form the double stranded region or where the double stranded region is formed by intramolecular pairing (e.g., a hairpin structure)) made of the single stranded structures described below are within the invention. Preferred lengths are described elsewhere herein.

As nucleic acids are polymers of subunits or monomers, many of the modifications described below occur at a position which is repeated within a nucleic acid, e.g., a modification of a base, or a phosphate moiety, or the a non-linking O of a phosphate moiety. In some cases the modification will occur at all of the subject positions in the nucleic acid but in many, and infact in most cases it will not. By way of example, a modification may only occur at a 3' or 5' terminal position, may only occur in a terminal regions, e.g. at a position on a terminal nucleotide or in the last 2, 3, 4, 5, or nucleotides of a strand. A modification may occur in a double strand region, a single strand region, or in both. A modification may occur only in the double strand region of an RNA or may only occur in a single strand region of an RNA. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

Exemplary modification include the following:

(a) backbone modifications, e.g., modification of a backbone P, including replacement of P with S, or P substituted with alkyl or allyl, e.g., Me, and dithioates (S—P=S); these modifications can be used to promote nuclease resistance;

(b) 2'-O alkyl, e.g., 2'-OMe, 3'-O alkyl, e.g., 3'-OMe (at terminal and/or internal positions); these modifications can be used to promote nuclease resistance or to enhance binding of the sense to the antisense strand, the 3' modifications can be used at the 5' end of the sense strand to avoid sense strand activation by RISC;

(c) 2'-5' linkages (with 2'-H, 2'-OH and 2'-OMe and with P=O or P=S) these modifications can be used to promote nuclease resistance or to inhibit binding of the sense to the antisense strand, or can be used at the 5' end of the sense strand to avoid sense strand activation by RISC;

(d) L sugars (e.g., L ribose, L-arabinose with 2'-H, 2'-OH and 2'-OMe); these modifications can be used to promote nuclease resistance or to inhibit binding of the sense to the antisense strand, or can be used at the 5' end of the sense strand to avoid sense strand activation by RISC;

(e) modified sugars (e.g., locked nucleic acids (LNA's), hexose nucleic acids (HNA's) and cyclohexene nucleic acids (CeNA's)); these modifications can be used to promote nuclease resistance or to inhibit binding of the sense to the antisense strand, or can be used at the 5' end of the sense strand to avoid sense strand activation by RISC;

(f) nucleobase modifications (e.g., C-5 modified pyrimidines, N-2 modified purines, N-7 modified purines, N-6 modified purines), these modifications can be used to promote nuclease resistance or to enhance binding of the sense to the antisense strand;

(g) cationic groups and Zwitterionic groups (preferably at a terminus), these modifications can be used to promote nuclease resistance;

(h) conjugate groups (preferably at terminal positions), e.g., naproxen, biotin, a lipophilic moiety such as cholesterol, a bile acid, or a fatty acid conjugate, ibuprofen, folic acid, peptides, and carbohydrates; these modifications can be used to promote nuclease resistance or to target the molecule, or can be used at the 5' end of the sense strand to avoid sense strand activation by RISC. The invention is further illustrated by the following examples, which should not be construed as further limiting.

EXAMPLES

Example 1

Synthesis of Lipophilic Conjugate Building Blocks

The amino derivative 100 was synthesized by Pd/C mediated hydrogenation of Cbz group and used as such with out any further purification (Scheme 1). All the lipid derivatives (102a-k) were prepared by the reaction of acid and amine with HBTU in the presence of DIEA in a mixture of DCM/DMF. All the hydroxyl derivatives (102a-k) were converted to the corresponding succinate by the reaction of succinic anhydride and DMAP in DCM and it was loaded on to Long chain alkyl amine-CPG using the HBTU/DIEA peptide coupling method or PPh$_3$/DMAP/DTNP method (Scheme 2).

Synthesis of 6-amino-1-{2-[bis-(4-methoxy-phenyl)-phenyl-methoxymethyl]-4-hydroxy-pyrrolidin-1-yl}-hexan-1-one 100

The Cbz protected amine 100 (33.56 g, 50.33 mmol) was dissolved in a mixture of MeOH/Ethyl acetate (1:8, 250 mL) and degassed with argon. Pd/C (3.3 g, 10 wt % Degussa wet type) was added and degassed and purged with hydrogen. The mixture was stirred under hydrogen (Balloon pressure) for 7 hrs. Reaction was monitored by TLC (10% MeOH/DCM, PMA stain). The TLC of the reaction mixture showed the complete disappearance of the starting Cbz protected amine. The reaction mixture was filtered through a pad of celite, washed with EtOAc (100 mL) and the combined filtrates were concentrated. The residue was dried under high vacuum overnight to provide the product as a foam (26.8 g). It was directly used for the next reaction with out further purification. $^1$H NMR (DMSO-$d_6$, 400 MHz) δ=7.36-7.24 (m, 4H), 7.23-7.15 (m, 5H), 6.92-6.82 (m, 4H), 4.40 (m, 0.7H), 4.29 (m, 0.3H), 4.20-4.08 (m, 1H), 3.71 (s, 6H), 3.62-3.42 (m, 1H), 3.36-3.14 (m, 2H), 3.04-2.96 (m, 2H), 2.56-2.44 (m, 2H), 2.24-2.10 (m, 2H), 2.16-1.80 (m, 3H) 1.54-1.05 (m, 7H). $^{13}$C NMR DMSO-$d_6$) 171.06, 170.94, 158.11, 157.99, 145.11, 144.79, 135.87, 135.76, 135.50, 135.42, 129.61, 129.58, 128.88, 128.19, 127.88, 127.77, 127.59, 126.74, 126.58, 125.30, 113.19, 113.09, 85.78, 85.12, 79.20, 68.58, 67.45, 65.23, 63.36, 59.76, 55.60, 55.05, 55.01, 54.98, 54.91, 53.46, 41.52, 38.04, 36.31, 34.25, 33.17, 32.60, 26.22, 26.17, 24.77, 24.41, 22.61, 21.03, 20.74, 14.07. MS. Molecular weight calculated for $C_{32}H_{40}N_2O_5$, Cal. 532.67, Found

Scheme 1

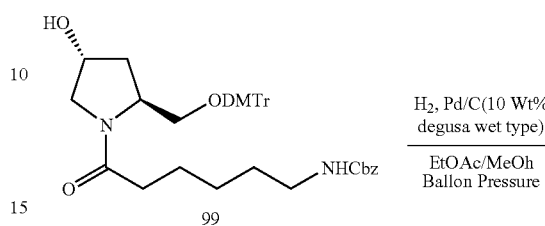

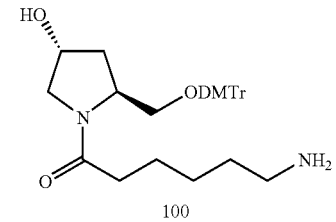

Scheme 2

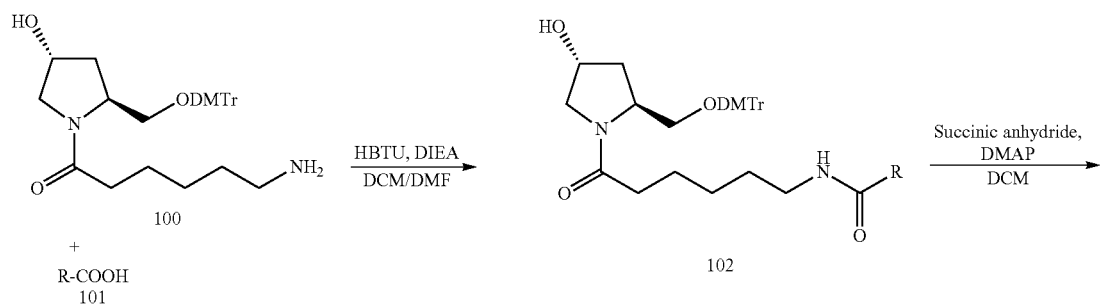

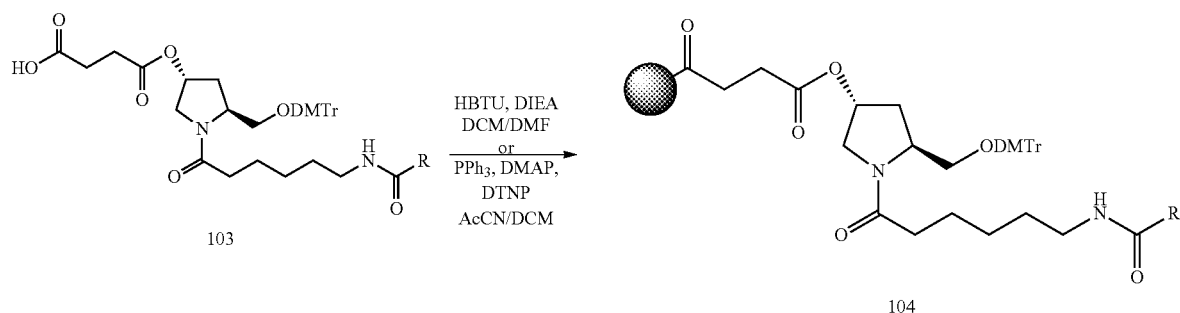

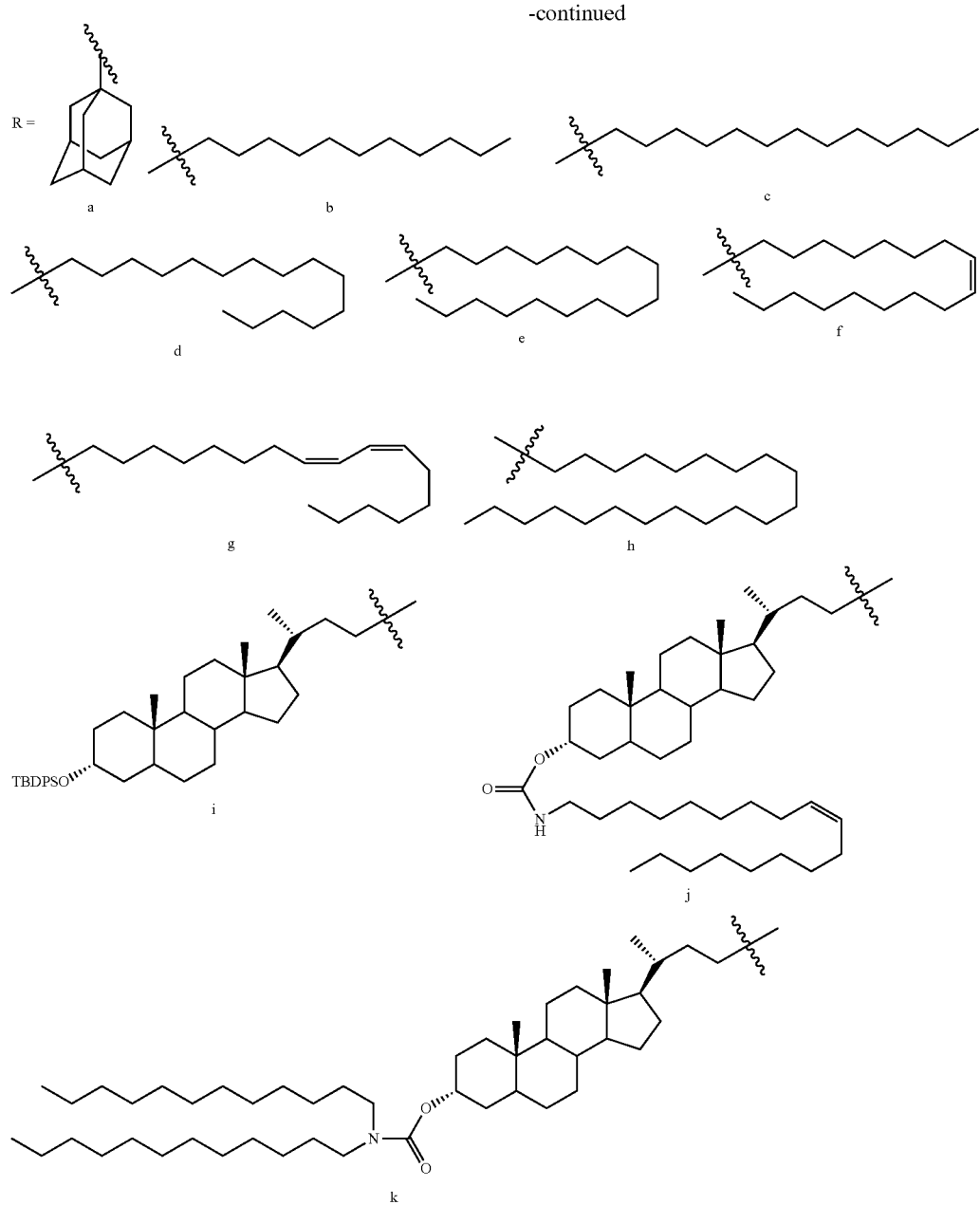
Scheme 3
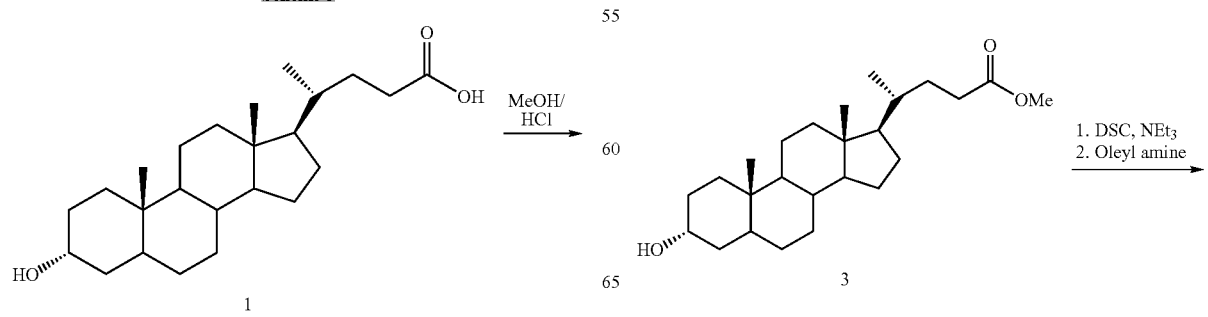

-continued
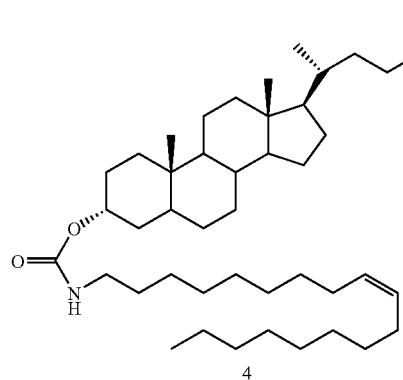
4
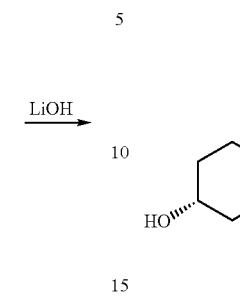
101j
Scheme 4
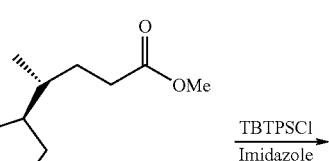
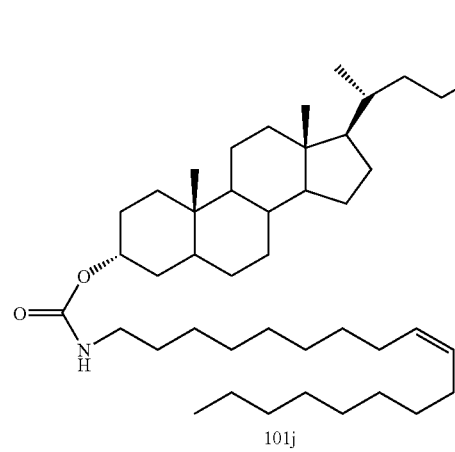
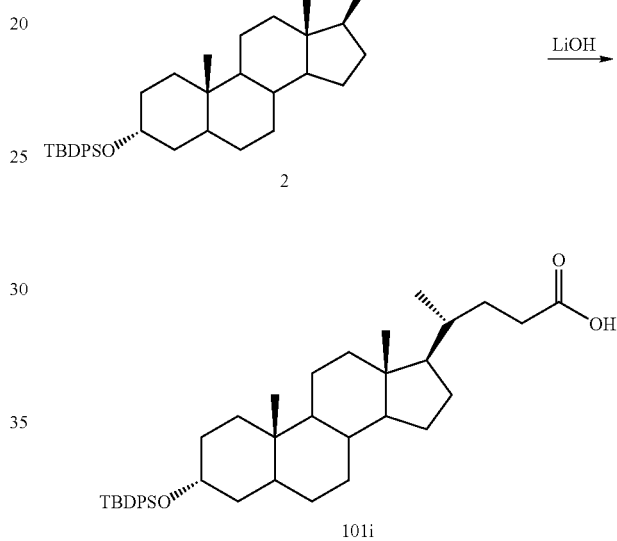
Scheme 5
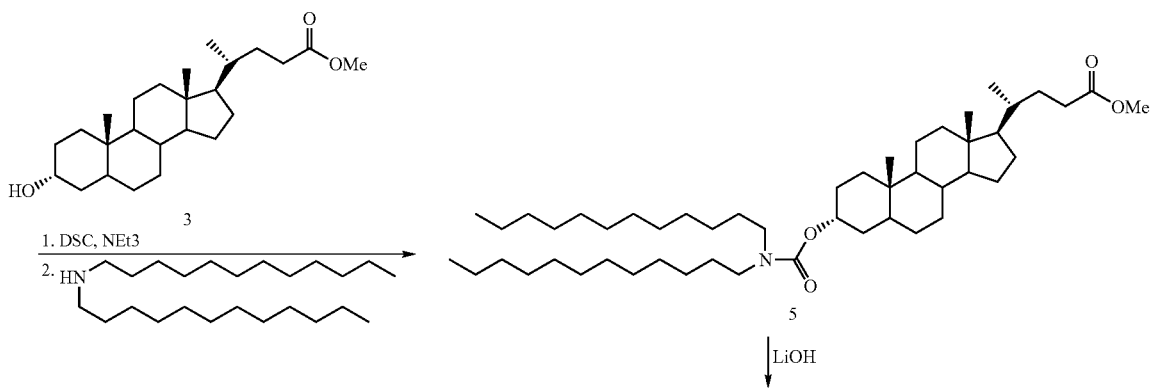

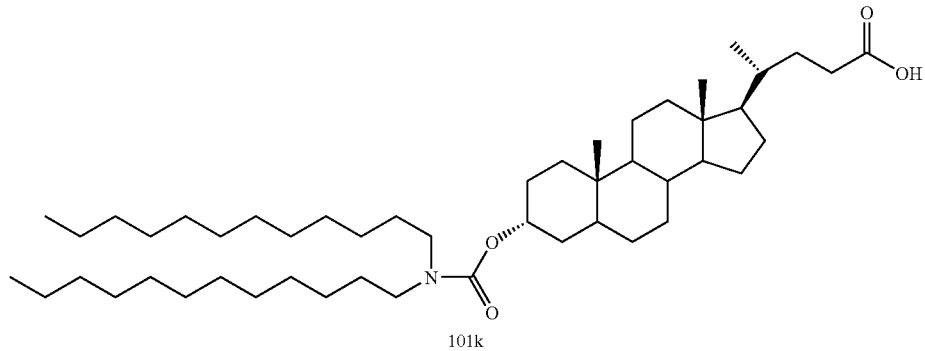

101k

General Procedure for the Synthesis of Amides 102

The carboxylic acid 101 (10 mmol) and HBTU (4.2 g, 1.1 eq.) were dissolved in DMF (30 mL) under argon. DIEA (3.81 g, 30 mmol) was added and stirred for 5 minutes. To this solution amine 100 (6.10 g, 10.7 mmol) was added and the reaction mixture was stirred at room temperature overnight. The progress of the reaction was monitored by TLC (10% MeOH/DCM). Ice-cold water was added and extracted with ethyl acetate, washed with $NaHCO_3$ solution, water and brine. Solvents were removed and residue was purified by chromatography (during the packing of column please add few drops of TEA, First elute with ethyl acetate, followed by 5% MeOH/DCM) to get the product.

Preparation of Adamentane carboxylic acid (6-{2-[bis-(4-methoxy-phenyl)-phenyl-methoxymethyl]-4-hydroxy-pyrrolidin-1-yl}-6-oxo-hexyl)-amide 102a: Using the above procedure adamentane carboxylic acid (1.80 g, 10 mmol) was coupled with the amine 100 (6.00 g, 11.27 mmol) using HBTU (4.55 g, 1.2 eq.) and DIEA (5.21 mL, 3.00 eq). After work-up and column purification the pure amide 102a was isolated as a white solid (Yield, 6.70 g, 96%). $^1$H NMR (DMSO-d6, 400 MHz) δ=7.33-7.25 (m, 5H), 7.23-7.13 (m, 5H), 6.87-6.80 (m, 4H), 4.97 (d, J=3.90 Hz, 1H), 4.88 (d, J=3.90 Hz, 1H), 4.39-4.05 (m, 2H), 3.71 (s, 6H), 3.58-3.41 (m, 1H), 3.32-3.12 (m, 2H), 3.01-2.93 (m, 3H), 2.20-1.05 (m, 25H). $^{13}$C NMR (DMSO-d6, 400 MHz) δ=171.81, 170.91, 170.80, 16=58.09, 157.96, 145.06, 144.71, 135.86, 135.71, 135.45, 135.41, 129.67, 129.57, 129.52, 129.52, 127.80, 127.69, 127.63, 127.56, 126.52, 113.14, 113.05, 85.79, 85.12, 68.59, 67.46, 63.34, 55.06, 55.01, 54.96, 54.96, 54.93, 38.27, 38.24, 36.31, 35.43, 34.17, 30.89, 29.08, 29.03, 28.73, 28.68, 28.59, 26.63, 26.60, 26.20, 25.33, 25.19, 24.14, 22.02, 21.97, 13.87

Preparation of Dodecanoic acid (6-{2-[bis-(4-methoxy-phenyl)-phenyl-methoxymethyl]-4-hydroxy-pyrrolidin-1-yl}-6-oxo-hexyl)-amide 102b: Using the above procedure Dodecanoic acid (2.00 g, 10 mmol) was coupled with the amine 100 (6.10 g, 11.45 mmol) using HBTU (4.54 g, 1.2 eq.) and DIEA (5 mL, 3.00 eq). After work-up and column purification the pure amide 102b was isolated as a pale yellow solid (Yield, 5.2 g, 71%). $^1$H NMR (DMSO-d6, 400 MHz) δ=7.73-7.68 (m, 1H), 7.42-7.31 (m, 4H), 7.27-7.09 (m, 5H), 6.91-6.80 (m, 4H), 4.97 (d, J=3.90 Hz, 1H), 4.94 (d, J=3.90 Hz, 1H), 4.41-4.05 (m, 2H), 3.71 (s, 6H), 3.59-3.41 (m, 1H), 3.35-3.11 (m, 2H), 3.05-2.91 (m, 3H), 2.22-1.78 (m, 6H), 1.51-1.0 (m, 24H), 0.82 (t, J=6.34 Hz, 3H). $^{13}$C NMR (DMSO-d6, 400 MHz) δ=171.85, 170.93, 170.83, 158.10, 157.97, 145.09, 144.75, 135.87, 135.73, 135.47, 135.42, 129.60, 129.55, 127.85, 127.78, 127.57, 126.63, 126.53, 113.18, 113.09, 85.78, 85.11, 68.58, 67.45, 63.33, 55.60, 54.99, 54.96, 53.43, 38.21, 38.02, 36.30, 35.43, 34.17, 32.54, 31.31, 29.09, 29.03, 29.01, 28.97, 28.79, 28.74, 28.67, 26.19, 25.33, 24.55, 24.15, 22.10, 21.21, 13.94.

Preparation of myristic acid (6-{2-[bis-(4-methoxy-phenyl)-phenyl-methoxymethyl]-4-hydroxy-pyrrolidin-1-yl}-6-oxo-hexyl)-amide 102c: Using the above procedure Myristic acid (2.30 g, 10 mmol) was coupled with the amine 100 (6.10 g, 11.45 mmol) using HBTU (4.54 g, 1.2 eq.) and DIEA (5 mL, 3.00 eq). After work-up and column purification the pure amide 102c was isolated as a pale yellow solid (Yield, 6.10 g, 80%). $^1$H NMR (DMSO-d6, 400 MHz) δ=7.72-7.65 (m, 1H), 7.35-7.26 (m, 4H), 7.27-7.12 (m, 5H), 6.90-6.80 (m, 4H), 4.99 (d, J=3.91 Hz, 1H), 4.89 (d, J=3.91 Hz, 1H), 4.41-4.10 (m, 2H), 3.71 (s, 6H), 3.57-3.42 (m, 1H), 3.37-3.11 (m, 2H), 3.05-2.91 (m, 3H), 2.25-1.80 (m, 6H), 1.52-1.08 (m, 28H), 0.83 (t, J=6.34 Hz, 3H). $^{13}$C NMR (DMSO-d6, 400 MHz) δ=171.84, 170.93, 170.82, 158.11, 157.98, 145.09, 144.75, 135.87, 135.72, 135.47, 135.42, 129.60, 129.55, 127.84, 127.75, 127.72, 126.56, 113.17, 113.08, 85.78, 85.12, 68.58, 67.45, 65.19, 63.33, 55.61, 55.06, 54.99, 53.44, 39.08, 38.87, 38.22, 38.02, 36.31, 35.44, 34.18, 32.54, 31.32, 29.09, 29.04, 28.99, 28.80, 28.74, 28.64, 26.20, 25.34, 24.55, 24.15, 22.11, 13.93.

Preparation of Palmitic acid (6-{2-[bis-(4-methoxy-phenyl)-phenyl-methoxymethyl]-4-hydroxy-pyrrolidin-1-yl}-6-oxo-hexyl)-amide 102d: Using the above procedure Palmitic acid (2.57 g, 10 mmol) was coupled with the amine 100 (6.10 g, 11.45 mmol) using HBTU (4.54 g, 1.2 eq.) and DIEA (5 mL, 3.00 eq). After work-up and column purification the pure amide 102d was isolated as a white solid (Yield, 6.15 g, 79%). $^1$H NMR (DMSO-d6, 400 MHz) δ=7.74-7.66 (m, 1H), 7.37-7.22 (m, 4H), 7.21-7.12 (m, 5H), 6.87-6.79 (m, 4H), 4.98 (d, J=3.90 Hz, 1H), 4.90 (d, J=3.90 Hz, 1H), 4.40-4.07 (m, 2H), 3.71 (s, 6H), 3.59-3.42 (m, 1H), 3.34-3.13 (m, 2H), 3.02-2.87 (m, 3H), 2.20-1.80 (m, 6H), 1.46-1.08 (m, 32H), 0.82 (t, J=6.35 Hz, 3H). $^{13}$C NMR (DMSO-d6, 400 MHz) δ=171.84, 170.92, 170.81, 158.11, 157.98, 145.09, 144.74, 135.87, 135.72, 135.46, 135.41, 129.59, 129.55, 127.84, 127.74, 127.57, 126.55, 113.16, 113.07, 85.78, 85.12, 68.59, 67.45, 65.19, 63.33, 59.74, 55.61, 55.06, 54.95, 53.44, 44.58, 39.08, 38.87, 38.22, 38.02, 36.30, 35.44, 34.18, 32.54, 31.32, 29.09, 29.05, 29.00, 28.81, 28.74, 28.69, 26.20, 25.34, 24.55, 24.15, 22.12, 21.20, 14.06, 13.92.

Synthesis of octadecanoic acid (6-{2-[bis-(4-methoxy-phenyl)-phenyl-methoxymethyl]-4-hydroxy-pyrrolidin-1-yl}-6-oxo-hexyl)-amide 102e. Using the above described procedure, stearic acid 101e (2.84 g, 10 mmol) was coupled with the amine 100 and after work-up and column purification the pure amide was isolated as a foam (7.17 g, 90%). $^1$H NMR (DMSO-d6, 400 MHz) δ=7.76-7.65 (m, 1H), 7.34-7.10 (m, 9H), 6.90-6.79 (m, 4H), 4.96 (d, J=3.90 Hz, 0.7H), 4.88 (d, J=3.90 Hz, 0.3H), 4.40-4.05 (m, 2H), 3.71 (s, 6H), 3.59-3.42 (m, 1H), 3.34-3.13 (m, 2H), 3.10-2.87 (m, 3H), 2.20-1.80 (m, 6H), 1.50-1.08 (m, 36H), 0.83 (t, J=6.1 Hz, 3H). $^{13}$C NMR (DMSO-d6, 400 MHz) δ=171.83, 170.92, 170.82, 162.29, 158.10, 157.97, 145.08, 144.74, 135.86, 135.42, 135.47, 129.59, 129.54, 127.84, 127.76, 127.57, 126.56, 113.18, 113.09, 85.78, 85.10, 68.57, 67.44, 65.19, 63.32, 54.97, 40.12, 38.21, 36.29, 35.77, 35.42, 34.16, 31.30, 30.75, 29.04, 28.78, 28.72, 28.65, 26.18, 25.33, 24.14, 22.10, 13.95.

Synthesis of octadec-9-enoic acid (6-{2-[bis-(4-methoxy-phenyl)-phenyl-methoxymethyl]-4-hydroxy-pyrrolidin-1-yl}-6-oxo-hexyl)-amide 102f. Using the above described procedure, oleic acid 101f (2.83 g, 10 mmol) was coupled with the amine 100 and after work-up and column purification the pure amide was isolated as aa oil (7.7 g, 98%). $^1$H NMR (DMSO-d6, 400 MHz) δ 7.71-7.67 (m, 1H), 7.34-7.10 (m, 9H), 6.90-6.79 (m, 4H), 5.33-5.26 (m, 2H), 4.98 (d, J=3.90 Hz, 0.7H), 4.88 (d, J=3.90 Hz, 0.3H), 4.40-4.05 (m, 2H), 3.71 (s, 6H), 3.59-3.42 (m, 1H), 3.34-3.20 (m, 2H), 3.18-3.10 (m, 1H), 3.02-2.92 (m, 3H), 2.20-1.80 (m, 6H), 1.50-1.04 (m, 39H), 0.83 (t, J=6.1 Hz, 3H). $^{13}$C NMR (DMSO-d6, 400 MHz) δ=171.81, 170.92, 170.83, 158.09, 157.96, 145.08, 144.74, 135.87, 135.72, 135.42, 129.61, 129.54, 127.86, 127.74, 127.57, 126.56, 113.18, 113.09, 85.78, 85.10, 68.57, 67.44, 65.19, 63.32, 54.97, 54.92, 48.59, 45.71, 40.12, 38.21, 38.02, 36.29, 35.41, 34.16, 32.53, 31.28, 29.09, 28.84, 28.69, 28.66, 28.59, 28.55, 26.58, 26.56, 26.19, 25.32, 24.54, 24.14, 22.10, 13.94.

Preparation of Linoleic acid (6-{2-[bis-(4-methoxy-phenyl)-phenyl-methoxymethyl]-4-hydroxy-pyrrolidin-1-yl}-6-oxo-hexyl)-amide 102g: Using the above procedure Linoleic acid (2.80 g, 10.5 mmol) was coupled with the amine 100 (6.10 g, 11.45 mmol) using HBTU (4.55 g, 1.2 eq.) and DIEA (5.21 mL, 3.00 eq). After work-up and column purification the pure amide 102g was isolated as pale yellow gummy liquid (Yield, 6.10 g, 78%). $^1$H NMR (DMSO-d6, 400 MHz) δ=7.71-7.67 (m, 1H), 7.33-7.25 (m, 4H), 7.23-7.13 (m, 5H), 6.87-6.80 (m, 4H), 5.35-5.24 (m, 4H), 4.97 (d, J=3.90 Hz, 1H), 4.88 (d, J=3.90 Hz, 1H), 4.39-4.05 (m, 2H), 3.72 (s, 6H), 3.58-3.41 (m, 1H), 3.32-3.12 (m, 2H), 3.01-2.93 (m, 3H), 2.72-2.67 (m, 2H), 2.20-1.80 (m, 9H), 1.46-1.08 (m, 23H), 0.83 (t, J=6.34 Hz, 3H). $^{13}$C NMR (DMSO-d6, 400 MHz) δ=176.63, 170.97, 170.86, 162.22, 158.09, 157.97, 145.07, 144.73, 135.87, 135.73, 135.48, 135.43, 129.60, 129.57, 129.55, 127.81, 127.71, 127.57, 127.55, 126.69, 126.53, 113.15, 113.07, 113.06, 85.79, 85.12, 68.61, 67.47, 63.36, 55.07, 55.01, 54.96, 54.93, 38.60, 38.56, 38.29, 38.18, 38.02, 36.30, 36.16, 36.01, 35.71, 34.17, 32.55, 30.70, 29.06, 29.02, 27.73, 27.70, 27.53, 26.08, 26.04, 24.49, 24.10.

Synthesis of docosanoic acid (6-{2-[bis-(4-methoxy-phenyl)-phenyl-methoxymethyl]-4-hydroxy-pyrrolidin-1-yl}-6-oxo-hexyl)-amide 102h. Using the above described procedure, docosanoic acid 101h (3.41 g, 10 mmol) was coupled with the amine 100 and after work-up and column purification the pure amide was isolated as a foam (3.5 g, 41%). $^1$H NMR (DMSO-d6, 400 MHz) δ=7.69 (m, 1H), 7.32-6.80 (m, 13H), 4.98 (d, J=3.90 Hz, 0.7H), 4.88 (d, J=3.90 Hz, 0.3H), 4.40-4.05 (m, 2H), 3.71 (s, 6H), 3.59-3.42 (m, 1H), 3.34-3.13 (m, 2H), 3.10-2.87 (m, 3H), 2.20-1.80 (m, 6H), 1.50-1.08 (m, 44H), 0.81 (t, J=6.1 Hz, 3H). $^{13}$C NMR (DMSO-d6, 400 MHz) δ=171.78, 170.89, 170.79, 162.30, 162.25, 158.09, 157.97, 145.08, 144.73, 135.86, 135.70, 135.45, 135.40, 129.59, 129.53, 127.82, 127.72, 127.56, 126.69, 126.52, 113.14, 113.05, 85.78, 85.10, 68.58, 67.44, 65.19, 63.32, 55.60, 55.05, 54.96, 54.93, 38.22, 38.01, 36.30, 35.76, 35.43, 34.16, 32.53, 31.35, 30.74, 29.09, 28.87, 28.78, 28.73, 26.20, 25.35, 24.13, 22.13, 13.88.

Synthesis of lithocholic acid methyl ester 3

To a solution of the lithocholic acid 1 (25.1 g, 66.4 mmol) in anhydrous methanol (100 mL), 4M HCl in 1,4-dioxane (100 mL) was added and the reaction mixture stirred at ambient temperature overnight. The reaction mixture became heterogeneous. The reaction mixture was diluted with dichloromethane (300 mL) and the organic layer was washed with saturated NaHCO$_3$ (2×200 mL). The organic layer was concentrated and dried under high vacuum overnight to provide the pure ester as a white solid (25.7 g, 97%). The analytical and spectral data were consistent with that of reported values (Rensen, Patrick C. N.; van Leeuwen, Steven H.; Sliedregt, Leo A. J. M.; Van Berkel, Theo J. C.; Biessen, Erik A. L. Design and Synthesis of Novel N-Acetylgalactosamine-Terminated Glycolipids for Targeting of Lipoproteins to the Hepatic Asialoglycoprotein Receptor. Journal of Medicinal Chemistry (2004), 47(23), 5798-5808.).

Synthesis of 3-octadec-9-enylcarbamoyloxy-lithocholic acid methyl ester 4

To a solution of the lithocholic acid methyl ester 3 (13.9 g, 35.6 mmol) in anhydrous dichloromethane (200 mL), triethylamine (10 mL) and disuccinimoyldicarbonate (13.7 g, 53.4 mmol) were added and the reaction mixture was stirred at ambient temperature overnight. The reaction mixture was then concentrated to dryness and the residue was re-dissolved in dichloromethane (300 mL). The organic layer was washed with saturated NaHCO$_3$ (3×100 mL). The organic layer was dried (Na$_2$SO$_4$), filtered and evaporated to dryness to obtain the succinimoylcarbonate of lithocholic acid methyl ester as a white foam. The oleyl amine (9.5 g, 35.6 mmol) was dissolved in anhydrous dichloromethane (50 mL) and cooled to 0° C. To this mixture anhydrous pyridine (10 mL) and the above carbonate in anhydrous CH$_2$Cl$_2$ (20 mL) was added. The reaction mixture was allowed to warm to ambient temperature and stirred for 4 h. The TLC showed the completion of the reaction and the reaction mixture was diluted with CH$_2$Cl$_2$ (200 mL) and washed with saturated NaHCO$_3$, brine and dried over anhyd. Na$_2$SO$_4$. The organic layer was concentrated and dried under high vacuum overnight to provide the crude product which was further purified by column chromatography (silica gel, 1:1 EtOAc:hexanes) to obtain the pure product as a white foam (13.7 g, 55%). $^1$H NMR (DMSO-d6, 400 MHz) δ 6.92 (t, J=5.2 Hz, 1H), 5.34-5.29 (m, 2H), 4.45-4.41 (m, 1H), 3.55 (s, 6H), 2.93-2.88 (m, 2H), 2.34-2.16 (m, 2H), 1.97-1.40 (m, 14H), 1.40-1.10 (m, 40H), 1.10-0.90 (m, 6H), 0.90-0.80 (m, 9H), 0.59 (s, 3H). $^{13}$C NMR (DMSO-d6, 400 MHz) δ=173.38, 168.34, 155.47, 149.82, 129.28, 128.85, 128.79, 81.65, 77.43, 72.98, 55.49, 55.29, 54.87, 54.82, 50.39, 41.68, 40.87, 40.75, 34.72, 34.67, 34.26, 34.13, 33.66, 33.56, 33.47, 31.78, 31.53, 30.81, 30.75, 30.69, 29.95, 29.91, 28.96, 28.67, 28.60, 28.56, 28.51, 28.42, 28.40, 28.24, 28.19, 28.14, 28.04, 27.86, 27.14, 26.12, 26.06, 25.89, 25.76, 25.37, 25.25, 25.21, 24.62, 23.16, 22.44, 22.19, 21.61, 19.78, 17.32, 13.22, 11.08.

Synthesis of 3-octadec-9-enylcarbamoyloxy-lithocholic acid 101j

To a solution of the ester 4 (13.7 g, 20 mmol) in THF (100 mL) at 0° C., an aqueous solution of lithium hydroxide [2.52 g (60 mmol) in 10 mL of water] was added and the reaction mixture was stirred at ambient temperature for 20 h after which the TLC showed the complete disappearance of the starting ester. The reaction mixture was acidified to pH 6 by drop wise addition of acetic acid and the reaction mixture was diluted with water (100 mL) and the mixture was extracted with EtOAc (3×100 mL) and the organic layers were combined, washed with water (200 mL), brine (200 mL) and dried over $Na_2SO_4$. Concentration of the organic layer provided the pure product as a foam (10.6 g, 80%). $^1$H NMR ($CDCl_3$, 400 MHz) δ 11.15 (bs, 1H), 5.44-5.25 (m, 2H), 4.58 (bs, 2H), 3.22-3.04 (m, 2H), 2.43-2.21 (m, 2H), 2.06-1.20 (m, 14H), 1.40-1.10 (m, 40H), 1.10-0.90 (m, 6H), 0.96-0.84 (m, 9H), 0.64 (s, 3H). $^{13}$C NMR (DMSO-d6, 400 MHz) δ=179.98, 156.50, 130.18, 130.01, 76.91, 74.78, 56.72, 56.19, 42.96, 42.09, 41.13, 40.64, 40.37, 36.00, 35.52, 35.28, 34.77, 32.88, 32.82, 32.12, 32.00, 31.17, 30.99, 30.21, 29.98, 29.95, 29.91, 29.87, 29.74, 29.66, 29.53, 29.47, 28.44, 28.39, 27.43, 27.40, 27.24, 26.96, 26.56, 24.39, 23.54, 22.90, 21.03, 18.46, 14.35, 12.26.

Synthesis of 3-(tert-butyl-diphenyl-silyloxy)-lithocholic acid methyl ester 2

To a solution of the lithocholic acid methyl ester 3 (11.72 g, 30 mmol) in anhydrous acetonitrile (100 mL), imidazole (4.1 g, 60 mmol) was added and the solution was cooled in an ice bath. To this cold solution, TBDPS chloride was added drop wise with stirring. The reaction mixture was allowed to warm ton ambient temperature and stirred overnight. The TLC of the reaction mixture (5% EtOAc in hexanes) showed the complete disappearance of the starting alcohol. The reaction mixture was concentrated, the residue was quenched with water (200 mL) and extracted with $CH_2Cl_2$ (3×100 mL). The combined organic layers were washed with brine and concentrated to get the crude product. The thus obtained crude product was purified by column (silica gel) chromatography using 0-5% EtOAc in hexanes. The pure product fractions were concentrated to obtain the product as a clear liquid (19.6 g, 100%). $^1$H NMR (DMSO-d6, 400 MHz) δ 7.34-7.25 (m, 4H), 7.25-7.15 (m, 4H), 6.88-6.82 (m, 2H), 5.30 (t, J=4.6 Hz, 1H), 3.31 (s, 3H), 2.34-2.16 (m, 2H), 1.90-0.97 (m, 27H), 0.92 (s, 3H), 0.90 (m, 3H), 0.64 (s, 3H).

Synthesis of 3-(tert-butyl-diphenyl-silyloxy)-lithocholic acid 101i

To a solution of the ester 2 (19.6 g, 31 mmol) in THF (100 mL) at 0° C., an aqueous solution of lithium hydroxide [6.5 g (155 mmol) in 20 mL of water] was added and the reaction mixture was stirred at ambient temperature for 20 h after which the TLC showed the complete disappearance of the starting ester. The reaction mixture was acidified to pH 6 by drop wise addition of acetic acid and the reaction mixture was diluted with water (100 mL) and the mixture was extracted with EtOAc (3×100 mL) and the organic layers were combined, washed with water (200 mL), brine (200 mL) and dried over $Na_2SO_4$. Concentration of the organic layer provided the pure product as a foam (18.8 g, 98%). $^1$H NMR (DMSO-d6, 400 MHz) δ 11.95 (bs, 1H), 7.80-7.15 (m, 10H), 3.53 (bs, 1H), 2.34-2.16 (m, 2H), 1.90-0.90 (m, 27H), 0.94 (s, 3H), 0.74 (m, 3H), 0.55 (s, 3H).

Synthesis of 3-didodecylcarbamoyloxy-lithocholic acid methyl ester 5

In a procedure similar to that of the carbamate 4 lithocholic acid methyl ester 2 (3.76 g, 10 mmol) was converted to the corresponding carbamate 5. After work-up and column purification, the pure product was isolated as a colorless oil (6.4 g, 83%). $^1$H NMR ($CDCl_3$, 400 MHz) δ 4.62 (m, 1H), 3.55 (s, 6H), 3.20-3.06 (m, 2H), 2.34-2.16 (m, 2H), 1.97-1.40 (m, 14H), 1.40-1.10 (m, 40H), 1.10-0.90 (m, 6H), 0.90-0.80 (m, 9H), 0.59 (s, 3H). $^{13}$C NMR ($CDCl_3$, 400 MHz) δ=175.04, 156.31, 72.98, 56.69, 56.23, 51.71, 42.95, 42.17, 40.68, 36.02, 35.59, 34.82, 32.15, 31.29, 29.88, 29.82, 29.59, 28.41, 28.40, 28.24, 28.19, 28.14, 28.04, 23.61, 22.92, 18.49, 14.35, 12.25

Synthesis of 3-didodecylcarbamoyloxy-lithocholic acid 101k

To a solution of the ester 5 (6.4 g, 8.3 mmol) in THF (50 mL) at 0° C., an aqueous solution of lithium hydroxide [0.42 g (10 mmol) in 5 mL of water] was added and the reaction mixture was stirred at ambient temperature for 20 h after which the TLC showed the complete disappearance of the starting ester. The reaction mixture was acidified to pH 6 by drop wise addition of acetic acid and the reaction mixture was diluted with water (100 mL) and the mixture was extracted with EtOAc (3×100 mL) and the organic layers were combined, washed with water (200 mL), brine (200 mL) and dried over $Na_2SO_4$. Concentration of the organic layer provided the pure product as a foam (6 g, 95%). $^1$H NMR ($CDCl_3$, 400 MHz) δ 11.35 (bs, 1H), 4.62 (m, 1H), 3.55 (s, 6H), 3.20-3.06 (m, 2H), 2.34-2.16 (m, 2H), 1.97-1.40 (m, 14H), 1.40-1.10 (m, 40H), 1.10-0.90 (m, 6H), 0.90-0.80 (m, 9H), 0.59 (s, 3H). $^{13}$C NMR ($CDCl_3$, 400 MHz) δ=175.04, 156.31, 72.98, 56.69, 56.23, 51.71, 42.95, 42.17, 40.68, 36.02, 35.59, 34.82, 32.15, 31.29, 29.88, 29.82, 29.59, 28.41, 28.40, 28.24, 28.19, 28.14, 28.04, 23.61, 22.92, 18.49, 14.35, 12.25.

Synthesis of 3-(tert-butyl-diphenyl-silyloxy)-lithocholic acid (6-{2-[bis-(4-methoxy-phenyl)-phenyl-methoxymethyl]-4-hydroxy-pyrrolidin-1-yl}-6-oxo-hexyl)-amide 102i. Using the above described procedure, 3-(tert-butyl-diphenyl-silyloxy)-lithocholic acid 101i (2.46 g, 4 mmol) was coupled with the amine 100 and after work-up and column purification the pure amide was isolated as an oil (3.2 g, 70%). $^1$H NMR (DMSO-d6, 400 MHz) δ 7.71 (bs, 1H), 7.30-7.15 (m, 19H), 6.98-6.82 (m, 4H), 5.33 (bs, 1H), 5.30 (t, J=4.6 Hz, 1H), 4.98 (d, J=3.9 Hz, 0.7H), 4.90 (d, J=3.9 Hz, 0.3H), 4.46-4.14 (m, 1H), 3.71 (s, 3H), 3.60-3.15 (m, 2H), 3.10-2.88 (m, 2.34-2.16 (m, 2H), 1.90-0.90 (m, 27H), 0.94 (s, 3H), 0.74 (m, 3H), 0.55 (s, 3H). $^{13}$C NMR (DMSO-d6) δ 172.25, 170.95, 170.85, 162.32, 158.10, 157.98, 155.80, 145.09, 144.75, 135.89, 135.73, 135.47, 129.62, 127.78, 127.58, 126.59, 113.10, 85.12, 72.99, 68.58, 63.33, 56.00, 55.58, 54.99, 45.71, 42.24, 41.24, 38.25, 36.30, 35.79, 35.30, 34.92, 34.65, 34.16, 32.43, 31.64, 31.32, 30.77, 29.38, 29.11, 28.87, 28.82, 28.74, 28.61, 28.52, 26.58, 26.18, 24.17, 23.83, 23.07, 22.13, 20.38, 18.27, 13.96, 11.85. MS. Molecular weight calculated for $C_{72}H_{96}N_2O_7Si$, Cal. 1128.7°, Found Synthesis of 3-octadec-9-enylcarbamoyloxy-lithocholic acid (6-{2-[bis-(4-methoxy-phenyl)-phenyl-methoxymethyl]-4-hydroxy-pyrrolidin-1-yl}-6-oxo-hexyl)-amide 102j. Using the above described procedure, 3-octadec-9-enylcarbamoyloxy-lithocholic acid 101j (2.68 g, 4 mmol) was coupled with the amine 100 and after work-up and column purification the pure amide 102j was isolated as an oil (4.45 g, 95%). $^1$H NMR (DMSO-d6, 400 MHz) δ 7.94 (bs, 1H), 7.58 (dd, J=1.3 and 7.65 Hz, 4H), 7.45-7.12 (m, 15H), 6.90-6.82 (m, 4H), 4.98 (d, J=3.9 Hz, 0.7H), 4.89 (d, J=3.9 Hz, 0.3H), 4.46-4.14 (m, 2H), 3.71 (s, 3H), 3.60-3.15 (m, 2H), 3.10-2.88 (m, 2.34-2.16 (m, 2H), 1.90-0.90 (m, 42H), 0.96 (s, 3H), 0.86-0.80 (m, 3H), 0.74 (m, 3H), 0.55 (s, 3H). $^{13}$C NMR (DMSO-d6) δ 172.23, 170.91, 170.82, 158.09, 157.96, 145.07, 144.72, 135.87, 135.71, 135.45, 135.40, 135.19, 134.10, 134.01, 129.69, 129.58, 129.52, 127.84, 127.75, 127.68, 127.56, 126.73, 126.56, 113.16, 113.08, 85.77, 85.10, 73.11, 68.57, 67.44, 65.17, 63.32, 55.81, 55.61, 55.05, 54.98, 54.95, 42.21, 41.37, 38.21, 38.01, 36.30, 36.14, 35.25, 34.90, 34.82, 32.50, 31.69, 30.38, 29.06, 27.72, 26.78, 26.16, 25.98, 24.54, 24.13, 23.77, 22.96, 20.40, 18.66, 18.28, 11.81.

Synthesis of 3-didodecylcarbamoyl-lithocholic acid (6-{2-[bis-(4-methoxy-phenyl)-phenyl-methoxymethyl]-4-hydroxy-pyrrolidin-1-yl}-6-oxo-hexyl)-amide 102k. Using the above described procedure, 3-didodecylcarbamoyl-lithocholic acid 101k (2.68 g, 4 mmol) was coupled with the amine 100 and after work-up and column purification the pure amide was isolated as an oil (4.45 g, 95%). $^1$H NMR (CDCl$_3$, 400 MHz) δ 7.45-7.12 (m, 9H), 6.90-6.82 (m, 4H), 5.90 (d, J=3.9 Hz, 0.7H), 5.81 (d, J=3.9 Hz, 0.3H), 4.46-4.14 (m, 2H), 3.71 (s, 3H), 3.60-3.15 (m, 2H), 3.10-2.88 (m, 6H), 2.34-2.16 (m, 9H), 1.90-0.90 (m, 56H), 0.96 (s, 3H), 0.86-0.80 (m, 9H), 0.74 (m, 3H), 0.55 (s, 3H).

General Procedure for the Synthesis of Succinates 103

To a solution of the alcohol 102 (3 mmol) in anhydrous dichloromethane (100 mL), DMAP (1.1 g, 9 mmol) was added followed by the addition of succinic anhydride (0.6 g, 6 mmol). The reaction mixture was stirred at room temperature overnight. The TLC of the reaction mixture showed the complete disappearance of the starting alcohol. The reaction mixture was cooled in ice and to it few drops of NEt$_3$ was added. The reaction mixture was washed with a ice-cold solution of 10% aqueous citric acid (2×50 mL) followed by water, brine and dried over anhydrous sodium sulfate. Concentration of the organic layer provided the product 103 which was used as such in the next step with out any further purification.

Synthesis of succinic acid mono-{5-[bis-(4-methoxy-phenyl)-phenyl-methoxymethyl]-1-(6-octadecanoylamino-hexanoyl)-pyrrolidin-3-yl}ester 103e. Using the above described procedure, the amide 102e (2.4 g, 3 mmol) was treated with succinic anhydride and after work-up the amide was isolated as a foam (2.69 g, 99%) and this was used in the next step without further purification.

Synthesis of succinic acid mono-{5-[bis-(4-methoxy-phenyl)-phenyl-methoxymethyl]-1-(6-octadec-9-enoylamino-hexanoyl)-pyrrolidin-3-yl}ester 103f. Using the above described procedure, the amide 102f (2.4 g, 3 mmol) was treated with succinic anhydride and after work-up the amide was isolated as a foam (2.8 g, 99%) and this was used in the next step without further purification.

Synthesis of succinic acid mono-{5-[bis-(4-methoxy-phenyl)-phenyl-methoxymethyl]-1-(6-docosanoylamino-hexanoyl)-pyrrolidin-3-yl}ester 103h. Using the above described procedure, the amide 102h (2.56 g, 3 mmol) was treated with succinic anhydride and after work-up the amide was isolated as a foam (2.8 g, 99%) and this was used in the next step without further purification.

Synthesis of succinic acid 103i. Using the above described procedure, the amide 102i (2.82 g, 2.5 mmol) was treated with succinic anhydride and after work-up the amide was isolated as a foam (3 g, 99%) and this was used in the next step without further purification.

Synthesis of succinic acid 103j. Using the above described procedure, the amide 102j (2.36 g, 2 mmol) was treated with succinic anhydride and after work-up the amide was isolated as a foam (2.56 g, 99%) and this was used in the next step without further purification.

Synthesis of succinic acid 103k. Using the above described procedure, the amide 102k (2.8 g, 2.2 mmol) was treated with succinic anhydride and after work-up the amide was isolated as a foam (3 g, 99%) and this was used in the next step without further purification.

Preparation of Long alkyl chain CPG 104a: Hydroxy derivative 102a (Adamantane carboxylic acid) (2.58 g, 3.71 mmol) was dissolved in DCM (20 mL) to that Succinic anhydride (0.742 g, 2 eq) and DMAP (1.36 g, 3 eq.) were added and stirred overnight. TLC showed completion of reaction. The reaction mixture was diluted with DCM (20 mL), washed successively with cold dilute citric acid and water (2 times), dried over sodium sulfate. Solvents were removed and dried under high vacuum to get the succinate 103a. PPh$_3$ (1.073 g, 1.1 eq.), DMAP (0.498 g, 1.1 eq.) and the succinate from the previous step were dissolved in a mixture of acetonitrile and DCM (20 mL). A solution of DTNP (1.208 g, 1.05 eq.) in DCM (8 mL) was added to the above solution. The mixture was slowly shaken for 3-4 minutes. Long chain alkyl amine-CPG (lcaa CPG, 20.0 g, 133 μmol/g) was added to the mixture and gently shaken for 2 h. The CPG was filtered, successively washed with DCM, mixture of MeOH/DCM (1:9) and DCM until filtrate remained colorless and dried. The dried CPG was transferred into another flask treated with Ac$_2$O in pyridine (25%) in the presence of TEA (1 mL) for 15 min. under gentle shaking. Finally the CPG was filtered, washed with DCM, DCM:MeOH (9:1), followed by DCM and ether. The CPG 104a was dried under vacuum overnight and the loading was measured as reported (20.51 g, loading 69 μmol/g).

Preparation of Long alkyl chain CPG 104b: Compound 102b (2.02 g, 2.76 mmol) was dissolved in DCM (20 mL) to that Succinic anhydride (0.556 g, 2 eq) and DMAP (1.02 g, 3 eq.) were added and stirred overnight. The reaction mixture was diluted with DCM (20 mL), washed with cold dilute citric acid and water (2 times), dried over sodium sulfate. Solvents were removed and residue was directly used for next reaction with out further purification. Compound 103b from the previous step and HBTU (1.25 g, 1.2 eq.) were dissolved in a mixture of DCM/DMF (1:1) to that DIEA (1.5 mL) was added and kept for 5 minutes. Long chain alkyl amine-CPG (lcaa CPG, 13.30 g, 133 μmol/g) was added to above solution and shaken for 2 hrs. CPG was filtered off, washed with DMF, a mixture of DCM/MeOH, DCM and dried. CPG was transferred to the same flask and treated with 25% Ac$_2$O in Py (with small amount of TEA) and shaken well for ½ h. The solid was filtered off, washed with DCM, a mixture of DCM/MeOH, DCM and diethyl ether. CPG was transferred to a bottle and dried overnight under high vacuum and the loading was measured as reported (Yield=13.63 g, Loading 53 μmol/g).

Preparation of Long alkyl chain CPG 104c: Compound 102 (2.16 g, 2.84 mmol) was dissolved in DCM (20 mL) to that Succinic anhydride (0.571 g, 2 eq) and DMAP (1.03 g, 3 eq.) were added and stirred overnight. The reaction mixture was diluted with DCM, washed with cold dilute citric acid and water (2 times), dried over sodium sulfate. Solvents were removed and residue was directly used for next reaction with out further purification. Compound 103c from the previous step and HBTU (1.28 g, 1.2 eq.) were dissolved in a mixture of DCM/DMF (1:1) to that DIEA (1.5 mL, 3 eq) was added and kept for 5 minutes. Long chain alkyl amine-CPG (lcaa CPG, 13.40 g, 133 μmol/g) was added to above solution and shaken for 2 hrs. CPG was filtered off, washed with DMF, a mixture of DCM/MeOH, DCM and dried. CPG was transferred to the same flask and treated with 25% Ac$_2$O in Py (with small amount of TEA) and shaken well for ½ h. The solid was filtered off, washed with DCM, a mixture of DCM/MeOH, DCM and diethyl ether. CPG was transferred to a bottle and dried overnight under high vacuum and the loading was measured as reported (Yield=13.69 g, Loading 47.27 μmol/g).

Preparation of Long alkyl chain CPG 104d: Compound 102d (2.08 g, 2.64 mmol) was dissolved in DCM (20 mL) to that Succinic anhydride (0.532 g, 2 eq) and DMAP (0.966 g, 3 eq.) were added and stirred overnight. The reaction mixture was diluted with DCM (20 mL), washed with cold dilute citric acid and water (2 times), dried over sodium sulfate. Solvents were removed and residue was directly used for next reaction with out further purification. Compound 103d from the previous step and HBTU (1.20 g, 1.2 eq.) were dissolved in a mixture of DCM/DMF (1:1) to that DIEA (1.5 mL) was added and kept for 5 minutes. Long chain alkyl amine-CPG (lcaa CPG, 14.2 g, 133 µmol/g) was added to above solution and shaken for 2 hrs. CPG was filtered off, washed with DMF, a mixture of DCM/MeOH, DCM and dried. The dried CPG was transferred into another flask treated with $Ac_2O$ in pyridine (25%) in the presence of TEA (1 mL) for 15 min. under gentle shaking. The solid was filtered off, washed with DCM, a mixture of DCM/MeOH, DCM and diethyl ether. CPG was transferred to a bottle and dried overnight under high vacuum and the loading was measured as reported (Yield=14.05 g, Loading 39.2 µmol/g).

General Procedure for the Synthesis of CPG's 104e, 104f, 104h, 104i, 104j and 104k The succinic acids 103 (3 mmol) was dissolved in anhydrous DMF (30 mL) and to it diisopropylethylamine (10 eq.) was added followed by HATU (1.3 eq.) and the mixture was stirred for 5 minutes. To this solution $CPG-NH_2$ (lcaa CPG, 133 µmol/g) was added and the resulting mixture was shaken in a shaker for 2 h. The residue was filtered and washed with 20 mL of DMF, 200 mL of dichloromethane, 400 mL of 5% MeOH in dichloromethane and 300 mL of dichloromethane. The thus obtained solid was dried and the powder was transferred to a RB flask and to it capping agent (30 mL, of 25% acetic anhydride in pyridine) was added and the resulting heterogeneous mixture was again shaken in the shaker for 1 h. The mixture was then filtered and washed with 200 mL of $CH_2Cl_2$, 100 mL of 5% MeOH in $CH_2Cl_2$, 200 mL of $CH_2Cl_2$ and 200 mL of anhydrous ether. The residue was dried under vacuo overnight to get a free flowing powder. The loading was calculated by measuring the absorption in a DU 800 spectrophotometer as reported.[a]

The CPG 104e was synthesized using the above procedure and treatment of 2.69 g of 103e with 15 g of CPG provided 15.67 g of product and 61 µM/g loading was observed.

The CPG 104f was synthesized using the above procedure and treatment of 2.83 g of 103f with 1°g of CPG provided 19.3 g of product and 70 µM/g loading was observed.

The CPG 104h was synthesized using the above procedure and treatment of 2.75 g of 103h with 15 g of CPG provided 15.85 g of product and 68 µM/g loading was observed.

The CPG 104i was synthesized using the above procedure and treatment of 3 g of 103i with 1°g of CPG provided 10.4 g of product and 70 µM/g loading was observed.

The CPG 104j was synthesized using the above procedure and treatment of 2.56 g of 103j with 1°g of CPG provided 11.8 g of product and 25 µM/g loading was observed.

Example 2

Synthesis of siRNA-Lipophile Conjugates

Sense and antisense strands of control and corresponding 3'-lipophile conjugated sense strands were individually synthesized and purified according to the standard oligonucleotide synthesis and deprotection protocols. Commercially available 5'-O-(4,4'-dimethoxytrityl)-2'-O-t-butyldimethylsilyl-3'-O-(2-cyanoethyl-N,N-diisopropyl) RNA and the corresponding 2'-O-methyl phosphoramidite monomers of 6-N-benzoyladenosine ($A^{Bz}$), 4-N-acetylcytidine ($C^{Ac}$), 2-N-isobutyrylguanosine ($G^{iBu}$), and uridine (U) were used for unmodified and 2'-O-methylsugar modified RNA synthesis. The 2'-deoxy-2'-fluoro sugar modified pyrimidines were introduced to the RNA by using 5'-O-(4,4'-dimethoxytrityl)-2'-deoxy-2'-fluoro-3'-O-(2-cyanoethyl-N,N-diisopropyl) phosphoramidite monomers of 4-N-acetylcytidine ($C^{Ac}$) and uridine (U).

All lipophile bearing solid supports to conjugate the lipophiles to 3'-end of sense strand were synthesized as described in Example 1. Each individual lipophile conjugated sense strand was synthesized from the corresponding hydroxyprolinol-lipophile solid support. Beaucage reagent was used as an oxidant to obtain the phosphorothioate backbone modification. The lipophile conjugated sense strands were purified by reverse phase-high performance liquid chromatography (RP-HPLC) on an in-house packed Source 15RPC resin reverse-phase column. The buffers were 20 mM NaOAc in 10% $CH_3CN$ (buffer A) and 20 mM NaOAc in 70% $CH_3CN$ (buffer B). The unconjugated RNA oligonucleotides were purified by anion-exchange HPLC. Fractions containing full-length oligonucleotides were pooled, desalted and lyophilized. Analytical HPLC, CGE and ES LC-MS established the integrity of the compounds. For duplex generation, equimolar amounts of sense and antisense strand were heated in 1×PBS at 95° C. for 5 min and slowly cooled to room temperature. Annealing of equimolar mixture of sense and antisense strands in 1×PBS buffer afforded the desired siRNA.

TABLE 1

Lipophile conjugated siRNA duplexes.

| Target | Duplex | Sequence | SEQ ID NO: | Ligand |
|---|---|---|---|---|
| ApoB | 1 | 5'-GUCAUCACACUGAAUACCAAU$_s$Hyp-NH$_2$-3' | 1 | Amino-linker |
|  |  | 5'-AUUGGUAUUCAGUGUGAUGAc$_s$a$_s$C-3' | 2 |  |
| ApoB | 2 | 5'-GUCAUCACACUGAAUACCAAU$_s$Hyp-L1-3' | 3 | $C_{27}$; Cholesterol |
|  |  | 5'-AUUGGUAUUCAGUGUGAUGAc$_s$a$_s$C-3' | 2 |  |
| ApoB | 3 | 5'-GUCAUCACACUGAAUACCAAU$_s$Hyp-L2-3' | 4 | $C_{11}$; |
|  |  | 5'-AUUGGUAUUCAGUGUGAUGAc$_s$a$_s$C-3' | 2 | 1-Adamentaneformyl |
| ApoB | 4 | 5'-GUCAUCACACUGAAUACCAAU$_s$Hyp-L3-3' | 5 | $C_{12}$; Lauroyl |
|  |  | 5'-AUUGGUAUUCAGUGUGAUGAc$_s$a$_s$C-3' | 2 |  |
| ApoB | 5 | 5'-GUCAUCACACUGAAUACCAAU$_s$Hyp-L4-3' | 6 | $C_{14}$; Myristoyl |
|  |  | 5'-AUUGGUAUUCAGUGUGAUGAc$_s$a$_s$C-3' | 2 |  |
| ApoB | 6 | 5'-GUCAUCACACUGAAUACCAAU$_s$Hyp-L5-3' | 7 | $C_{16}$; Palmitoyl |
|  |  | 5'-AUUGGUAUUCAGUGUGAUGAc$_s$a$_s$C-3' | 2 |  |
| ApoB | 7 | 5'-GUCAUCACACUGAAUACCAAU$_s$Hyp-L6-3' | 8 | $C_{18}$; Stearoyl |
|  |  | 5'-AUUGGUAUUCAGUGUGAUGAc$_s$a$_s$C-3' | 2 |  |

TABLE 1-continued

Lipophile conjugated siRNA duplexes.

| Target | | DuplexSequence | SEQ ID NO: | Ligand |
|---|---|---|---|---|
| ApoB | 8 | 5'-GUCAUCACACUGAAUACCAAU$_s$Hyp-L7-3'<br>5'-AUUGGUAUUCAGUGUGAUGAc$_s$a$_s$C-3' | 9<br>2 | $C_{18}$; Oleoyl |
| ApoB | 9 | 5'-GUCAUCACACUGAAUACCAAU$_s$Hyp-L8-3'<br>5'-AUUGGUAUUCAGUGUGAUGAc$_s$a$_s$C-3' | 10<br>2 | $C_{18}$; Linoleoyl |
| ApoB | 10 | 5'-GUCAUCACACUGAAUACCAAU$_s$Hyp-L9-3'<br>5'-AUUGGUAUUCAGUGUGAUGAc$_s$a$_s$C-3' | 11<br>2 | $C_{22}$; Docosanoyl |
| ApoB | 11 | 5'-GUCAUCACACUGAAUACCAAU$_s$Hyp-L10-3'<br>5'-AUUGGUAUUCAGUGUGAUGAcsasC-3' | 12<br>2 | $C_{43}$; Lithocholic-oleyl |
| ApoB | 12 | 5'-GUCAUCACACUGAAUACCAAU$_s$Hyp-L11-3'<br>5'-AUUGGUAUUCAGUGUGAUGAc$_s$a$_s$C-3' | 13<br>2 | $C_{24}$; Lithocholyl |
| ApoB | 13 | 5'-GUCAUCACACUGAAUACCAAU$_s$Hyp-L12-3'<br>5'-AUTJGGUAUUCAGUGUGAUGAc$_s$a$_s$C-3' | 14<br>2 | $C_{24}$ 5β-Cholanyl |
| ApoB | 14 | 5'-GUCAUCACACUGAAUACCAAU$_s$Hyp-L13-3'<br>5'-AUUGGUAUUCAGUGUGAUGAc$_s$a$_s$C-3' | 15<br>2 | $C_{29}$; Vitamin E |
| ApoB | 15 | 5'-GUCAUCACACUGAAUACCAAU$_s$Hyp-L14-3'<br>5'-AUUGGUAUUCAGUGUGAUGAc$_s$a$_s$C-3' | 16<br>2 | $C_{60}$; N,N-Distearyl-lithocholamide |

Example 3

HPLC Titration of Hydrophobicity of Lipophile-siRNA Conjugates

Figure 3:
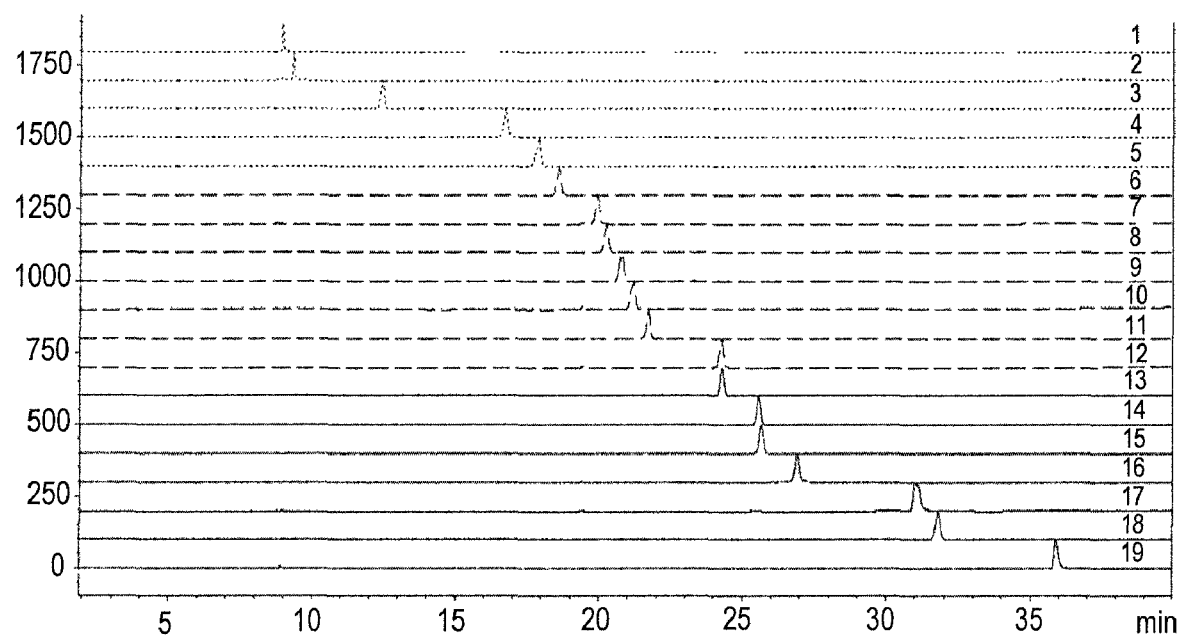
FIG. 3 is a trace of RP-HPLC titration of lipophilicity of conjugated siRNA. Traces are as follows: (1) Control sense strand (5'-GUCAUCACACUGAAUACCAA$_s$U (SEQ ID NO:44)); (2) Sense strand with amino-linker; (3) Adamantaneformyl; (4) Lauroyl; (5) Lithocholyl; (6) Myristoyl; (7) Linoleoyl; (8) Palmitoyl; (9) Oleoyl; (10) 5β-cholanyl; (11) Stearoyl; (12) Cholesteryl; (13) Docosanoyl; (14) Vitamin E; (15) Thiocholesterol; (16) Lithocholic-Oleyl; (17) Cholesteryl-Cholesterol (bis-Cholesterol); (18) 1,2-Di-O-stearylglyceride and (19) N,N-Distearyl-lithocholamide.

Each sense strand bearing the ligand was individually injected to an analytical HPLC loaded with a reverse-phase C4 Delta Pack column (from Waters) and eluted under reverse-phase condition at 35° C. with a flow rate of 1.2 mL/min.: Grad: A(100%) 0-3 min and A(100%)->B(100%) from 3 to 43 min; A: 50 mM TEAA in H2O and B: 100% MeCN. The analysis of each duplex was performed under identical condition and the retention times of the duplexes were compared for relative hydrophobicity, shown in FIG. 3. Unconjugated and amino-linker bearing sense strands were used as reference.

Example 4

In Vivo siRNA Activity

Figure 4A:
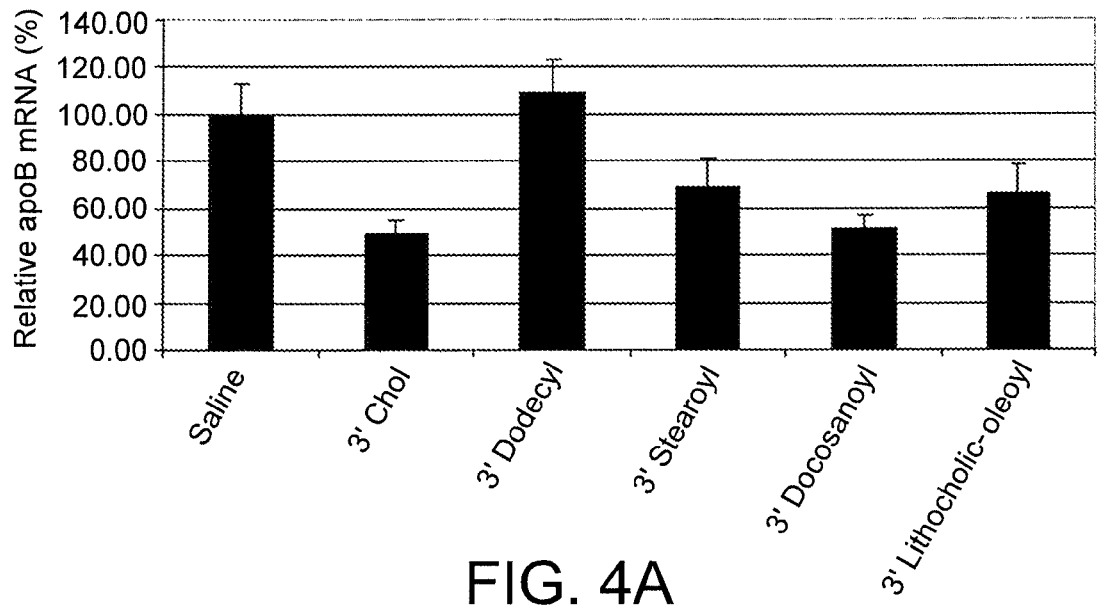
FIGS. 4A and 4B are bar graphs depicting the percentage of relative apoB mRNA in liver and jejunum respectively upon treatment with lipophile-apoB-siRNA conjugates.
Figure 4B:
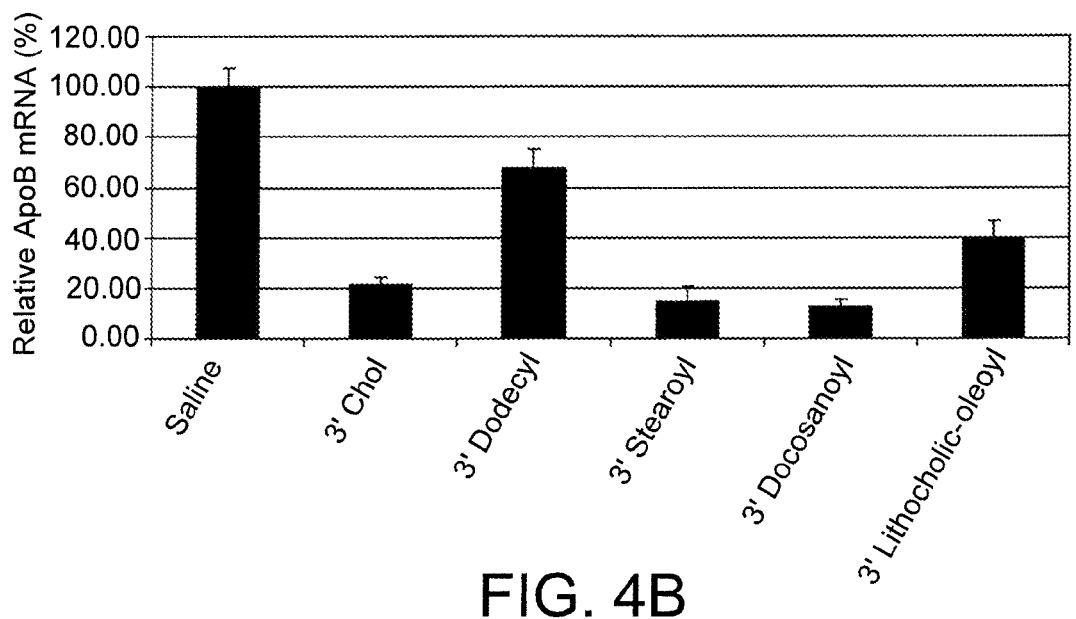

Various siRNA conjugates were analyzed in an in vivo assay. The general study design for each of the siRNA conjugates is as provided below:
Female mice BL6, 8-10 weeks
5-6 Animals/group
Dosage 50 mg/kg once daily for 3 days, iv injection and sacrificed 24 h after last injection 100 mg/kg iv single injection and sacrificed 72 h after injection
Collect blood and harvest liver and jejunum
Liver and Jejunum apoB mRNA levels were evaluated in the following siRNA conjugates 3' Chol (siRNA 2); 3' Dodecyl (siRNA 4); 3' Stearoyl (siRNA 7); 3'Docosanoyl (siRNA 10) and 3'Lithocholic-oleyl (siRNA 11). The results of the in vivo assay are provided in FIGS. 4A and 4B, for Liver and Jejunum respectively.

Figure 5A:
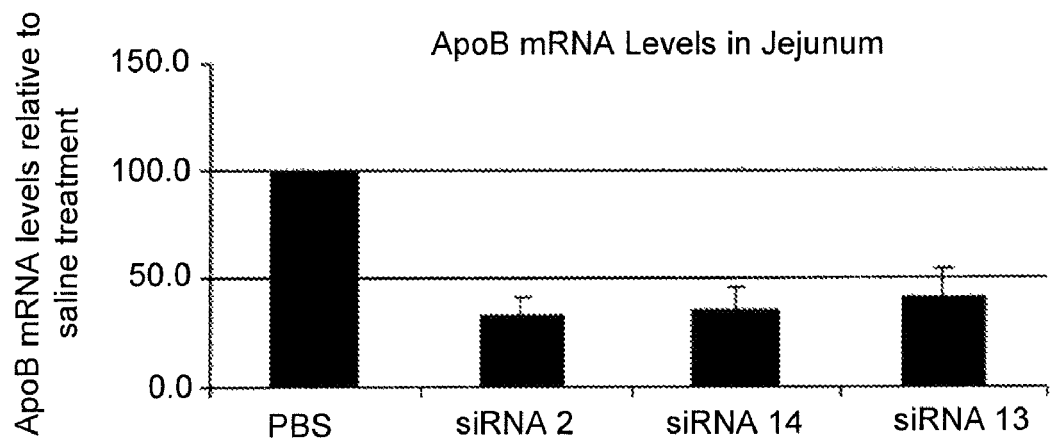
FIGS. 5A and 5B are bar graphs depicting the amount apoB mRNA in jejunum and liver respectively upon treatment with lipophile-apoB-siRNA conjugates relative to treatment with saline alone.
Figure 5B:
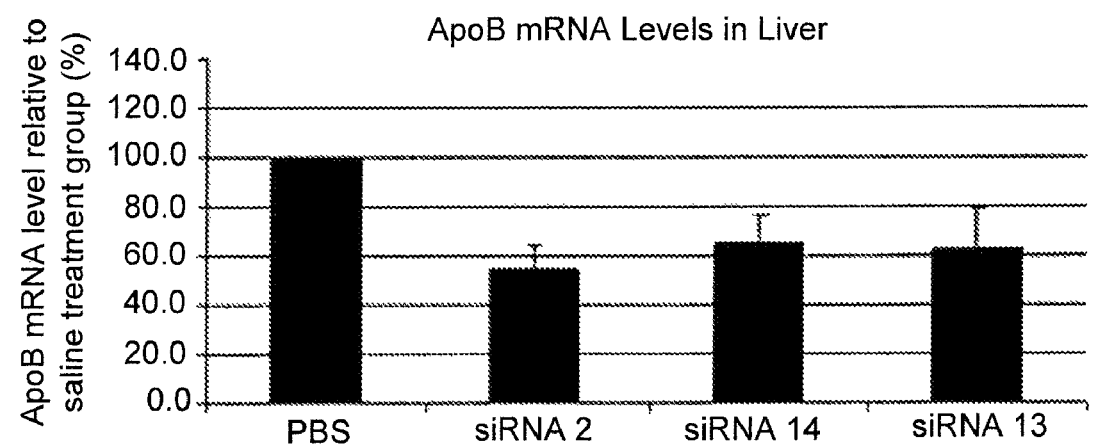

In vivo siRNA activity of lipophile-apoB-siRNA conjugates siRNA 2, siRNA 14, and siRNA 13 (Table 1 above) were evaluated. FIG. 5A depicts ApoB mRNA levels in the Jejunum, and FIG. 5B ApoB mRNA levels in the Liver. Both figures show mRNA levels after systemic administration of lipophile conjugated siRNA in vivo. Female BL6 mice 8-12 weeks old; 6 mice/group; single iv injection 100 mg/kg; sacrificed 72 h after injection: siRNA 2 (Chol-siRNA); siRNA 14 (VitaminE-siRNA) and siRNA 13 (5β-cholanyl-siRNA).

Figure 6A:
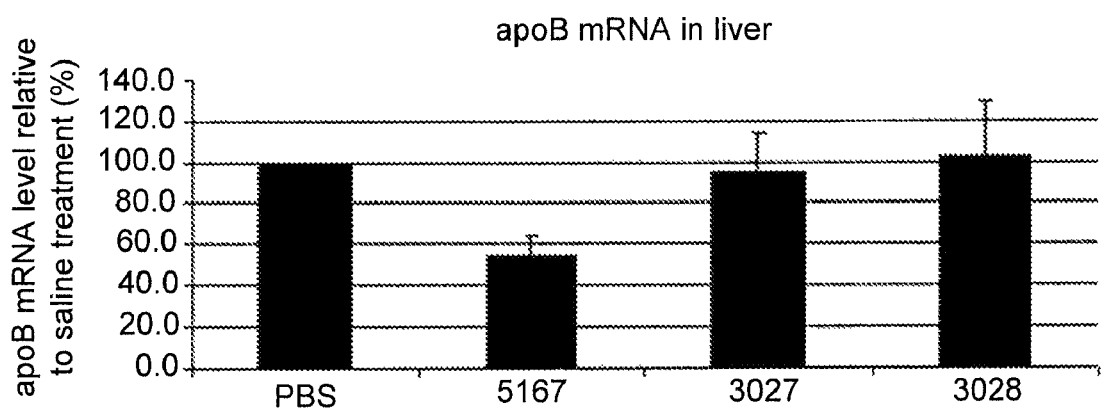
FIGS. 6A and 6B are bar graphs depicting the percentage of relative apoB mRNA in liver and jejunum respectively upon treatment with PEGylated siRNA. Mice were treated with 100 mg/kg iv single injection and sacrificed 72 h after injection.
Figure 6B:
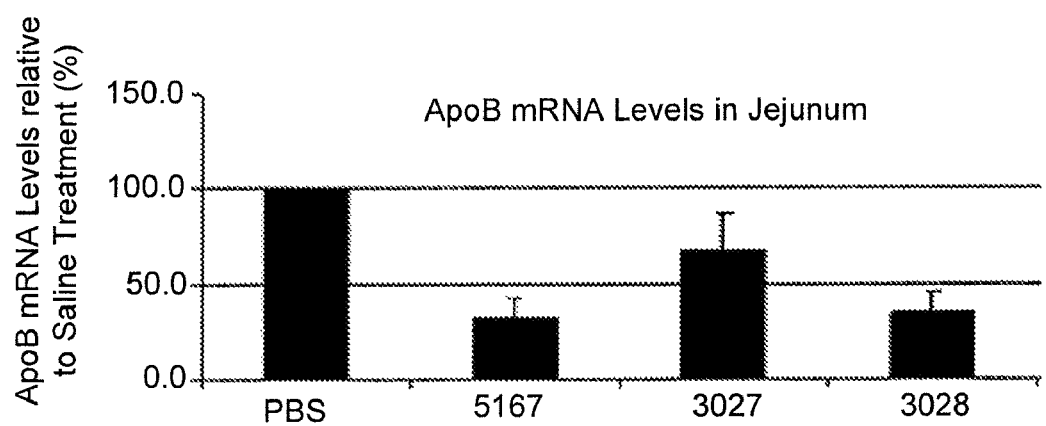

In vivo apoB gene silencing of PEGylated siRNA was evaluated in liver and jejunum, the results of which are depicted in FIGS. 6A (Liver) and 6B (Jejunum). The apoB mRNA levels were evaluated after systemic administration of PEG conjugated siRNA in vivo. Female BL6 mice 8-12 weeks old; 6 mice/group; single iv injection 100 mg/kg; sacrificed 72 h after injection: 5167 (Chol-siRNA, positive control); 3027 (PEG5000-siRNA) and 3028 (PEG20,000-siRNA).

Figure 7:
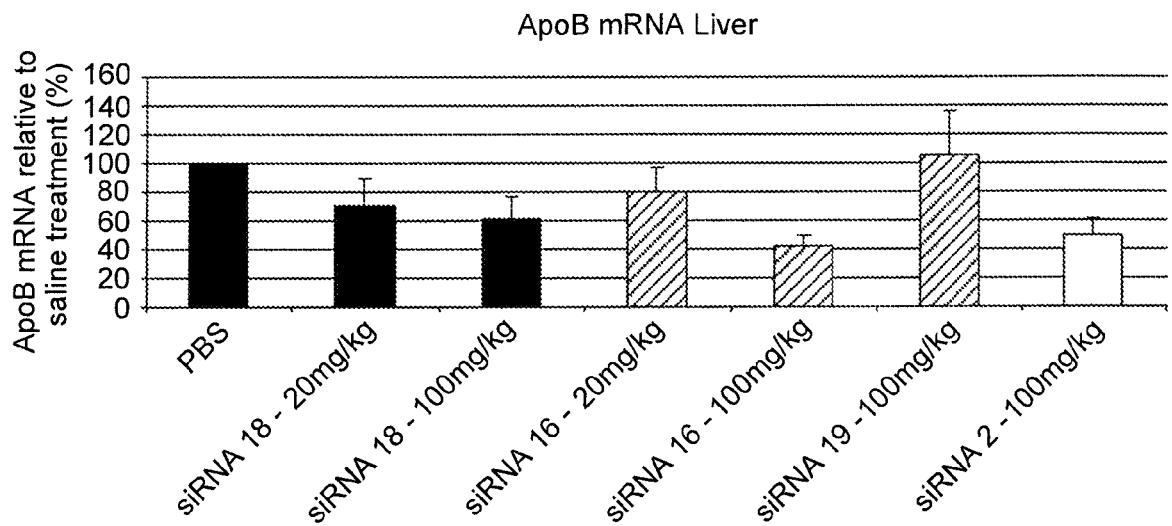
FIG. 7 is a bar graph depicting the percentage of relative apoB mRNA in liver upon treatment with thiocholesterol conjugated siRNA.

In vivo liver apoB gene silencing of thiocholesterol conjugated siRNA was evaluated, the results of which are depicted in FIG. 7. Female BL6 mice 6-8 weeks old; 6 mice/group; iv injection 20 and 100 mg/kg; sacrificed 72 h after injection. siRNA 18, siRNA 16, siRNA 19, and siRNA 2, as depicted in the Table depicting exemplary siRNA-lipophile conjugates, Table 1, above, were used in this study.

Figure 8:
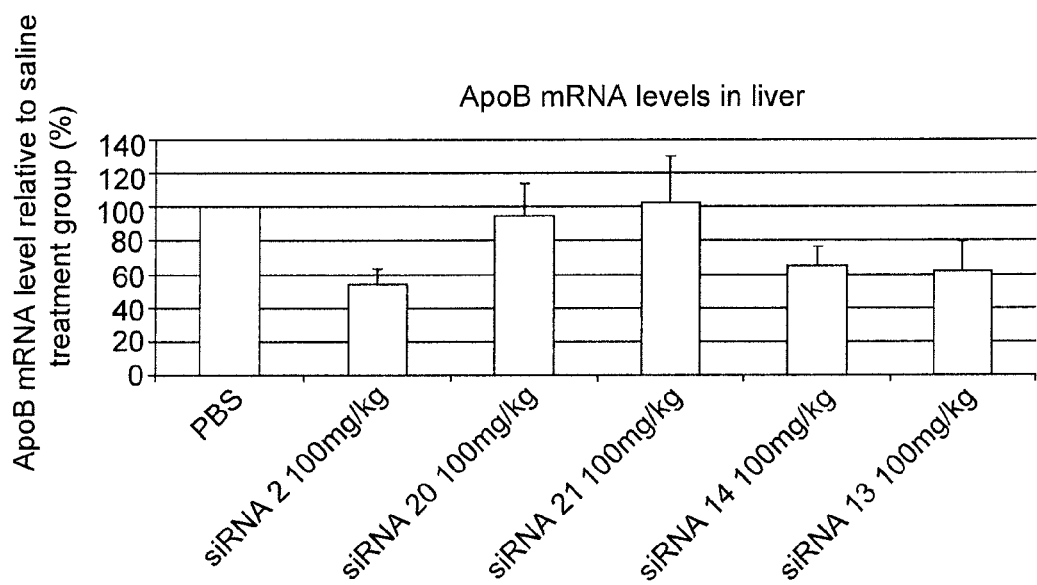
FIG. 8 is a bar graph comparing the apo gene silencing in the liver upon treatment with cholesterol, PEG, vitamin E and cholanic acid conjugated siRNAs.

In vivo liver apoB gene silencing of cholesterol, PEG, vitamin E and cholanic acid conjugated siRNAs were evaluated, the results of which are depicted in FIG. 8. Female C57/BL6 mice 6-8 weeks old; 6 mice/group; iv injection 100 mg/kg; sacrificed 72 h after injection. siRNA 2, siRNA 20, siRNA 21, siRNA14, and siRNA 13, as depicted in the Table 1 above, were used in this study.

Figure 9:
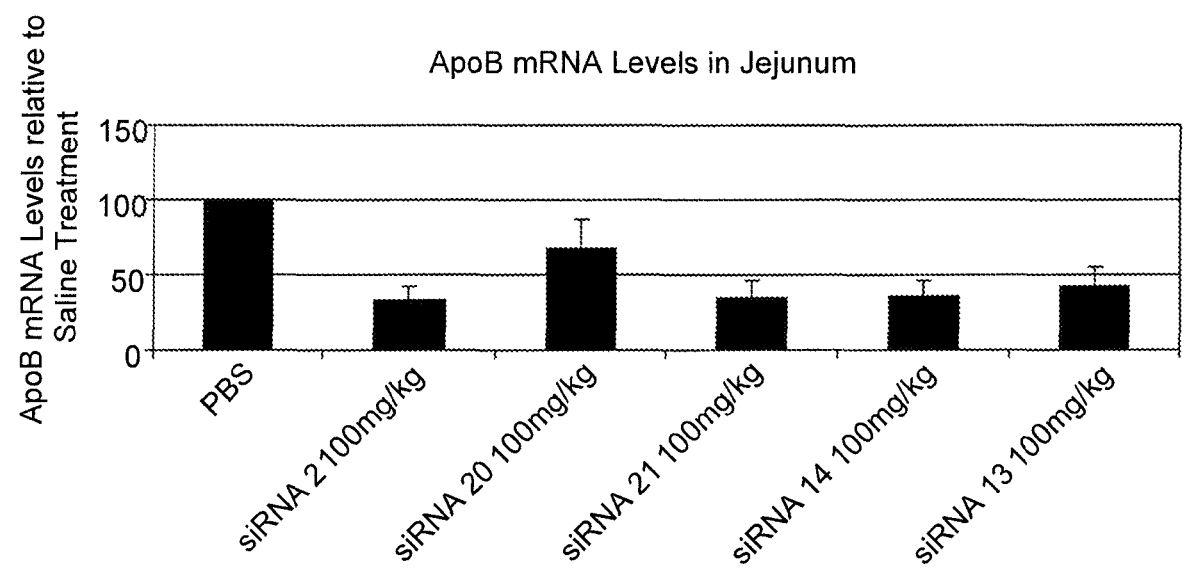
FIG. 9 is a bar graph comparing the apo gene silencing in the jejunum upon treatement with cholesterol, PEG, vitamin E and cholanic acid conjugated siRNAs.

In vivo jejunum apoB gene silencing of cholesterol, PEG, vitamin E and cholanic acid conjugated siRNAs were evaluated, the results of which are depicted in FIG. 9. Female C57/BL6 mice 6-8 weeks old; 6 mice/group; iv injection 100 mg/kg; sacrificed 72 h after injection. siRNA 2, siRNA 20, siRNA 21, siRNA 14, and siRNA 13, as depicted in the Table 1 above, were used in this study.

Figure 10A:
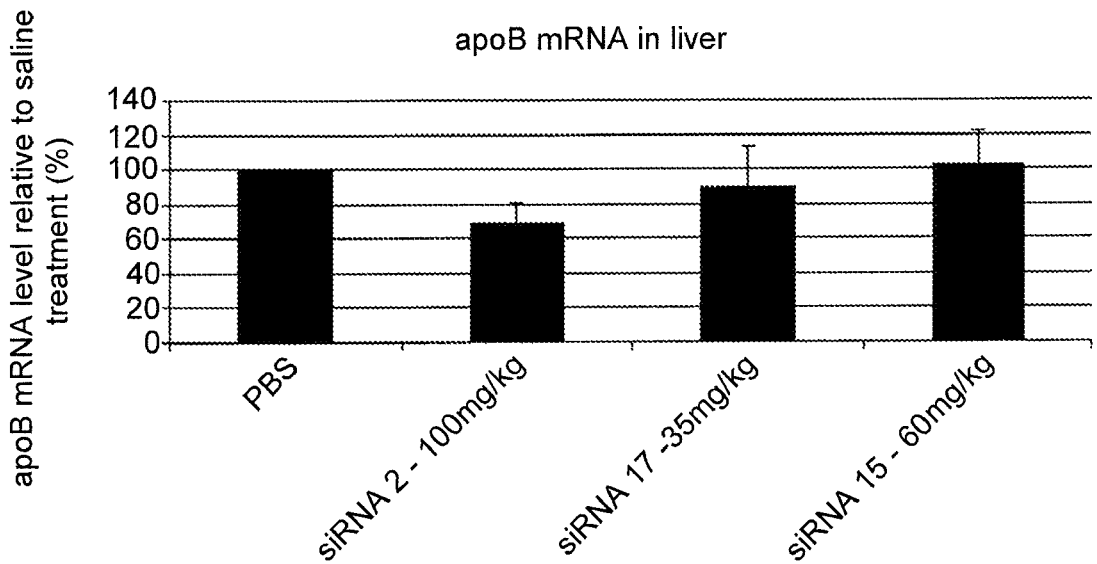
FIG. 10 is a bar graph depicting the percentage of apoB mRNA relative to saline in liver and jejunum respectively upon treatment with cholesterol, dialkylglyceride and lithocholamide conjugated siRNAs.
Figure 10B:
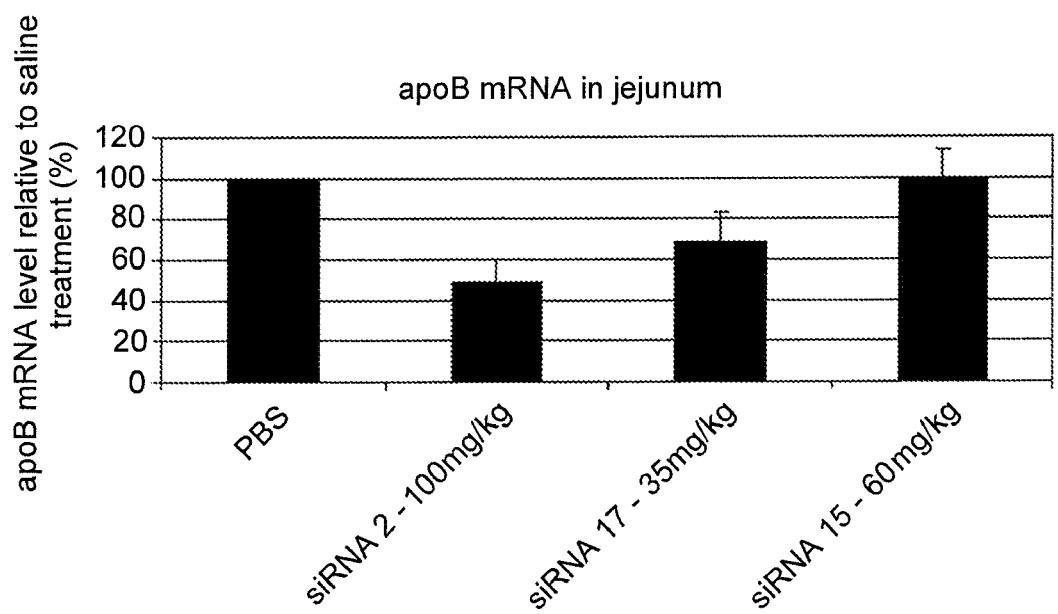

In vivo apoB gene silencing of cholesterol, dialkylglyceride and lithocholamide conjugated siRNAs were evaluated in liver and jejunum, the results of which are depicted in FIGS. 10A and 10B respectively. Female C57/BL6 mice 6-8 weeks old; 6 mice/group; iv injection. siRNA 2, siRNA 17, and siRNA 15, as depicted in the Table 1 above, were used in this study.

Figure 11:
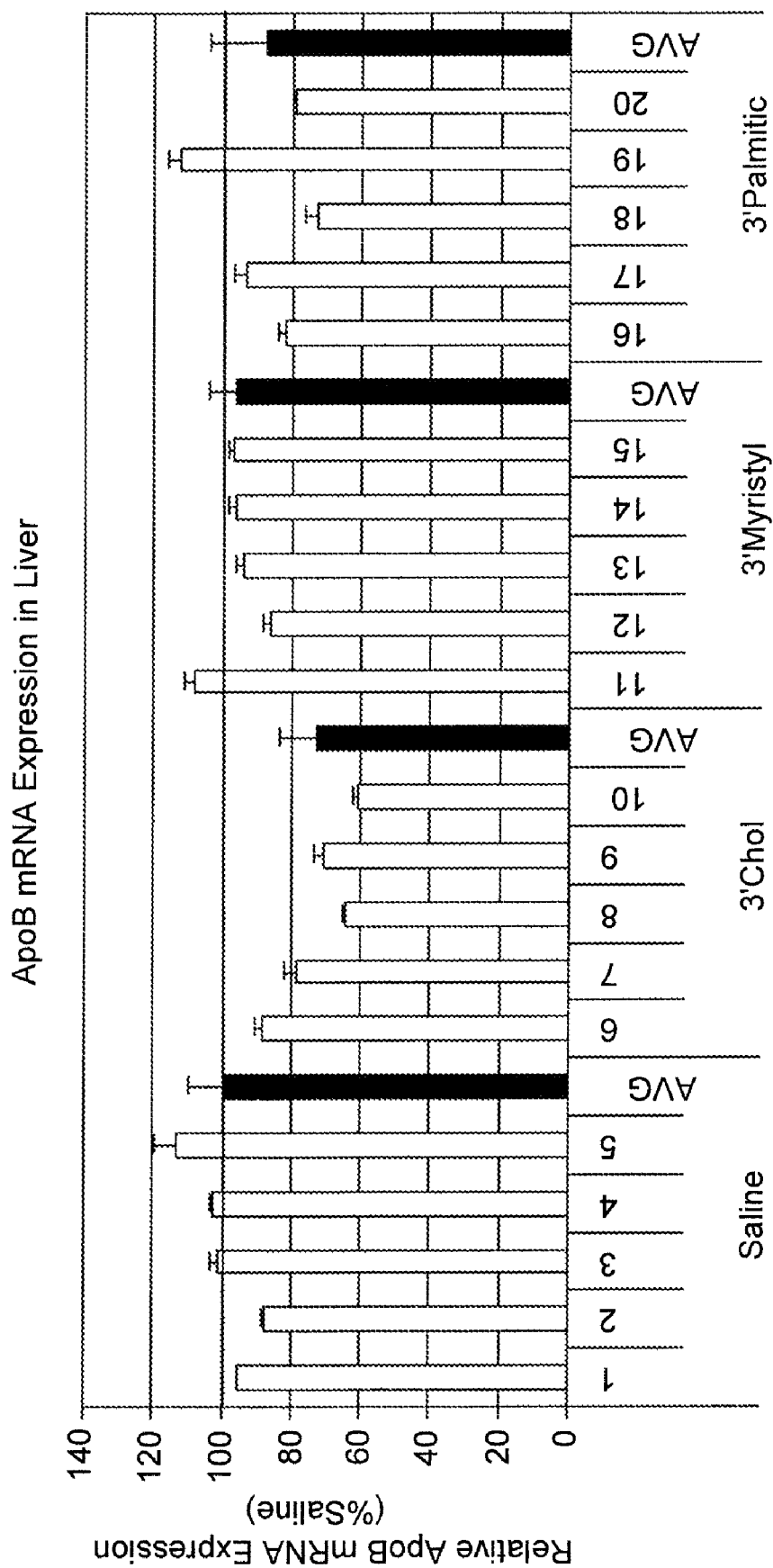
FIG. 11 is a bar graph depicting the percentage of relative apoB mRNA in liver upon treatement with saline, siRNA 2, siRNA 5, and siRNA 6.
Figure 12:
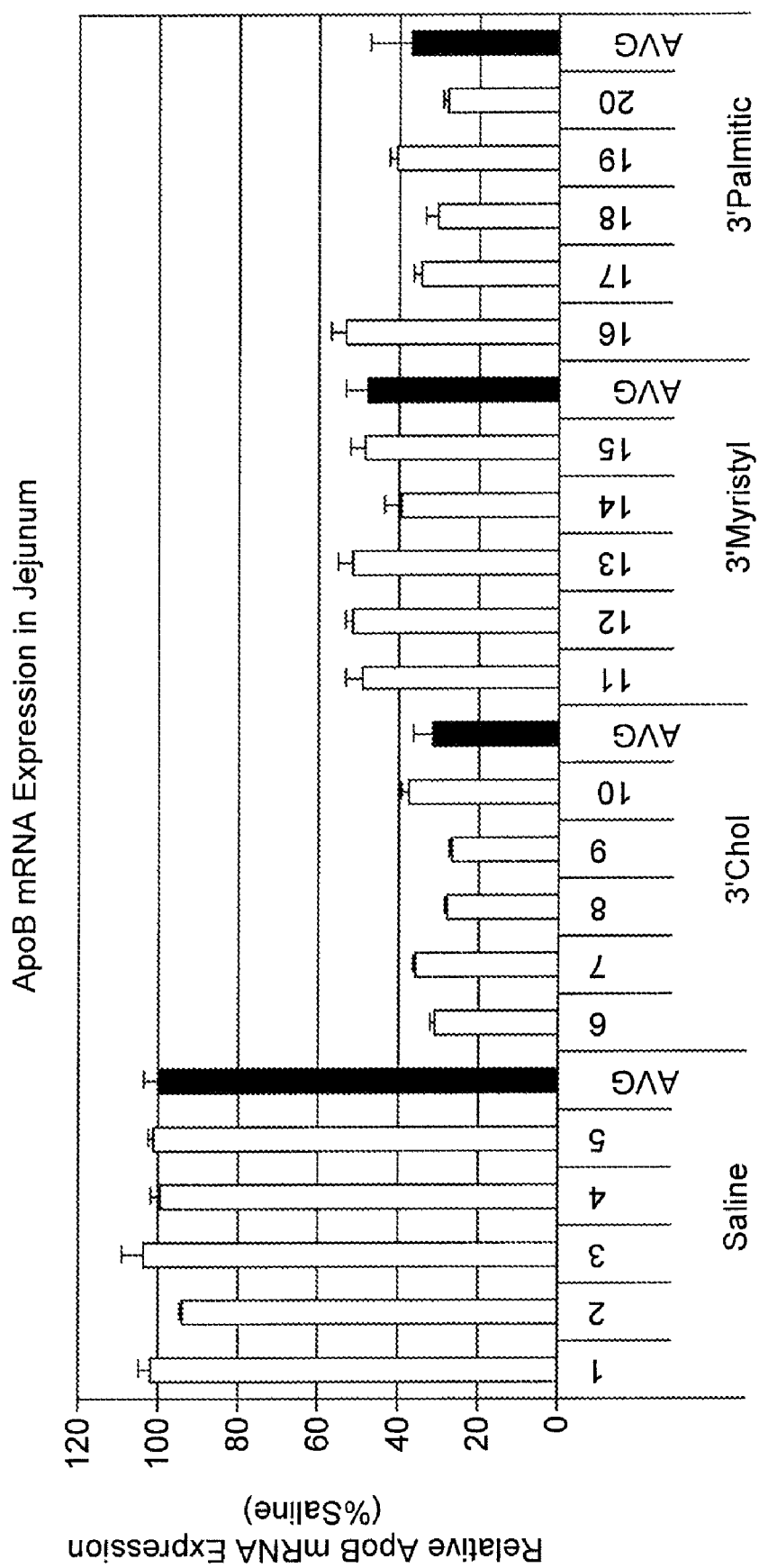
FIG. 12 is a bar graph depicting the percentage of relative apoB mRNA in jejunum upon treatement with saline, siRNA 2, siRNA 5, and siRNA 6.

Relative apoB mRNA expression in liver was evaluated after treatment once daily for three days at 50 mg/kg of saline, siRNA 2, siRNA 5, and siRNA 6, as depicted in the Table 1 above. The results are depicted in FIG. 11. Relative apoB mRNA expression in jejunum was evaluated after treatment once daily for three days at 50 mg/kg of saline, siRNA 2, siRNA 5, and siRNA 6, as depicted in the Table above. The results are depicted in FIG. 12.

Example 5 siRNA-PEG Conjugate or Pegylated siRNA

TABLE 2

Oligonucleotide-PEG conjugate: Analytical data

| Seq No | Sequence 5'-3' | Modifications | MW Expected | MW* Obs. | HPLC Retention time |
|---|---|---|---|---|---|
| 3194 | GCACAUAGGAGAGAUGACGUUs-HP-NH$_2$ (SEQ ID NO: 17) | Hydroxyprolinol amine | 7107.46 | 7107.2 | 37.497 |
| 3195 | GCACAUAGGAGAGAUGACGUUs-HP-NH$_2$-20KPEG (SEQ ID NO: 18) | Hydroxyprolinol amine, 20K PEG | 27213.19 | 27718-29656 | 31.283 |
| 3164 | GsUCAUCACACUGAAUACCAAU-HP-NH$_2$ (SEQ ID NO: 19) | Hydroxyprolinol amine | 6932.33 | 6932.15 | 19.733 |
| 3170 | GsUCAUCACACUGAAUACCAAU-HP-NH-5KPEG (SEQ ID NO: 20) | Hydroxyprolinol amine, 5K PEG | 11746.19 | 11906-13316 | 16.822 |
| 3171 | GsUCAUCACACUGAAUACCAAU-HP-NH-20KPEG (SEQ ID NO: 21) | Hydroxyprolinol amine, 20K PEG | 26746.19 | 28116-2935 | 16.164 |
| 2936 | NH$_2$-HP-CUUACGCUGAGUACUUCGAdTsdT (SEQ ID NO: 22) | Hydroxyprolinol amine | 6915.3 | 6915.01 | 20.506 |
| 3187 | 5KPEG-NH-HP-CUUACGCUGAGUACUUCGAdTsdT (SEQ ID NO: 23) | Hydroxyprolinol amine, 5K PEG | 12021.46 | 11847-13256 | 17.829 |
| 3188 | 20KPEG-NH-HP-CUUACGCUGAGUACUUCGAdTsdT (SEQ ID NO: 24) | Hydroxyprolinol amine, 20K PEG | 27021.46 | 27440-29289 | 16.921 |
| 2937 | CsUUACGCUGAGUACUUCGAdTdT-HP-NH$_2$ (SEQ ID NO: 25) | Hydroxyprolinol amine | 6915.3 | 6915.06 | 20.537 |
| 3172 | CsUUACGCUGAGUACUUCGAdTdT-HP-NH-5KPEG (SEQ ID NO: 26) | Hydroxyprolinol amine, 5K PEG | 12021.46 | 11932-13342 | 17.578 |
| 3173 | CsUUACGCUGAGUACUUCGAdTdT-HP-NH-20KPEG (SEQ ID NO: 27) | Hydroxyprolinol amine, 20K PEG | 27021.46 | 27967-29865 | 17.087 |

PEGylation of siRNA

General. The reagent solutions for RNA synthesis were made from products of the Aldrich Chemical Co. The phosphoramidites were products of Pierce Nucleic Acid Technologies. The hydroxyprolinol-phthalamideamine supports were synthesized in-house. The PEG was a product of NOF Corp. Ion exchange preparative chromatography was performed on TSKgel-SuperQ-5PW (Tosoh). Ion exchange analytical chromatography was performed on a DNAPac Pa100 (Dionex). Electron spray ionization mass spectra were recorded with an Agilent 1100 MSD-SL.

HPLC Techniques. The RNA was analyzed by ion-exchange chromatography (column, DNAPac Pa100, 4×250 mm, analytical), heated to 30° C., flow rate 1.5 mL min$^{-1}$, buffer A=0.02°M Na$_2$HPO$_4$ in 10% CH$_3$CN, pH 11; buffer B=buffer A+1 M NaBr in 10% CH$_3$CN, pH 11, linear gradient from 0 to 75% in 53 min. The LC/ESI-MS conditions were as follows: column XTerra C8 (2.1×30 mm, 2.5 µm), linear gradient from 5 to 35% in 2 min and from 35 to 70% in 30.5 min, flow rate 0.200 mL min$^{-1}$, buffer A=400 mM HFIP/16.3 mM TEA in H$_2$O, buffer B=100% methanol. The RNA was purified by ion-exchange chromatography (5 cm in-house packed column, TSKgel-SuperQ-5PW, 20 µm), heated to 75° C., flow rate 50 mL min$^{-1}$, buffer A=0.020M Na$_2$HPO$_4$ in 10% CH$_3$CN, pH 8.5; buffer B=buffer A+1 M NaBr in 10% CH$_3$CN, pH 8.5, linear gradient from 20 to 55% in 120 min.

RNA synthesis. The protected RNA was assembled on an AKTA Oligo Pilot 100 on a 100-150 µmol scale using custom in-house support and phosphoramidite chemistry. Phosphoramidites were used as 0.2 mol L$^{-1}$ solutions in dry CH$_3$CN, with a 900 s coupling time and the manufacturer's recommended synthesis protocols were used. After synthesis, the support-bound RNA was treated with aqueous CH$_3$NH$_2$ (40%) for 90 minutes at 45° C., cooled, filtered and washed with DMSO (3×40 mL). The filtrate was then treated with TEA.3HF (60 mL) for 60 minutes at 40° C., and quenched with aq. NaOAc (0.05M, pH 5.5, 200 mL). The synthesis was followed by analytical ion-exchange HPLC, preparative HPLC, then desalting on Sephadex G-25.

PEG Conjugation.

A) Initial reaction conditions. The purified and desalted RNA was lyophilized. RNA (1 mg) was dissolved in aq NaHCO$_3$ (0.1M, 200L, pH 8.1) and DMF (200L each). 5 K (13 equivalents, 10 mg) or 20 KPEG (3.4 equivalents, 10 mg, Sunbright ME-20°HS, NOF Corp.) was added directly to reaction vial and vortexed thoroughly. The reaction was continued overnight at 4° C., and was followed by analytical ion-exchange HPLC. When the reaction reached >85% completion, it was quenched with aq. NaOAc (0.05M, pH 5.5) until the pH was ~7.

B) Borate buffer conjugation. The purified and desalted RNA was lyophilized. A sample of RNA (1 mg) was dissolved in sodium borate buffer (200 µL, 0.05M, pH10). 5KPEG (3 mg, 4.5 equivalents Sunbright ME-50HS, NOF Corp.) was dissolved in CH$_3$CN (200 µL). The RNA solution was added to the PEG solution and vortexed thoroughly. The reaction continued for one hour at room temperature, and was followed by analytical ion-exchange HPLC. When reaction reached >85% completion, it was quenched with aq. NaOAc (0.05M, pH 5.5) until the pH was ~7.

C) PEG linker (AS and HS) comparison (Figure Exp-1). A sample of RNA (1 mg) was dissolved in aq. NaHCO$_3$ (0.1M, 200L, pH 8.1) and DMF (200L). 5 KPEG (13.5 eq, 10 mg, Sunbright ME-5°HS or Sunbright ME-50AS, NOF Corp.) was added directly to the reaction vial and vortexed thoroughly. The reaction continued overnight at 4° C., and was followed by analytical ion-exchange HPLC. When the reaction reached >85% completion, it was quenched with aq. NaOAc (0.05M, pH 5.5) until the pH was ~7.

D) Final optimized PEG conjugation. The purified and desalted RNA was lyophilized. A sample of RNA (50 mg) was dissolved in aq. NaHCO$_3$ (0.1M, 2 mL pH 8.1) and DMF (1 mL). 20KPEG (2.7 eq, 400-520 mg Sunbright ME-200HS, NOF Corp.) was dissolved in CH$_3$CN (2 mL). The RNA solution was added to the PEG solution and vortexed thoroughly. H$_2$O (250 mL) was added to the reaction to decrease turbidity. The reaction continued for one hour at room temperature, and was followed by analytical ion-exchange HPLC. When the reaction reached >85% completion, it was quenched with aq. NaOAc (0.05M, pH 5.5) until the pH was ~7.

PEG Starting Material Structure.

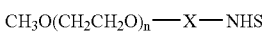
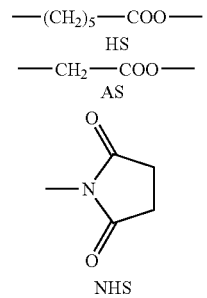

X = HS or AS

Structure of mPEG-NHS ester used for postsynthetic conjugation to siRNA

Exemplary PEGylated siRNAs are provided in Table 3 below:

TABLE 3

PEGylated siRNAs

| Target | Duplex | Sequence | SEQ ID No: | Ligand |
|---|---|---|---|---|
| ApoB | 5167 | 5'-GUCAUCACACUGAAUACCAAU$_s$Hyp-Chol-3' | 28 | Cholesterol |
|  |  | 5'-AUUGGUAUUCAGUGUGAUGAc$_s$a$_s$C-3' | 2 |  |
| ApoB | 3027 | 5'-GsUCAUCACACUGAAUACCAAU-Hyp-PEG5K | 29 | PEG-5K |
|  |  | 5'-AUUGGUAUUCAGUGUGAUGAc$_s$a$_s$C-3' | 2 |  |
| ApoB | 3028 | 5'-GsUCAUCACACUGAAUACCAAU-Hyp-PEG20K | 30 | PEG-20K |
|  |  | 5'-AUUGGUAUUCAGUGUGAUGAc$_s$a$_s$C-3' | 2 |  |
| ApoB | 3245 | 5'-GsUCAucAcAcuGAAuAccAAU-Hyp-PEG40K-3' | 31 | PEG-40K |
|  |  | 5'-AUUGGUAUUCAGUGUGAUGAc$_s$a$_s$C-3' | 2 |  |
| Luc | 3246 | 5'-CsUUACGCUGAGUACUUCGAdTdT-Hyp-PEG5K | 32 | PEG-5K |
|  |  | 5'-UCGAAGUACUCAGCGUAAGdTdT-3' | 33 |  |
| Luc | 3247 | 5'-CsUUACGCUGAGUACUUCGAdTdT-Hyp-PEG20K | 34 | PEG-20K |
|  |  | 5'-UCGAAGUACUCAGCGUAAGdTdT-3' | 33 |  |
| Luc | 3248 | 5'-CsUUACGCUGAGUACUUCGAdTdT-Hyp-PEG40K-3' | 35 | PEG-40K |
|  |  | 5'-UCGAAGUACUCAGCGUAAGdTdT-3' | 33 |  |
| Luc | 1695 | 5'-CUUACGCUGAGUACUUCGAdTdT-Hyp-Chol-3' | 36 | Cholesterol |
|  |  | 5'-UCGAAGUACUCAGCGUAAGdTdT-3' | 33 |  |

Figure 13:
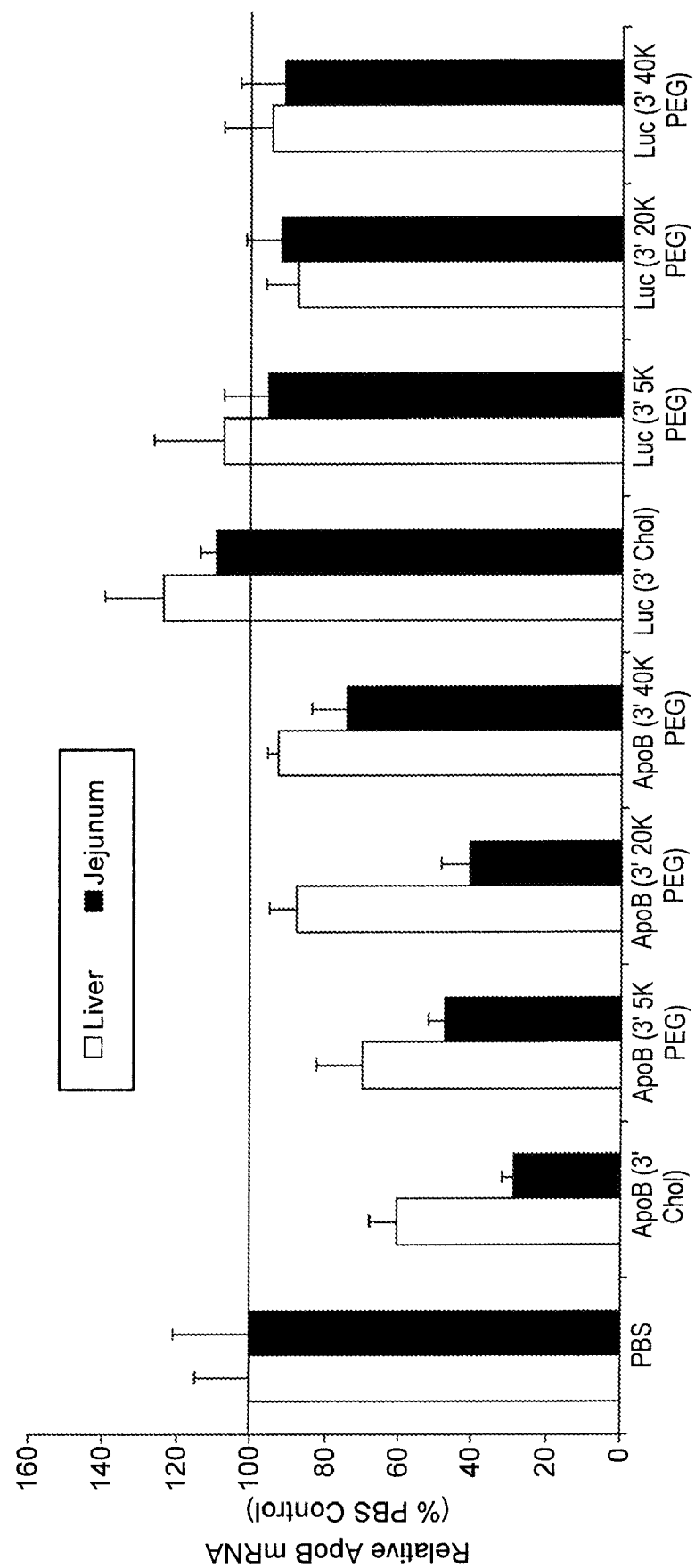
FIG. 13 is a bar graph depicting the percentage of relative apoB mRNA in liver and Jejunum upon treatment with PBS and other exemplified PEG conjugated siRNA.

Relative ApoB mRNA was evaluated in Liver and Jejunum with dosing of PEG siRNA conjugates as provided in Table 3 above, using procedures similar to those described in Example 4. The results are depicted in FIG. 13.

Example 6

In Vivo Down-Modulation of Endogenous CNPase mRNA Levels by CNS Administration of Lipophilic Conjugates of siRNAs Targeting CNPase in Rats To assess the in vivo biological activity of lipophilic conjugates of siRNAs in the CNS, including, behenoyl, lithocholic acid, dialkylglyceride, and Vitamin E conjugated siRNAs targeting CNPase (2',3'-cyclic nucleotide 3'-phosphodiesterase), a gene expressed specifically in oligodendrocytes within the CNS, dsRNAs AD-3236, AD-3237, AD-3238, AD-3181, AD-3282 and AD-3178 (Table 4) were synthesized in which liphophilic molecules were placed on the 3'-end of the sense strand (outside of the dsRNA's nucleotide region that targets the CNPase mRNA).

TABLE 4

Sequences of dsRNAs AD-3236, AD-3237, AD-3238, AD-3181, AD-3182 and AD-3178

| Duplex name | Sense strand sequence(5"-3") | SEQ ID NO: | Antisense strand sequence (5"-3") | SEQ ID NO: |
|---|---|---|---|---|
| AD-3236 | GGccuuGAccucuuAGAGATT-Behenoyl | 37 | UCUCuAAGAGGUcAAGGCCTsT | 38 |
| AD-3237 | GGccuuGAccucuuAGAGATT-Lithocholic acid | 39 | UCUCuAAGAGGUcAAGGCCTsT | 38 |
| AD-3238 | GGccuuGAccucuuAGAGATT-Dialkylglycerides | 40 | UCUCuAAGAGGUcAAGGCCTsT | 38 |
| AD-3181 | GGccuuGAccucuuAGAGATT-Vitamin E | 41 | UCUCuAAGAGGUcAAGGCCTsT | 38 |
| AD-3182 | GGccuuGAccucuuAGAGATT-Stearoyl | 42 | UCUCuAAGAGGUcAAGGCCTsT | 38 |
| AD-3178 | GGccuuGAccucuuAGAGATT-cholesterol | 43 | UCUCuAAGAGGUcAAGGCCTsT | 38 |

In rats, different amounts of siRNA or phosphate-buffered saline (PBS, vehicle control) was administered by continuous intraparenchymal infusion into the corpus callosum over 3 days. Male Sprague-Dawley rats, approximately 250-300 g body weight, received stereotaxic implantation of 30-gauge infusion cannulae (Plastics One, Roanoke, Va.) such that unilateral infusions were targeted to the corpus callosum (anteroposterior +0.7 mm, mediolateral +2.2 mm, relative to bregma; dorsoventral −3 mm, relative to skull surface). Mini-osmotic pumps (manufactured by Alzet, Inc. model 2ML1) were primed overnight according to the manufacturer's specifications, implanted subcutaneously, and connected via catheters, to deliver (6 rats per treatment group) PBS or different concentrations of siRNAs at 10 uL/hr over 3 days. At the end of the 3 day infusion period, animals were sacrificed, brains were removed, and ipsilateral corpus callosum encompassing the infusion site was dissected. 1 mm thick coronal brain slabs were obtained over a distance of 12 mm anterior to posterior and then ipsilateral corpus callosum tissue samples were collected from each brain slab. Tissue was flash frozen and then stored at −80° C. For branched DNA analysis, frozen corpus callosum tissue pieces were lysed in 1 ml of Tissue and Cell Lysis solution (Epicentre, Madison, Wis.) containing Proteinase K (Ambion, Austin, Tex.). CNPase and MBP (myelin basic protein) mRNA were quantified using the Quantigene Explore Kit according to the manufacturer's instructions (Panomics, Fremont, Calif.). For each tissue sample, the ratio of CNPase/MBP (normalized CNPase mRNA level) was calculated as an average of three determinations. These average ratios from each individual animal were then averaged to obtain a group (treatment) average.

The siRNA duplexes, AD-3236, AD-3237 and AD-3238 were found to be effective in vivo in down-modulating CNPase mRNA levels after intraparenchymal CED infusion with 2.16 mg over 3 days (10 uL/hr at 3 mg/ml) in rats. AD-3236, AD-3237, and AD3238 reduced the normalized CNPase mRNA levels (normalized to MBP) in corpus callosum tissue by 39%, 28% and 42%, respectively, relative to the PBS control group. Similarly, intraparenchymal CNS infusion of the Vitamin E conjugated siRNA AD-3181 and Stearoyl conjugated siRNA AD-3182 over 3 days (also 10 ul/hr at 3 mg/ml for a total of 2.16 mg administered dose) reduced CNP mRNA levels (normalized to MBP) by 41% and 51% respectively compared to PBS control animals. These results demonstrate that the different lipophilic conjugated siRNAs AD-3222, AD-3236, AD-3237, AD-3238, AD-3181 and AD-3182 following intraparenchymal CNS infusion down-modulate CNPase mRNA levels within the corpus callosum.

The invention claimed is:

1. An iRNA agent comprising a first strand and a second strand, wherein at least one subunit having a formula (II) is incorporated into at least one of said strands, and at least one of said strands leads to the cleavage of a complementary target sequence via a RISC dependent mechanism:

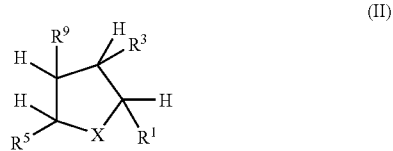
(II)

wherein:
X is NC(O)R$^7$, or NR$^7$;
R$^3$ and R$^9$ are each independently H, OH, OR$^a$, or OR$^b$, provided that at least one of R$^3$ or R$^9$ is OH, OR$^a$, or OR$^b$;
R$^5$ is H or C$_1$-C$_6$ alkyl;
R$^1$ is CH$_2$OH or CH$_2$OR$^b$, provided that at least one of R$^1$, R$^3$, or R$^9$ is OR$^b$ or CH$_2$OR$^b$;
R$^7$ is C$_1$-C$_{20}$ alkyl substituted with NR$^c$R$^d$ or NHC(O)R$^d$;

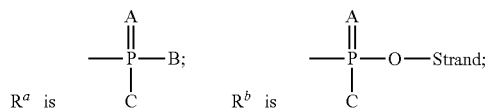

each of A and C is, independently, O or S; and

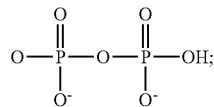

B is OH, O$^-$, or
R$^c$ is H or C$_1$-C$_6$ alkyl; and
R$^d$ is a bile acid radical, a fatty acid conjugate radical or PEG.

2. The compound of claim 1, wherein R$^1$ is CH$_2$OR$^b$ and R$^9$ is OH.
3. The compound of claim 2, wherein R$^1$ and R$^9$ are trans.
4. The compound of claim 3, wherein A is O.
5. The compound of claim 3, wherein A is S.
6. The compound of claim 1, wherein R$^7$ is (CH$_2$)$_5$NHR$^d$ or (CH$_2$)$_5$NHC(O)R$^d$.
7. The compound of claim 1, wherein R$^d$ is lithocholic-oleyl, lauroyl, docosanoyl, stearoyl, palmitoyl, myristoyl, oleoyl, linoleoyl or dodecanoyl.
8. The compound of claim 1, wherein R$^d$ is lauroyl.
9. The compound of claim 1, wherein R$^d$ is dodecanoyl.
10. The compound of claim 1, wherein R$^d$ is stearoyl.
11. The compound of claim 1, wherein R$^d$ is palmitoyl.
12. The compound of claim 1, wherein R$^d$ is myristoyl.
13. The compound of claim 1, wherein R$^d$ is oleoyl.
14. The compound of claim 1, wherein R$^d$ is linoleoyl.
15. The compound of claim 1, wherein R$^d$ is lithocholic-oleyl.
16. The compound of claim 1, wherein R$^d$ is docosanoyl.
17. The compound of claim 1, wherein R$^d$ is PEG.
18. The compound of claim 1, wherein R$^d$ is PEG-5K.
19. The compound of claim 1, wherein R$^d$ is PEG-20K.
20. The compound of claim 1, wherein R$^d$ is PEG-40K.
21. An iRNA agent comprising a first strand and a second strand, wherein at least one subunit having a formula (II) is incorporated into at least one of said strands, and at least one of said strands leads to the cleavage of a complementary target sequence via a RISC dependent mechanism:

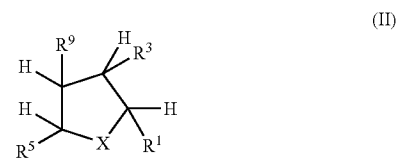
(II)

wherein:
X is NC(O)R$^7$, or NR$^7$;
each of R$^3$, R$^5$ and R$^9$ is, independently, H, OH, OR$^a$, or OR$^b$, provided that at least one of R$^3$, R$^5$, or R$^9$ is OH, OR$^a$, or OR$^b$;
R$^1$ is CH$_2$OH or CH$_2$OR$^b$, provided that at least one of R$^1$, R$^3$, R$^5$, or R$^9$ is OR$^b$ or CH$_2$OR$^b$;
R$^7$ is C$_1$-C$_{20}$ alkyl substituted with NR$^c$R$^d$ or NHC(O)R$^d$;

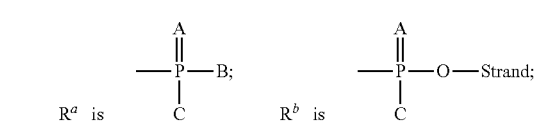

each of A and C is, independently, O or S; and

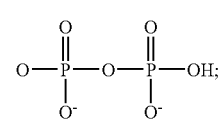

B is OH, O$^-$, or
R$^c$ is H or C$_1$-C$_6$ alkyl; and
R$^d$ is a bile acid radical, a fatty acid conjugate radical or PEG.

22. The compound of claim 21, wherein R$^1$ is CH$_2$OR$^b$ and R$^9$ is OH.
23. The compound of claim 21, wherein R$^7$ is (CH$_2$)$_5$NHR$^d$ or (CH$_2$)$_5$NHC(O)R$^d$.
24. The compound of claim 21, wherein R$^d$ is lithocholic-oleyl, lauroyl, docosanoyl, stearoyl, palmitoyl, myristoyl, oleoyl, linoleoyl or dodecanoyl.
25. The compound of claim 21, wherein R$^d$ is PEG, PEG-5K, PEG-20K, or PEG-40K.

* * * * *

SEQUENCE LISTING

<160> NUMBER OF SEQ ID NOS: 44

<210> SEQ ID NO 1
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / 4-hydroxyprolinol amino- linker (Hyp).

<400> SEQUENCE: 1
gucaucacac ugaauaccaa n                                                         21

<210> SEQ ID NO 2
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 21, 22
<223> OTHER INFORMATION: / 2'-O-methyl sugar modification
      phosphorothioate linkage corresponding base

<400> SEQUENCE: 2
auugguauuc agugugauga nnc                                                       23

<210> SEQ ID NO 3
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Liophile (L1) is conjugated to 3'-end of
      sense strand of the apoB siRNA via trans-4-hydroxyprolinol linker
      (Hyp)

<400> SEQUENCE: 3
gucaucacac ugaauaccaa n                                                         21

<210> SEQ ID NO 4
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Liophile (L2 is conjugated to 3'-end of sense
      strand of the apoB siRNA via trans-4-hydroxyprolinol linker (Hyp)

<400> SEQUENCE: 4
gucaucacac ugaauaccaa n                                                         21

<210> SEQ ID NO 5
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Liophile (L3 is conjugated to 3'-end of sense
      strand of the apoB siRNA via trans-4-hydroxyprolinol linker (Hyp)

-continued

```
<400> SEQUENCE: 5
gucaucacac ugaauaccaa n                                              21

<210> SEQ ID NO 6
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Liophile (L4 is conjugated to 3'-end of sense
      strand of the apoB siRNA via trans-4-hydroxyprolinol linker (Hyp)

<400> SEQUENCE: 6
gucaucacac ugaauaccaa n                                              21

<210> SEQ ID NO 7
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Liophile (L5 is conjugated to 3'-end of sense
      strand of the apoB siRNA via trans-4-hydroxyprolinol linker (Hyp)

<400> SEQUENCE: 7
gucaucacac ugaauaccaa n                                              21

<210> SEQ ID NO 8
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Liophile (L6 is conjugated to 3'-end of sense
      strand of the apoB siRNA via trans-4-hydroxyprolinol linker (Hyp)

<400> SEQUENCE: 8
gucaucacac ugaauaccaa n                                              21

<210> SEQ ID NO 9
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
```

```
<221> NAME/KEY: misc_binding
<222> LOCATION: 21
<223> OTHER INFORMATION: / Liophile (L7 is conjugated to 3'-end of sense
      strand of the apoB siRNA via trans-4-hydroxyprolinol linker (Hyp)

<400> SEQUENCE: 9
gucaucacac ugaauaccaa n                                              21

<210> SEQ ID NO 10
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Liophile (L8 is conjugated to 3'-end of sense
      strand of the apoB siRNA via trans-4-hydroxyprolinol linker (Hyp)

<400> SEQUENCE: 10
gucaucacac ugaauaccaa n                                              21

<210> SEQ ID NO 11
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Liophile (L9 is conjugated to 3'-end of sense
      strand of the apoB siRNA via trans-4-hydroxyprolinol linker (Hyp)

<400> SEQUENCE: 11
gucaucacac ugaauaccaa n                                              21

<210> SEQ ID NO 12
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Liophile (L10 is conjugated to 3'-end of
      sense strand of the apoB siRNA via trans-4-hydroxyprolinol linker
      (Hyp)

<400> SEQUENCE: 12
gucaucacac ugaauaccaa n                                              21

<210> SEQ ID NO 13
<211> LENGTH: 21
<212> TYPE: RNA
<213> ORGANISM: Artificial Sequence
<220> FEATURE:
```

```
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Liophile (L11 is conjugated to 3'-end of
      sense strand of the apoB siRNA via trans-4-hydroxyprolinol linker
      (Hyp)

<400> SEQUENCE: 13
gucaucacac ugaauaccaa n                                              21

<210> SEQ ID NO 14
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Liophile (L12 is conjugated to 3'-end of
      sense strand of the apoB siRNA via trans-4-hydroxyprolinol linker
      (Hyp)

<400> SEQUENCE: 14
gucaucacac ugaauaccaa n                                              21

<210> SEQ ID NO 15
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Liophile (L13 is conjugated to 3'-end of
      sense strand of the apoB siRNA via trans-4-hydroxyprolinol linker
      (Hyp)

<400> SEQUENCE: 15
gucaucacac ugaauaccaa n                                              21

<210> SEQ ID NO 16
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Liophile (L14 is conjugated to 3'-end of
      sense strand of the apoB siRNA via trans-4-hydroxyprolinol linker
      (Hyp)

<400> SEQUENCE: 16
```
gucaucacac ugaauaccaa n                                              21

<210> SEQ ID NO 17
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Hydroxyprolinol amine

<400> SEQUENCE: 17
gcacauagga gagaugacgu n                                              21

<210> SEQ ID NO 18
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / Hydroxyprolinol amine, 20K PEG

<400> SEQUENCE: 18
gcacauagga gagaugacgu n                                              21

<210> SEQ ID NO 19
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = guanine phosphorothioate linkages
<220> FEATURE:
<221> NAME/KEY: misc_binding
<222> LOCATION: 21
<223> OTHER INFORMATION: / Hydroxyprolinol amine

<400> SEQUENCE: 19
nucaucacac ugaauaccaa u                                              21

<210> SEQ ID NO 20
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = guanine phosphorothioate linkages
<220> FEATURE:
<221> NAME/KEY: misc_binding
<222> LOCATION: 21
<223> OTHER INFORMATION: / Hydroxyprolinol amine, 5KPEG

```
<400> SEQUENCE: 20
nucaucacac ugaauaccaa u                                              21

<210> SEQ ID NO 21
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = guanine phosphorothioate linkages
<220> FEATURE:
<221> NAME/KEY: misc_binding
<222> LOCATION: 21
<223> OTHER INFORMATION: / Hydroxyprolinol amine, 20KPEG

<400> SEQUENCE: 21
nucaucacac ugaauaccaa u                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_binding
<222> LOCATION: 1
<223> OTHER INFORMATION: / Hydroxyprolinol amine
<220> FEATURE:
<221> NAME/KEY: misc_feature
<222> LOCATION: 20
<223> OTHER INFORMATION: n = deoxythymidine, phosphorothioate linkage
<220> FEATURE:
<221> NAME/KEY: misc_feature
<222> LOCATION: 21
<223> OTHER INFORMATION: n = deoxythymidine

<400> SEQUENCE: 22
cuuacgcuga guacuucgan n                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_binding
<222> LOCATION: 1
<223> OTHER INFORMATION: / Hydroxyprolinol amine,5K PRG
<220> FEATURE:
<221> NAME/KEY: misc_feature
<222> LOCATION: 20
<223> OTHER INFORMATION: n = deoxythymidine, phosphorothioate linkage
<220> FEATURE:
<221> NAME/KEY: misc_feature
<222> LOCATION: 21
<223> OTHER INFORMATION: n = deoxythymidine

<400> SEQUENCE: 23
cuuacgcuga guacuucgan n                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetically generated oligonucleotide
```

```
<220> FEATURE:
<221> NAME/KEY: misc_binding
<222> LOCATION: 1
<223> OTHER INFORMATION: / Hydroxyprolinol amine, 20K PEG
<220> FEATURE:
<221> NAME/KEY: misc_feature
<222> LOCATION: 20
<223> OTHER INFORMATION: n = deoxythymidine, phosphorothioate linkage
<220> FEATURE:
<221> NAME/KEY: misc_feature
<222> LOCATION: 21
<223> OTHER INFORMATION: n = deoxythymidine

<400> SEQUENCE: 24
cuuacgcuga guacuucgan n                                            21

<210> SEQ ID NO 25
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: cytadine phosphorothioate linkage
<220> FEATURE:
<221> NAME/KEY: misc_feature
<222> LOCATION: 20, 21
<223> OTHER INFORMATION: n = deoxythymidine
<220> FEATURE:
<221> NAME/KEY: misc_binding
<222> LOCATION: 21
<223> OTHER INFORMATION: / Hydroxyprolinol amine

<400> SEQUENCE: 25
nuuacgcuga guacuucgan n                                            21

<210> SEQ ID NO 26
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: cytadine phosphorothioate linkage
<220> FEATURE:
<221> NAME/KEY: misc_feature
<222> LOCATION: 20, 21
<223> OTHER INFORMATION: n = deoxythymidine
<220> FEATURE:
<221> NAME/KEY: misc_binding
<222> LOCATION: 21
<223> OTHER INFORMATION: / Hydroxyprolinol amine, 5K PEG

<400> SEQUENCE: 26
nuuacgcuga guacuucgan n                                            21

<210> SEQ ID NO 27
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: cytadine phosphorothioate linkage
<220> FEATURE:
<221> NAME/KEY: misc_feature
<222> LOCATION: 20, 21
```

-continued

```
<223> OTHER INFORMATION: n = deoxythymidine
<220> FEATURE:
<221> NAME/KEY: misc_binding
<222> LOCATION: 21
<223> OTHER INFORMATION: / Hydroxyprolinol amine, 20K PEG

<400> SEQUENCE: 27
nuuacgcuga guacuucgan n                                              21

<210> SEQ ID NO 28
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkages
<220> FEATURE:
<221> NAME/KEY: misc_binding
<222> LOCATION: 21
<223> OTHER INFORMATION: / conjugated to 3'-end of sense
      strand of the apoB siRNA via trans-4-hydroxyprolinol linker
      cholesterol

<400> SEQUENCE: 28
gucaucacac ugaauaccaa n                                              21

<210> SEQ ID NO 29
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: guanine phosphorothioate linkage
<220> FEATURE:
<221> NAME/KEY: misc_binding
<222> LOCATION: 21
<223> OTHER INFORMATION: / conjugated to 3'-end of sense
      strand of the apoB siRNA via trans-4-hydroxyprolinol linker PEG5K

<400> SEQUENCE: 29
nucaucacac ugaauaccaa u                                              21

<210> SEQ ID NO 30
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: guanine phosphorothioate linkage
<220> FEATURE:
<221> NAME/KEY: misc_binding
<222> LOCATION: 21
<223> OTHER INFORMATION: / conjugated to 3'-end of sense
      strand of the apoB siRNA via trans-4-hydroxyprolinol linker PEG20K

<400> SEQUENCE: 30
nucaucacac ugaauaccaa u                                              21

<210> SEQ ID NO 31
<211> LENGTH: 21
<212> TYPE: RNA
<213> ORGANISM: Artificial Sequence
```

```
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: guanine phosphorothioate linkage
<220> FEATURE:
<221> NAME/KEY: misc_binding
<222> LOCATION: 21
<223> OTHER INFORMATION: / conjugated to 3'-end of sense
      strand of the apoB siRNA via trans-4-hydroxyprolinol linker PEG40K

<400> SEQUENCE: 31
nucaucacac ugaauaccaa u                                              21

<210> SEQ ID NO 32
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: cytadine phosphorothioate linkage
<220> FEATURE:
<221> NAME/KEY: misc_feature
<222> LOCATION: 20, 21
<223> OTHER INFORMATION: n = deoxythymidine
<220> FEATURE:
<221> NAME/KEY: misc_binding
<222> LOCATION: 21
<223> OTHER INFORMATION: / conjugated to 3'-end of sense
      strand via trans-4-hydroxyprolinol linker PEG5K

<400> SEQUENCE: 32
nuuacgcuga guacuucgan n                                              21

<210> SEQ ID NO 33
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = deoxythymidine

<400> SEQUENCE: 33
ucgaaguacu cagcguaagn n                                              21

<210> SEQ ID NO 34
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: cytadine phosphorothioate linkage
<220> FEATURE:
<221> NAME/KEY: misc_feature
<222> LOCATION: 20, 21
<223> OTHER INFORMATION: n = deoxythymidine
<220> FEATURE:
<221> NAME/KEY: misc_binding
<222> LOCATION: 21
<223> OTHER INFORMATION: / conjugated to 3'-end of sense
      strand via trans-4-hydroxyprolinol linker PEG20K

<400> SEQUENCE: 34
```
nuuacgcuga guacuucgan n                                       21

<210> SEQ ID NO 35
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: cytadine phosphorothioate linkage
<220> FEATURE:
<221> NAME/KEY: misc_feature
<222> LOCATION: 20, 21
<223> OTHER INFORMATION: n = deoxythymidine
<220> FEATURE:
<221> NAME/KEY: misc_binding
<222> LOCATION: 21
<223> OTHER INFORMATION: / conjugated to 3'-end of sense
      strand via trans-4-hydroxyprolinol linker PEG40K

<400> SEQUENCE: 35
nuuacgcuga guacuucgan n                                       21

<210> SEQ ID NO 36
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = deoxythymidine
<220> FEATURE:
<221> NAME/KEY: misc_binding
<222> LOCATION: 21
<223> OTHER INFORMATION: / conjugated to 3'-end of sense
      strand via trans-4-hydroxyprolinol linker cholesterol

<400> SEQUENCE: 36
cuuacgcuga guacuucgan n                                       21

<210> SEQ ID NO 37
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 4, 5, 6, 9, 10, 11, 12, 13, 14
<223> OTHER INFORMATION: / 2'-O-methyl sugar modification corresponding
      base
<220> FEATURE:
<221> NAME/KEY: misc_binding
<222> LOCATION: 21
<223> OTHER INFORMATION: / conjugated to 3'-end of sense
      strand Behenoil

<400> SEQUENCE: 37
ggccuugacc ucuuagagat t                                       21

<210> SEQ ID NO 38
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:

```
<221> NAME/KEY: modified_base
<222> LOCATION: 5
<223> OTHER INFORMATION: / 2'-O-methyl sugar modification corresponding
      base
<220> FEATURE:
<221> NAME/KEY: misc_feature
<222> LOCATION: 20
<223> OTHER INFORMATION: n = thymidine, phosphorothioate linkage

<400> SEQUENCE: 38
ucucuaagag gucaaggccn t                                                    21

<210> SEQ ID NO 39
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 4, 5, 6, 9, 10, 11, 12, 13, 14
<223> OTHER INFORMATION: / 2'-O-methyl sugar modification corresponding
      base
<220> FEATURE:
<221> NAME/KEY: misc_binding
<222> LOCATION: 21
<223> OTHER INFORMATION: / conjugated to 3'-end of sense strand
      Lithocholic acid

<400> SEQUENCE: 39
ggccuugacc ucuuagagat t                                                    21

<210> SEQ ID NO 40
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 4, 5, 6, 9, 10, 11, 12, 13, 14
<223> OTHER INFORMATION: / 2'-O-methyl sugar modification corresponding
      base
<220> FEATURE:
<221> NAME/KEY: misc_binding
<222> LOCATION: 21
<223> OTHER INFORMATION: / conjugated to 3'-end of sense strand
      Dialkylglicerides

<400> SEQUENCE: 40
ggccuugacc ucuuagagat t                                                    21

<210> SEQ ID NO 41
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 4, 5, 6, 9, 10, 11, 12, 13, 14
<223> OTHER INFORMATION: / 2'-O-methyl sugar modification corresponding
      base
<220> FEATURE:
<221> NAME/KEY: misc_binding
<222> LOCATION: 21
<223> OTHER INFORMATION: / conjugated to 3'-end of sense strand Vitamin
      E

<400> SEQUENCE: 41
ggccuugacc ucuuagagat t                                                    21
```

```
<210> SEQ ID NO 42
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 4, 5, 6, 9, 10, 11, 12, 13, 14
<223> OTHER INFORMATION: / 2'-O-methyl sugar modification corresponding
      base
<220> FEATURE:
<221> NAME/KEY: misc_binding
<222> LOCATION: 21
<223> OTHER INFORMATION: / conjugated to 3'-end of sense strand Stearoyl

<400> SEQUENCE: 42
ggccuugacc ucuuagagat t                                              21

<210> SEQ ID NO 43
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 4, 5, 6, 9, 10, 11, 12, 13, 14
<223> OTHER INFORMATION: / 2'-O-methyl sugar modification corresponding
      base
<220> FEATURE:
<221> NAME/KEY: misc_binding
<222> LOCATION: 21
<223> OTHER INFORMATION: / conjugated to 3'-end of sense strand
      Choleaterol

<400> SEQUENCE: 43
ggccuugacc ucuuagagat t                                              21

<210> SEQ ID NO 44
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: adenine phosphorothioate linkage

<400> SEQUENCE: 44
gucaucacac ugaauaccan u                                              21
```